(12) United States Patent
Kim et al.

(10) Patent No.: US 7,879,835 B2
(45) Date of Patent: Feb. 1, 2011

(54) PHARMACEUTICAL COMPOSITION FOR PREVENTING AND TREATING METABOLIC BONE DISEASES CONTAINING ALPHA-ARYLMETHOXYACTYLATE DERIVATIVES

(75) Inventors: Bum Tae Kim, Daejeon (KR); Yong Ki Min, Daejeon (KR); Yeon Soo Lee, Daejeon (KR); Jung Nyoung Heo, Daejeon (KR); Hyuk Lee, Seoul (KR); No Kyun Park, Daejeon (KR); Jung-Keun Kim, Seongnam-si (KR); Se-Won Kim, Cheonan-si (KR); Seon-Yle Ko, Kongju-si (KR)

(73) Assignees: Korea Research Institute of Chemical Technology, Deajeon (KR); Oscotec Inc., Choongcheongnam-do (KR)

( * ) Notice: Subject to any disclaimer, the term of this patent is extended or adjusted under 35 U.S.C. 154(b) by 865 days.

(21) Appl. No.: 11/570,160

(22) PCT Filed: Jun. 22, 2005

(86) PCT No.: PCT/KR2005/001935

§ 371 (c)(1),
(2), (4) Date: Dec. 7, 2006

(87) PCT Pub. No.: WO2005/123054

PCT Pub. Date: Dec. 29, 2005

(65) Prior Publication Data

US 2008/0280901 A1    Nov. 13, 2008

(30) Foreign Application Priority Data

Jun. 22, 2004    (KR) .................. 10-2004-0046644

(51) Int. Cl.
*A61K 31/33*    (2006.01)
*A61K 31/24*    (2006.01)

(52) U.S. Cl. ....................... 514/183; 514/539

(58) Field of Classification Search ................ 514/183, 514/539

See application file for complete search history.

(56) References Cited

FOREIGN PATENT DOCUMENTS

| EP | 414153 A1 | 2/1991 |
| EP | 463488 A1 | 1/1992 |
| WO | WO 95/20569 A1 | 8/1995 |
| WO | WO 03/087032 A1 | 10/2003 |

OTHER PUBLICATIONS

Dorwald, F. 'Side Reactions in Organic Synthesis: a Guide to Successful Synthesis Design' Wiley-VCH, Preface, p. ix, 2005.*
Jordan, V. 'Tamoxifen: a most unlikely pioneering medicine' Nature Reviews: Drug Discovery, vol. 2, p. 205-213, 2003.*
Allgrove, J. 'Metabolic Bone Disease' Current Paediatrics, vol. 8, p. 19-25, 1998.*

* cited by examiner

*Primary Examiner*—Brandon J Fetterolf
*Assistant Examiner*—Christopher R Stone
(74) *Attorney, Agent, or Firm*—Sughrue Mion, PLLC

(57) ABSTRACT

The present invention relates to a use of a specific alpha-arylmethoxyacrylate derivative, or its pharmacologically acceptable salt or solvate for preventing and treating metabolic bone diseases.

7 Claims, 2 Drawing Sheets

PHARMACEUTICAL COMPOSITION FOR PREVENTING AND TREATING METABOLIC BONE DISEASES CONTAINING ALPHA-ARYLMETHOXYACTYLATE DERIVATIVES

This is a national stage application under 35 U.S.C. 371 of PCT/KR2005/01935 filed on Jun. 22, 2005, which claims priority from Korean patent application 10-2004-0046644 filed on Jun. 22, 2004, all of which are incorporated herein by reference.

FIELD OF THE INVENTION

The present invention relates to a pharmaceutical composition for preventing and treating metabolic bone diseases which contains an alpha-arylmethoxyacrylate derivative, or its pharmacologically acceptable salt or solvate as an active ingredient.

DESCRIPTION OF THE PRIOR ART

Metabolic bone diseases such as osteoporosis are typically caused by reduction of protein, calcium, phosphor and others in bones. Osteoporosis occurs regardless of age and sex with increasing frequency upon aging, especially in a high frequency in postmenopausal women. Recently, the number of osteoporosis patient has been increasing due to the aging of global population and, accordingly, there has existed a need for developing an efficacious medicament for preventing and treating osteoporosis.

Currently available therapeutic agents for osteoporosis include bisphosphonates, hormonal drugs, vitamin D and its analogues, calcitonin, and calcium. Representative bisphosphonates include alendronate (Merck and Co., Ltd.), risedronate (Hoffman-La Roche Ltd.), zoledronate (Novatis A G; EP Patent No. 275,821), ibandronate (Hoffman-La Roche Ltd.; U.S. Pat. No. 4,942,157) and minodronate (Yamanouchi Pharmaceutical Co., Ltd.; EP Patent No. 354,806). Bisphosphonates are major therapeutic agents for osteoporosis; however, they have the disadvantages of low absorption rates through the gastrointestinal tract and possibility of causing esophagitis when not keeping the complicated administration guidance.

Exemplary hormonal drugs include raloxifene (Eli Lilly and Co.), droloxyfene (Pfizer Inc.; EP Patent No. 54168), lasopoxifene (Pfizer Inc.), FC-1271 (homosmedical Co. and Orion Corp., WO 96/07402), TES-424 (Ligand Co. and Weyers Co., U.S. Pat. No. 5,948,775). However, hormonal drugs have the risk of causing breast and uterine cancers and, accordingly, they are limitedly used as a therapeutic agent for osteoporosis which requires a long-term administration.

Further, vitamin D and its analogues are expensive and the therapeutic efficacy for osteoporosis thereof is not clearly established; calcitonin is relatively expensive and requires a difficult administration way; and calcium is known to cause little side effects, but is effective only for the prevention of osteoporosis, having no therapeutic effect.

SUMMARY OF THE INVENTION

Accordingly, it is a primary object of the present invention to provide a novel pharmaceutical composition for preventing and treating a metabolic bone disease having good activity and low side-effects.

In accordance with one aspect of the present invention, there is provided a pharmaceutical composition for preventing and treating metabolic bone diseases comprising a compound of formula (1), or its pharmacologically acceptable salt or solvate as an active ingredient:

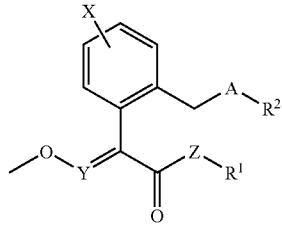

(1)

wherein,
A is O, S, $CH_2$, O—N=CH or O—N=C($CH_3$);
X is H, or a halogen;
Y is N or CH;
Z is O or NH;
$R^1$ is H or $C_{1-4}$ alkyl;
$R^2$ is unsubstituted or substituted aryl or heteroaryl.

In accordance with another aspect of the present invention, there is provided a use of the compound of formula (1), or its pharmacologically acceptable salt or solvate for preventing and treating metabolic bone diseases.

In accordance with a further aspect of the present invention, there is provided a method for preventing and treating metabolic bone diseases using the compound of formula (1), or its pharmacologically acceptable salt or solvate.

BRIEF DESCRIPTION OF THE DRAWINGS

The above and other objects and features of the present invention will become apparent from the following description thereof, when taken in conjunction with the accompanying drawings which respectively show.

DETAILED DESCRIPTION OF THE INVENTION

Figure 1A:
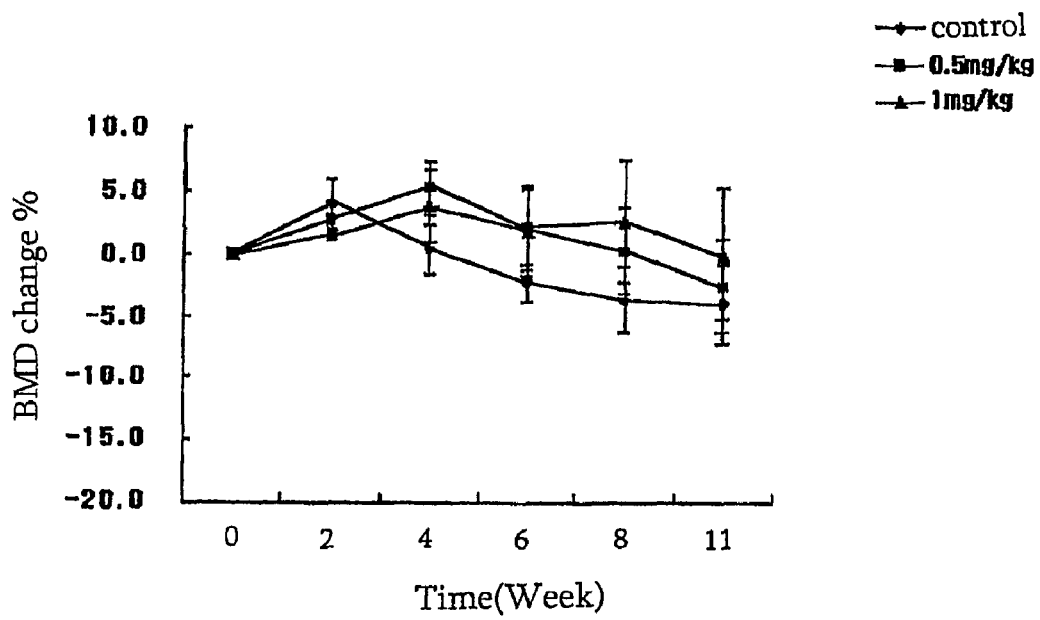
FIGS. 1a and 1b: the changes in bone mineral density (BMD) of multiparous mice ovariectomized to induce osteoporosis observed when the mice were subcutaneously injected with compounds according to the present invention.

In the compound of formula (1), $R^2$ may be an aryl group such as phenyl or naphthyl, or a 5- or 6-membered heterocyclic aromatic ring containing at least one element selected from O, S and N, such as pyridine, pyrimidine, oxazolone, 1,3,4-thiadiazole, cromene, indole, morpholine, thiomorpholine, pyrrolidine, piperidine, piperazine, N-methylpiperazine, N-acetylpiperazine, pyrrolidone, piperidone, oxazolidinone, thiazolidinone, and imidazolone.

Such an aryl or heteroaryl group represented by $R^2$ may be substituted with at least one substituent selected from the group consisting of halogens, cyano, nitro, $C_{1-4}$ haloalkyl, $C_{1-4}$ haloalkenyl, hydroxy, $C_{1-8}$ alkyl, $C_{2-8}$ alkenyl, $C_{2-4}$ alkynyl, $C_{3-6}$ cycloalkyl, $C_{1-8}$ alkoxy, $C_{1-4}$ alkoxy $C_{1-4}$ alkyl, $C_{3-6}$ cycloalkyl $C_{1-4}$ alkyl, $C_{1-4}$ dialkoxy $C_{1-4}$ alkyl, 1,3-dioxolan-2-yl, 1,3-dioxan-2-yl, $C_{2-8}$ alkenyloxy, $C_{2-4}$ alkynyloxy, $C_{3\sim6}$ cycloalkyl $C_{1\sim4}$ alkoxy, hydroxy $C_{1\sim4}$ alkyl, $C_{1\sim4}$ acyloxy, $C_{1\sim4}$ alkylcarbonyl, $C_{1\sim4}$ alkylcarbonyloxy, $C_{3\sim6}$ cycloalkylcarbonyloxy, $C_{1\sim4}$ alkoxycarbonyl, $C_{1\sim4}$ dialkylamino $C_{1\sim4}$ alkoxy, at least one N or O-containing $C_{2\sim5}$ heterocyclo $C_{1\sim4}$ alkoxy, 2-morpholinoethoxy, 2-(piperidin-1-yl)ethoxy), unsubstituted or substituted N-containing heteroaryl, unsubstituted or substituted amino, and unsubstituted or substituted amino $C_{1\sim2}$ alkyl.

The unsubstituted or substituted amino or amino $C_{1\sim2}$ alkyl is represented by —$(CH_2)_n$—$NR^3R^4$, wherein n is 0, 1 or 2, $R^3$ and $R^4$ are each independently H, $C_{1\sim8}$ alkyl, $C_{1\sim8}$ haloalkyl, hydroxy, $C_{2\sim8}$ alkenyl, $C_{2\sim4}$ alkynyl, $C_{3\sim8}$ cycloalkyl, $C_{3\sim8}$ cycloalkyl $C_{1\sim4}$ alkyl, $C_{1\sim4}$ alkoxy $C_{1\sim4}$ alkyl, $C_{3\sim8}$ cycloalkoxy $C_{1\sim4}$ alkyl, $C_{1\sim8}$ alkylsulfonyl, at least one N, O or S-containing $C_{2\sim7}$ heterocyclic $C_{1\sim4}$ alkyl, or an optionally substituted aryl; or $R^3$ and $R^4$ may be fused together with the nitrogen atom to which they are attached to form a heterocyclic ring.

The N-containing heteroaryl substitutent of the aryl or heteroaryl group represented by $R_2$ may be pyrrolyl, imidazolyl, oxazolyl, thiazolyl, triazolyl, pyrazolyl, tetrazolyl, indazolyl, benzoxazolyl, benzothiazolyl, benzoimidazolyl, benzotriazolyl, isoquinolyl and quinazolyl, and it may be further substituted with at least one substituent selected from the group consisting of halogens, cyano, nitro, $C_{1\sim6}$ haloalkyl, $C_{1\sim6}$ haloalkenyl, hydroxy, $C_{1\sim8}$ alkyl, $C_{2\sim8}$ alkenyl, $C_{2\sim4}$ alkynyl, $C_{3\sim6}$ cycloalkyl, $C_{1\sim8}$ alkoxy, $C_{1\sim4}$ alkoxy $C_{1\sim4}$ alkyl, $C_{3\sim8}$ cycloalkyl $C_{1\sim4}$ alkyl, $C_{1\sim4}$ dialkoxy $C_{1\sim4}$ alkyl, $C_{2\sim8}$ alkenyloxy, $C_{2\sim4}$ alkynyloxy, $C_{3\sim6}$ cycloalkyl $C_{1\sim4}$ alkoxy, hydroxy $C_{1\sim4}$ alkyl, $C_{1\sim4}$ acyloxy, $C_{1\sim4}$ alkylcarbonyl, $C_{1\sim4}$ alkylcarbonyloxy, $C_{3\sim8}$ cycloalkylcarbonyloxy, $C_{1\sim4}$ alkoxycarbonyl, $C_{1\sim4}$ dialkylamino, and $SO_2NR^5R^6$, $R^5$ and $R^6$ being each independently H or $C_{1\sim6}$ alkyl.

Representative examples of the compound of formula (1) include those shown in Tables 1a to 1l, and Tables 3a to 3n later.

TABLE 1a

| Compound No. | A | X | Y | Z | $R^1$ | $R^2$ | mp (° C.) |
|---|---|---|---|---|---|---|---|
| 1 | S | H | CH | O | $CH_3$ | 4-F—$C_6H_4$ | |
| 2 | S | H | CH | O | $CH_3$ | 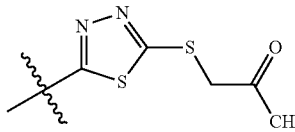 | |
| 3 | S | H | CH | O | $CH_3$ | 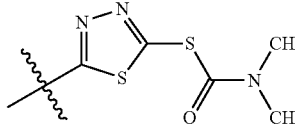 | |
| 4 | S | H | CH | O | $CH_3$ | 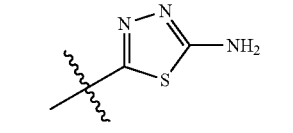 | 141-142 |
| 5 | ON=C($CH_3$) | H | N | O | $CH_3$ | 3-HO—$C_6H_4$ | |
| 6 | ON=C($CH_3$) | H | CH | O | $CH_3$ | 3-HO—$C_6H_4$ | |
| 7 | ON=C($CH_3$) | H | CH | O | $CH_3$ | 3-$CH_2$=$CHCH_2$O—$C_6H_4$ | |
| 8 | ON=C($CH_3$) | H | CH | O | $CH_3$ | 3-$CH_3(CH_2)_3$O—$C_6H_4$ | |
| 9 | ON=C($CH_3$) | H | CH | O | $CH_3$ | 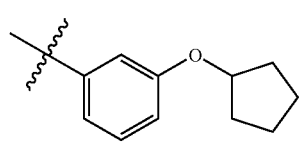 | |
| 10 | ON=C($CH_3$) | H | CH | O | $CH_3$ | 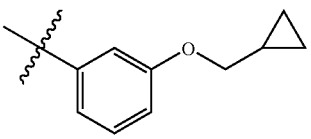 | |
| 11 | ON=C($CH_3$) | H | CH | O | $CH_3$ | 3-$(CH_3)_2CH(CH_3)_2$O—$C_6H_4$ | |
| 12 | ON=C($CH_3$) | H | CH | O | $CH_3$ | 3-$(CH_3)_2C$=$CHCH_2$O—$C_6H_4$ | |

TABLE 1a-continued

| Compound No. | A | X | Y | Z | R¹ | R² | mp (° C.) |
|---|---|---|---|---|---|---|---|
| 13 | ON=C(CH₃) | H | CH | O | CH₃ | 3-(1,3-dioxolan-2-ylmethoxy)-C₆H₄ | |
| 14 | ON=C(CH₃) | H | CH | O | CH₃ | 3-(CH₃)₂CHCH₂O—C₆H₄ | |
| 15 | ON=C(CH₃) | H | CH | O | CH₃ | 3-CH₃(CH₂)₅O—C₆H₄ | 41-42 |
| 16 | ON=C(CH₃) | H | CH | O | CH₃ | 3-CH₃O(CH₂)₂O—C₆H₄ | |
| 17 | ON=C(CH₃) | H | CH | O | CH₃ | 3-CH₃O₂CCH(CH₃)O—C₆H₄ | |
| 18 | ON=C(CH₃) | H | CH | O | CH₃ | 3-CNCH₂O—C₆H₄ | |
| 19 | ON=C(CH₃) | H | CH | O | CH₃ | 3-(CH₃)₂N(CH₂)₂O—C₆H₄ | |
| 20 | ON=C(CH₃) | H | CH | O | CH₃ | 3-(2-morpholinoethoxy)-C₆H₄ | |
| 21 | ON=C(CH₃) | H | CH | O | CH₃ | 3-(2-pyrrolidinoethoxy)-C₆H₄ | |
| 22 | ON=C(CH₃) | H | CH | O | CH₃ | 3-CH₃CO₂—C₆H₄ | |
| 23 | ON=C(CH₃) | H | CH | O | CH₃ | 3-CH₃(CH₂)₃CO₂—C₆H₄ | |
| 24 | ON=C(CH₃) | H | CH | O | CH₃ | 3-(cyclopropylcarbonyloxy)-C₆H₄ | |
| 25 | ON=CH | H | CH | O | CH₃ | 3-CH₂=CHCH₂O—C₆H₄ | |
| 26 | ON=CH | H | CH | O | CH₃ | 3-CNCH₂O—C₆H₄ | |
| 27 | ON=CH | H | CH | O | CH₃ | 3-CH₃(CH₂)₃O—C₆H₄ | |

TABLE 1b

| 28 | ON=CH | H | CH | O | CH₃ | 3-(1,3-dioxolan-2-ylmethoxy)-C₆H₄ | |
|---|---|---|---|---|---|---|---|
| 29 | ON=CH | H | CH | O | CH₃ | 3-CH₃O(CH₂)₂O—C₆H₄ | |
| 30 | O | H | N | O | CH₃ | 3-CHO—C₆H₄ | |
| 31 | O | H | N | O | CH₃ | 3-F₂C=CH—C₆H₄ | |
| 32 | O | H | N | O | CH₃ | 4-CN—C₆H₄ | |
| 33 | O | H | N | O | CH₃ | 4-NO₂—C₆H₄ | |
| 34 | O | H | N | O | CH₃ | 3-Br—C₆H₄ | |
| 35 | O | H | N | O | CH₃ | 4-CH₃O₂C—C₆H₄ | |
| 36 | O | H | N | O | CH₃ | 3,4-Di-F—C₆H₃ | |
| 37 | O | H | N | O | CH₃ | 4-CH₃(CH₂)₅O—C₆H₄ | |
| 38 | O | H | N | O | CH₃ | 4-(CH₃)₂CHCH₂O—C₆H₄ | |
| 39 | O | H | N | O | CH₃ | 4-CH₃CH₂CH(CH₃)O—C₆H₄ | |

TABLE 1b-continued
| | | | | | | | |
|---|---|---|---|---|---|---|---|
| 40 | O | H | N | O | CH₃ | 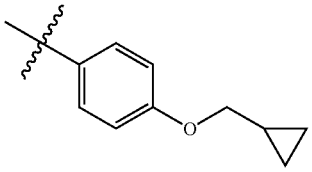 | |
| 41 | O | H | N | O | CH₃ | 4-(CH₃)₂C=CHCH₂O—C₆H₄ | |
| 42 | O | H | N | O | CH₃ | 4-CH₂=CH(CH₂)₂O—C₆H₄ | |
| 43 | O | H | N | O | CH₃ | 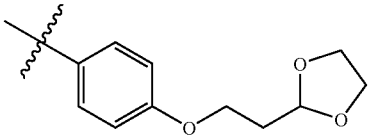 | |
| 44 | O | H | N | O | CH₃ | 4-CH₂=CHCH₂O—C₆H₄ | |
| 45 | O | H | N | O | CH₃ | 4-CH≡CCH₂O—C₆H₄ | |
| 46 | O | H | N | O | CH₃ | 4-CH₃(CH₂)₃O—C₆H₄ | |
| 47 | O | H | N | O | CH₃ | 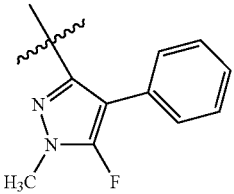 | 103-104 |
| 48 | O | H | N | O | CH₃ | 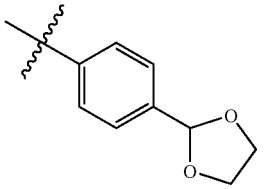 | |
| 49 | O | H | N | O | CH₃ | 4-(CH₃O)₂CH—C₆H₄ | |
| 50 | O | H | N | O | CH₃ | 4-t-Bu—C₆H₄ | |
| 51 | O | H | N | O | CH₃ | 3-CH₃COCH₂CH(OH)—C₆H₄ | |
| 52 | O | H | N | O | CH₃ | 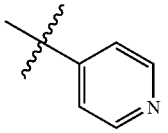 | |
| 53 | O | H | N | O | CH₃ | 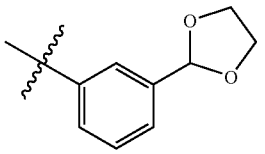 | |
| 54 | O | H | N | O | CH₃ | 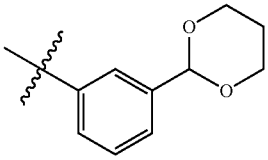 | |
| 55 | O | H | N | O | CH₃ | 3-F₂CH—C₆H₄ | |
| 56 | O | H | N | O | CH₃ | 3-CH₃COCH₂CHF—C₆H₄ | |

TABLE 1c

| | | | | | | |
|---|---|---|---|---|---|---|
| 57 | O | H | N | O | CH₃ | 4-CHO—C₆H₄ |
| 58 | O | H | N | O | CH₃ | (4-(1,3-dioxan-2-yl)phenyl) |
| 59 | O | H | N | O | CH₃ | 3-CH₃-4-Cl—C₆H₃ |
| 60 | O | H | N | O | CH₃ | 3,4-Di-Cl—C₆H₃ |
| 61 | O | H | N | O | CH₃ | 4-F₂CH—C₆H₄ |
| 62 | O | H | N | O | CH₃ | 2-CHO—C₆H₄ |
| 63 | O | H | N | O | CH₃ | 3-Cl-5-CH₃O—C₆H₃ |
| 64 | O | H | N | O | CH₃ | 3-(CH₃O)₂CH—C₆H₄ |
| 65 | O | H | N | O | CH₃ | 2-F₂CH—C₆H₄ |
| 66 | O | H | N | O | CH₃ | 2-(CH₃O)₂CH—C₆H₄ |
| 67 | O | H | N | O | CH₃ | (2-(1,3-dioxolan-2-yl)phenyl) |
| 68 | O | H | N | O | CH₃ | (2-(1,3-dioxan-2-yl)phenyl) |

TABLE 1c-continued

| | | | | | | |
|---|---|---|---|---|---|---|
| 69 | O | H | N | O | CH₃ | C₆H₅ |
| 70 | O | H | N | O | CH₃ | 2-CH₃—C₆H₄ |
| 71 | O | H | N | O | CH₃ | 4-CH₃—C₆H₄ |
| 72 | O | H | N | O | CH₃ | 3-Cl—C₆H₄ |
| 73 | O | H | N | O | CH₃ | 4-Cl—C₆H₄ |
| 74 | O | H | N | O | CH₃ | 3-F—C₆H₄ |
| 75 | O | H | N | O | CH₃ | 4-F—C₆H₄ |
| 76 | O | H | N | O | CH₃ | 3-CH₃OC—C₆H₄ |
| 77 | O | H | CH | O | CH₂CH₃ | 4-CH₃—C₆H₄ |
| 78 | O | H | CH | O | CH₂CH₃ | 3-Cl—C₆H₄ |
| 79 | O | H | CH | O | CH₂CH₃ | 4-F—C₆H₄ |
| 80 | O | H | CH | O | CH₂CH₃ | 4-Br—C₆H₄ |
| 81 | O | H | CH | O | CH₂CH₃ | 4-t-Bu—C₆H₄ |
| 82 | O | H | CH | O | CH₂CH₃ | (3-(1,3-dioxan-2-yl)phenyl) |
| 83 | O | H | CH | O | CH₂CH₃ | 3-(CH₃O)₂CH—C₆H₄ |
| 84 | O | H | CH | O | CH₂CH₃ | 3-HOCH₂—C₆H₄ |
| 85 | O | H | CH | O | CH₂CH₃ | (3-(cyclopentyloxy)phenyl) |
| 86 | O | H | CH | O | CH₂CH₃ | 3-CH₃(CH₂)₅O—C₆H₄ |
| 87 | O | H | CH | O | CH₂CH₃ | 3-(CH₃)₂CHCH₂O—C₆H₄ |
| 88 | O | H | CH | O | CH₂CH₃ | 3-CH₃O₂CCH(CH₃)O—C₆H₄ |
| 89 | O | H | CH | O | CH₂CH₃ | 3-CH₂=CHCH₂O—C₆H₄ |

TABLE 1d

| | | | | | | |
|---|---|---|---|---|---|---|
| 90 | O | H | CH | O | CH(CH₃)₂ | (3-(1,3-dioxolan-2-yl)phenyl) |
| 91 | O | H | CH | O | CH(CH₃)₂ | (3-(1,3-dioxan-2-yl)phenyl) |
| 92 | O | H | CH | O | CH(CH₃)₂ | 3-HOCH₂—C₆H₄ |
| 93 | O | H | CH | O | CH(CH₃)₂ | 3-F₂CH—C₆H₄ |
| 94 | O | H | CH | O | CH(CH₃)₂ | 3-(CH₃O)₂CH—C₆H₄ |
| 95 | O | H | CH | O | CH(CH₃)₂ | 4-CH₃—C₆H₄ |
| 96 | O | H | CH | O | CH(CH₃)₂ | 3-Cl—C₆H₄ |
| 97 | O | H | CH | O | CH(CH₃)₂ | 4-F—C₆H₄ |
| 98 | O | H | CH | O | CH(CH₃)₂ | 3-Br—C₆H₄ |
| 99 | O | H | CH | O | CH(CH₃)₂ | 4-t-Bu—C₆H₄ |

TABLE 1d-continued

| | | | | | | | |
|---|---|---|---|---|---|---|---|
| 100 | O | H | CH | O | CH(CH$_3$)$_2$ | 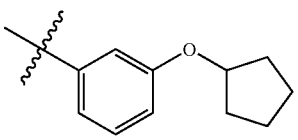 | |
| 101 | O | H | CH | O | CH(CH$_3$)$_2$ | 3-CH$_3$O(CH$_2$)$_2$O—C$_6$H$_4$ | |
| 102 | O | H | CH | O | CH(CH$_3$)$_2$ | 3-CH$_3$(CH$_2$)$_5$O—C$_6$H$_4$ | |
| 103 | O | H | CH | O | CH(CH$_3$)$_2$ | 3-(CH$_3$)$_2$CHCH$_2$O—C$_6$H$_4$ | |
| 104 | O | H | CH | O | CH(CH$_3$)$_2$ | 3-CH$_3$CH$_2$CH(CH$_3$)O—C$_6$H$_4$ | |
| 105 | O | H | CH | O | CH(CH$_3$)$_2$ | 3-(CH$_3$)$_2$C=CHCH$_2$O—C$_6$H$_4$ | |
| 106 | O | H | CH | O | CH(CH$_3$)$_2$ | 3-CH$_3$(CH$_2$)$_3$O—C$_6$H$_4$ | |
| 107 | O | H | CH | O | CH(CH$_3$)$_2$ | 3-CH$_2$=CH(CH$_2$)$_2$O—C$_6$H$_4$ | |
| 108 | O | H | CH | O | CH(CH$_3$)$_2$ | 3-CH$_3$O$_2$CCH(CH$_3$)O—C$_6$H$_4$ | |
| 109 | O | H | CH | O | CH(CH$_3$)$_2$ | 4-CH$_2$=CHCH$_2$O—C$_6$H$_4$ | |
| 110 | O | H | CH | O | CH(CH$_3$)$_2$ | 4-CH≡CCH$_2$O—C$_6$H$_4$ | |
| 111 | O | H | CH | O | CH(CH$_3$)$_2$ | 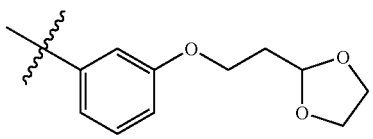 | |
| 112 | O | H | CH | O | CH$_3$ | 3-C$_6$H$_5$CO$_2$—C$_6$H$_4$ | 121-122 |
| 113 | O | H | CH | O | CH$_3$ | 3-HO—C$_6$H$_4$ | |
| 114 | O | H | CH | O | CH$_3$ | 3-CH$_3$COCH$_2$CH(OH)—C$_6$H$_4$ | |
| 115 | O | H | CH | O | CH$_3$ | 3-CH$_3$COCH=CH—C$_6$H$_4$ | 97-98 |
| 116 | O | H | CH | O | CH$_3$ | 3-CHO—C$_6$H$_4$ | |
| 117 | O | H | CH | O | CH$_3$ | 3-F$_2$C=CH—C$_6$H$_4$ | |
| 118 | O | H | CH | O | CH$_3$ | 4-CF$_3$CO—C$_6$H$_4$ | |
| 119 | O | H | CH | O | CH$_3$ | 4-CF$_3$CH(OH)—C$_6$H$_4$ | |
| 120 | O | H | CH | O | CH$_3$ | 4-CF$_3$CH(Cl)—C$_6$H$_4$ | |
| 121 | O | H | CH | O | CH$_3$ | 4-CHO—C$_6$H$_4$ | 84-85 |
| 122 | O | H | CH | O | CH$_3$ | 2-CHO—C$_6$H$_4$ | |
| 123 | O | H | CH | O | CH$_3$ | 2-F$_2$CH—C$_6$H$_4$ | |
| 124 | O | H | CH | O | CH$_3$ | C$_6$H$_4$ | |
| 125 | O | H | CH | O | CH$_3$ | 2-CH$_3$—C$_6$H$_4$ | |
| 126 | O | H | CH | O | CH$_3$ | 4-CH$_3$—C$_6$H$_4$ | |
| 127 | O | H | CH | O | CH$_3$ | 3-Cl—C$_6$H$_4$ | |
| 128 | O | H | CH | O | CH$_3$ | 4-Cl—C$_6$H$_4$ | |
| 129 | O | H | CH | O | CH$_3$ | 3-F—C$_6$H$_4$ | |
| 130 | O | H | CH | O | CH$_3$ | 4-F—C$_6$H$_4$ | |

TABLE 1e

| | | | | | | | |
|---|---|---|---|---|---|---|---|
| 131 | O | H | CH | O | CH$_3$ | 3-CH$_3$OC—C$_6$H$_4$ | 76-77 |
| 132 | O | H | CH | O | CH$_3$ | 4-CH$_3$O$_2$C—C$_6$H$_4$ | |
| 133 | O | H | CH | O | CH$_3$ | 3-(CH$_3$O)$_2$CH—C$_6$H$_4$ | |
| 134 | O | H | CH | O | CH$_3$ | 4-CN—C$_6$H$_4$ | |
| 135 | O | H | CH | O | CH$_3$ | 4-NO$_2$—C$_6$H$_4$ | |
| 136 | O | H | CH | O | CH$_3$ | 3-Br—C$_6$H$_4$ | |
| 137 | O | H | CH | O | CH$_3$ | 3,4-Di-F—C$_6$H$_3$ | |
| 138 | O | H | CH | O | CH$_3$ | 3-CH$_3$—C$_6$H$_4$ | |
| 139 | O | H | CH | O | CH$_3$ | 2-Cl—C$_6$H$_4$ | |
| 140 | O | H | CH | O | CH$_3$ | 2-F—C$_6$H$_4$ | |
| 141 | O | H | CH | O | CH$_3$ | 2,4-Di-Cl—C$_6$H$_3$ | |
| 142 | O | H | CH | O | CH$_3$ | 2,5-Di-Cl—C$_6$H$_3$ | |
| 143 | O | H | CH | O | CH$_3$ | 2,6-Di-Cl—C$_6$H$_3$ | |
| 144 | O | H | CH | O | CH$_3$ | 3,5-Di-Cl—C$_6$H$_3$ | |
| 145 | O | H | CH | O | CH$_3$ | 2,4-Di-t-Bu—C$_6$H$_3$ | |
| 146 | O | H | CH | O | CH$_3$ | 2,6-Di-F—C$_6$H$_3$ | |
| 147 | O | H | CH | O | CH$_3$ | 2,4,6-Tri-Cl—C$_6$H$_2$ | |
| 148 | O | H | CH | O | CH$_3$ | 2,4,5-Tri-Cl—C$_6$H$_2$ | |
| 149 | O | H | CH | O | CH$_3$ | 2,-CH$_3$-4-Cl—C$_6$H$_3$ | |
| 150 | O | H | CH | O | CH$_3$ | 3,5-Di-CH$_3$-4-Cl—C$_6$H$_2$ | |
| 151 | O | H | CH | O | CH$_3$ | 3-CH$_3$O—C$_6$H$_4$ | |
| 152 | O | H | CH | O | CH$_3$ | 2-CN—C$_6$H$_4$ | |
| 153 | O | H | CH | O | CH$_3$ | 3-CN—C$_6$H$_4$ | |
| 154 | O | H | CH | O | CH$_3$ | 4-F$_2$C=CH—C$_6$H$_4$ | 55-57 |
| 155 | O | H | CH | O | CH$_3$ | 4-CH$_3$O$_2$CCH$_2$—C$_6$H$_4$ | |
| 156 | O | H | CH | O | CH$_3$ | 3-CH$_3$CH(OH)—C$_6$H$_4$ | |

TABLE 1e-continued

| 157 | O | H | CH | O | CH₃ | 4-[C(OH)(CH₂COCH₃)(CF₃)]—C₆H₄ |
| 158 | O | H | CH | O | CH₃ | 2-(1,3-dioxolan-2-yl)—C₆H₄ |
| 159 | O | H | CH | O | CH₃ | 2-(1,3-dioxan-2-yl)—C₆H₄ |
| 160 | O | H | CH | O | CH₃ | 4-(1,3-dioxolan-2-yl)—C₆H₄ |
| 161 | O | H | CH | O | CH₃ | 4-(1,3-dioxan-2-yl)—C₆H₄ |

TABLE 1f

| 162 | O | H | CH | O | CH₃ | 4-F₂CH—C₆H₄ |
| 163 | O | H | CH | O | CH₃ | 4-(CH₃O)₂CH—C₆H₄ |
| 164 | O | H | CH | O | CH₃ | 2-CH₃CH(OH)—C₆H₄ |
| 165 | O | H | CH | O | CH₃ | 4-CH₃CH(OH)—C₆H₄ |
| 166 | O | H | CH | O | CH₃ | 2-HOCH₂—C₆H₄ |
| 167 | O | H | CH | O | CH₃ | 4-HOCH₂—C₆H₄ |
| 168 | O | H | CH | O | CH₃ | 2-CH₃CH(F)—C₆H₄ |
| 169 | O | H | CH | O | CH₃ | 3-CH₃CH(F)—C₆H₄ |
| 170 | O | H | CH | O | CH₃ | 4-CH₃CH(F)—C₆H₄ |
| 171 | O | H | CH | O | CH₃ | 4-CH₃O(CH₂)₂O—C₆H₄ |
| 172 | O | H | CH | O | CH₃ | 4-(cyclopentyloxy)—C₆H₄ |
| 173 | O | H | CH | O | CH₃ | 4-CH₃(CH₂)₅O—C₆H₄ |
| 174 | O | H | CH | O | CH₃ | 4-(CH₃)₂CHCH₂O—C₆H₄ |

TABLE 1f-continued

| | | | | | | | |
|---|---|---|---|---|---|---|---|
| 175 | O | H | CH | O | CH₃ | 4-CH₃CH₂CH(CH₃)O—C₆H₄ | |
| 176 | O | H | CH | O | CH₃ | 4-(CH₃)₂C=CHCH₂O—C₆H₄ | |
| 177 | O | H | CH | O | CH₃ | 4-CH₃(CH₂)₃O—C₆H₄ | |
| 178 | O | H | CH | O | CH₃ | 4-CH₂=CH(CH₂)₂O—C₆H₄ | |
| 179 | O | H | CH | O | CH₃ | 4-CH₂=CHCH₂O—C₆H₄ | 74-75 |
| 180 | O | H | CH | O | CH₃ | 4-CH₃O₂CCH(CH₃)O—C₆H₄ | |
| 181 | O | H | CH | O | CH₃ | 3-CH₃O₂CCH(CH₃)O—C₆H₄ | |
| 182 | O | H | CH | O | CH₃ | 2-CH₃CH₂O—C₆H₄ | |
| 183 | O | H | CH | O | CH₃ | 4-CH₃CH₂O—C₆H₄ | 77-78 |
| 184 | O | H | CH | O | CH₃ | 2,6-Di-CH₃O—C₆H₃ | |
| 185 | O | H | CH | O | CH₃ | 3,5-Di-CH₃O—C₆H₃ | |
| 186 | O | H | CH | O | CH₃ | 3,4-Di-CH₃O—C₆H₃ | |
| 187 | O | H | CH | O | CH₃ | 2,3-Di-CH₃O—C₆H₃ | |
| 188 | O | H | CH | O | CH₃ | 3,4,5-tri-CH₃O—C₆H₂ | |
| 189 | O | H | CH | O | CH₃ | 4-t-Bu—C₆H₄ | |
| 190 | O | H | CH | O | CH₃ | 3-FCH₂—C₆H₄ | |
| 191 | O | H | CH | O | CH₃ | 4-PhCH₂O—C₆H₄ | |
| 192 | O | H | CH | O | CH₃ | 4-CH₃(CH₂)₂O—C₆H₄ | |
| 193 | O | H | CH | O | CH₃ | 4-CH₃(CH₂)₄O—C₆H₄ | |
| 194 | O | H | CH | O | CH₃ | 4-CH₃(CH₂)₆O—C₆H₄ | |
| 195 | O | H | CH | O | CH₃ | 4-CH₃(CH₂)₇O—C₆H₄ | |
| 196 | O | H | CH | O | CH₃ | 4-CH₂=CH(CH₂)₆O—C₆H₄ | |
| 197 | O | H | CH | O | CH₃ | 3-CH₂=CH(CH₂)₆O—C₆H₄ | |
| 198 | O | H | CH | O | CH₃ | 3-CH₃CH₂O—C₆H₄ | |
| 199 | O | H | CH | O | CH₃ | 3-CH₃(CH₂)₂O—C₆H₄ | |
| 200 | O | H | CH | O | CH₃ | 3-CH₃(CH₂)₄O—C₆H₄ | |
| 201 | O | H | CH | O | CH₃ | 3-CH₃(CH₂)₆O—C₆H₄ | |
| 202 | O | H | CH | O | CH₃ | 3-CH₃(CH₂)₇O—C₆H₄ | |
| 203 | O | H | CH | O | CH₃ | 4-CH₃CO(CH₂)₂—C₆H₄ | |
| 204 | O | H | CH | O | CH₃ | 4-CH₃COCH=CH—C₆H₄ | |

TABLE 1g

| | | | | | | | |
|---|---|---|---|---|---|---|---|
| 205 | O | H | CH | O | CH₃ | 3-CH₃CF₂CH₂CHF—C₆H₄ | |
| 206 | O | H | CH | O | CH₃ | 3-CH₃COCH₂CHF—C₆H₄ | |
| 207 | O | H | CH | O | CH₃ | 3-F₂CH—C₆H₄ | |
| 208 | O | H | CH | O | CH₃ | 3-(CN)₂C=CH—C₆H₄ | 112-113 |
| 209 | O | H | CH | O | CH₃ | 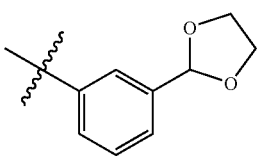 | |
| 210 | O | H | CH | O | CH₃ | 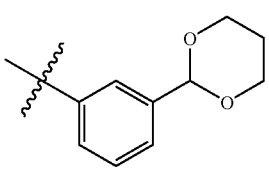 | |
| 211 | O | H | CH | O | CH₃ | 3-CH₂=CHCH₂O—C₆H₄ | |
| 212 | O | H | CH | O | CH₃ | 3-CH₃(CH₂)₃O—C₆H₄ | |
| 213 | O | H | CH | O | CH₃ | 3-CNCH₂O—C₆H₄ | |
| 214 | O | H | CH | O | CH₃ | 3-CH₂=CH(CH₂)₂O—C₆H₄ | |
| 215 | O | H | CH | O | CH₃ | 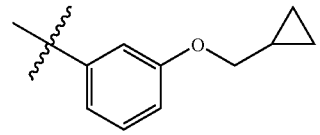 | |
| 216 | O | H | CH | O | CH₃ | 3-(CH₃)₂CH(CH₂)₂O—C₆H₄ | |
| 217 | O | H | CH | O | CH₃ | 3-(CH₃)₂C=CHCH₂O—C₆H₄ | |
| 218 | O | H | CH | O | CH₃ | 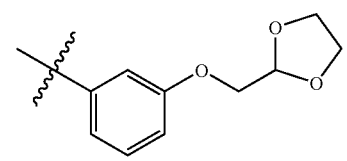 | |

TABLE 1g-continued

| | | | | | | |
|---|---|---|---|---|---|---|
| 219 | O | H | CH | O | CH₃ | 3-(CH₃)₂CHCH₂O—C₆H₄ |
| 220 | O | H | CH | O | CH₃ | 3-CH₃(CH₂)₅O—C₆H₄ |
| 221 | O | H | CH | O | CH₃ | 3-CH₃CH₂CH(CH₃)O—C₆H₄ |
| 222 | O | H | CH | O | CH₃ | 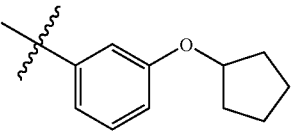 |
| 223 | O | H | CH | O | CH₃ | 3-CH₃O(CH₂)₂O—C₆H₄ |
| 224 | O | H | CH | O | CH₃ | 3-(CH₃CH₂O)₂CH—C₆H₄ |
| 225 | O | H | CH | O | CH₃ | 3-(CH₃CH₂CH₂CH₂O)₂CH—C₆H₄ |
| 226 | O | H | CH | O | CH₃ | 3-Cl-5-CH₃O—C₆H₃ |
| 227 | O | H | CH | O | CH₃ | 3,4-Di-Cl—C₆H₃ |
| 228 | O | H | CH | O | CH₃ | 3-CH₃-4-Cl—C₆H₃ |
| 229 | O | H | CH | O | CH₃ | 3-CH₃(CH₂)₇—C₆H₄ |
| 230 | O | H | CH | O | CH₃ | 4-CH₃(CH₂)₇—C₆H₄ |
| 231 | O | H | CH | O | CH₃ | 3-CH₃CO₂—C₆H₄ |
| 232 | O | H | CH | O | CH₃ | 3-CH₃(CH₂)₂CO₂—C₆H₄ |
| 233 | O | H | CH | O | CH₃ | 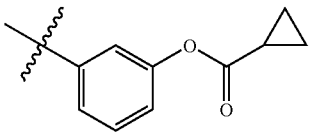 |

TABLE 1h

| | | | | | | |
|---|---|---|---|---|---|---|
| 234 | O | H | CH | O | CH₃ | ![morpholine structure] |
| 235 | O | H | CH | O | CH₃ | ![pyrrolidine structure] |
| 236 | O | H | CH | O | CH₃ | 3-(CH₃)₂N(CH₂)₂O—C₆H₄ |
| 237 | O | H | CH | O | CH₃ | ![naphthyl-O(CH₂)₃CH₃] |
| 238 | O | H | CH | O | CH₃ | ![naphthyl-OCH₂CH=CH₂] |
| 239 | O | H | CH | O | CH₃ | ![naphthyl-O(CH₂)₆CH₃] |

TABLE 1h-continued
| | | | | | | | |
|---|---|---|---|---|---|---|---|
| 240 | O | H | CH | O | CH₃ | 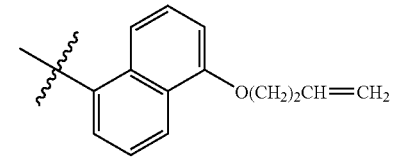 | |
| 241 | O | H | CH | O | CH₃ | 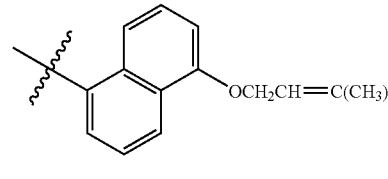 | |
| 242 | O | H | CH | O | CH₃ | 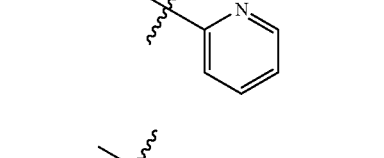 | |
| 243 | O | H | CH | O | CH₃ | 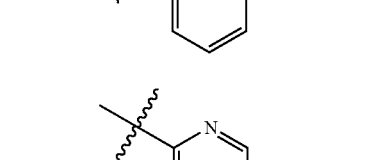 | |
| 244 | O | H | CH | O | CH₃ | 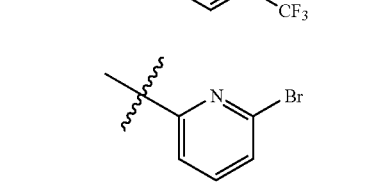 | |
| 245 | O | H | CH | O | CH₃ | 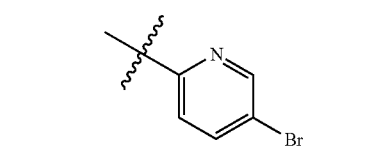 | |
| 246 | O | H | CH | O | CH₃ | 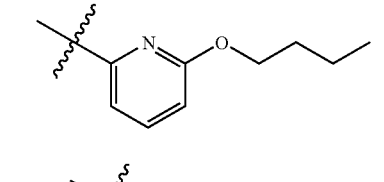 | |
| 247 | O | H | CH | O | CH₃ | 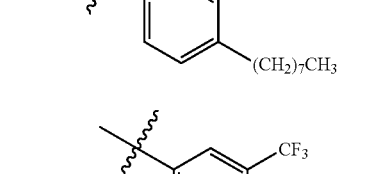 | |
| 248 | O | H | CH | O | CH₃ | | |
| 249 | O | H | CH | O | CH₃ | 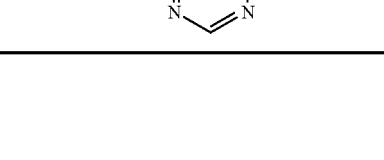 | 110-111 |

TABLE 1i

| 250 | O | H | CH | O | CH₃ | 5-indolyl |
| 251 | O | H | CH | O | CH₃ | 7-(2-oxo-2H-chromenyl) |
| 252 | O | H | CH | O | CH₃ | 3-(4-chlorophenyl)-4-oxo-4H-chromen-6-yl |
| 253 | O | H | CH | O | CH₃ | 3-(4-methoxyphenyl)-4-oxo-4H-chromen-6-yl |
| 254 | O | H | CH | O | CH₃ | 4-oxo-3-phenyl-4H-chromen-7-yl |
| 255 | O | H | CH | O | CH₃ | 3-(4-chlorophenyl)-4-oxo-4H-chromen-7-yl |
| 256 | O | H | CH | O | CH₃ | 5-fluoro-1-methyl-4-phenyl-1H-pyrazol-3-yl |
| 257 | O | H | CH | O | CH₃ | 1-benzyl-5-fluoro-4-phenyl-1H-pyrazol-3-yl |

TABLE 1i-continued

| | | | | | | |
|---|---|---|---|---|---|---|
| 258 | O | H | CH | O | CH$_3$ | 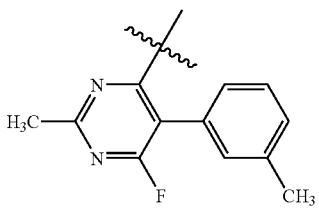 |
| 259 | O | 4-Cl | CH | O | CH$_3$ | 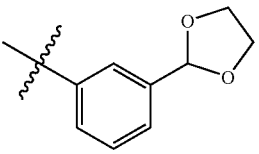 |
| 260 | O | 4-Cl | CH | O | CH$_3$ | 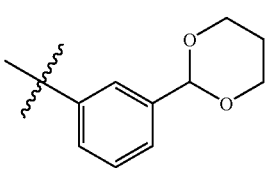 |
| 261 | O | 4-Cl | CH | O | CH$_3$ | 3-F$_2$CH—C$_6$H$_4$ |
| 262 | O | 4-Cl | CH | O | CH$_3$ | 3-HOCH$_2$—C$_6$H$_4$ |
| 263 | O | 4-Cl | CH | O | CH$_3$ | 3-FCH$_2$—C$_6$H$_4$ |
| 264 | O | 4-Cl | CH | O | CH$_3$ | 4-CH$_2$=CHCH$_2$O—C$_6$H$_4$ |
| 265 | O | 4-Cl | CH | O | CH$_3$ | 4-CH$_3$(CH$_2$)$_3$O—C$_6$H$_4$ |
| 266 | O | 4-Cl | CH | O | CH$_3$ | 4-CH$_2$=CH(CH$_2$)$_2$O—C$_6$H$_4$ |
| 267 | O | 4-Cl | CH | O | CH$_3$ | 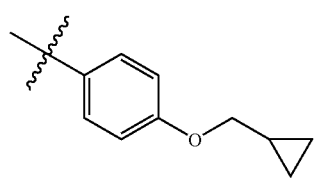 |
| 268 | O | 4-Cl | CH | O | CH$_3$ | 4-(CH$_3$)$_2$CH(CH$_2$)$_2$O—C$_6$H$_4$ |
| 269 | O | 4-Cl | CH | O | CH$_3$ | 4-(CH$_3$)$_2$C=CHCH$_2$O—C$_6$H$_4$ |

TABLE 1j

| | | | | | | |
|---|---|---|---|---|---|---|
| 270 | O | 4-Cl | CH | O | CH$_3$ | 4-(CH$_3$)$_2$CHCH$_2$O—C$_6$H$_4$ |
| 271 | O | 4-Cl | CH | O | CH$_3$ | 4-CH$_3$(CH$_2$)$_5$O—C$_6$H$_4$ |
| 272 | O | 4-Cl | CH | O | CH$_3$ | 4-CH$_3$CH$_2$CH(CH$_3$)O—C$_6$H$_4$ |
| 273 | O | 4-Cl | CH | O | CH$_3$ | 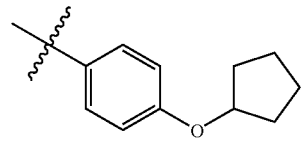 |
| 274 | O | 4-Cl | CH | O | CH$_3$ | 4-CH$_3$O(CH$_2$)$_2$O—C$_6$H$_4$ |
| 275 | O | 4-Cl | CH | O | CH$_3$ | 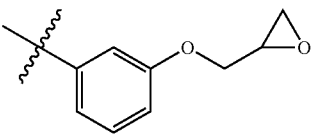 |

TABLE 1j-continued

| | | | | | | |
|---|---|---|---|---|---|---|
| 276 | O | 4-Cl | CH | O | CH₃ | 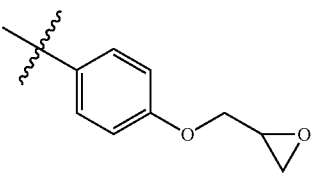 |
| 277 | O | 3-F | CH | O | CH₃ | 3-CH₂=CHCH₂O—C₆H₄ |
| 278 | O | 3-F | CH | O | CH₃ | 3-CH₃(CH₂)₃O—C₆H₄ |
| 279 | O | 3-F | CH | O | CH₃ | 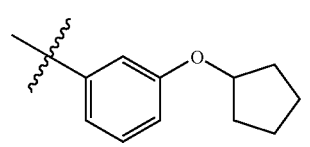 |
| 280 | O | 3-F | CH | O | CH₃ | 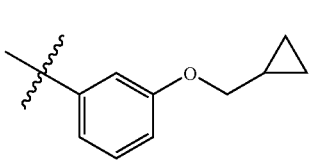 |
| 281 | O | 3-F | CH | O | CH₃ | 3-(CH₃)₂CH(CH₂)₂O—C₆H₄ |
| 282 | O | 3-F | CH | O | CH₃ | 3-(CH₃)₂C=CHCH₂O—C₆H₄ |
| 283 | O | 3-F | CH | O | CH₃ | 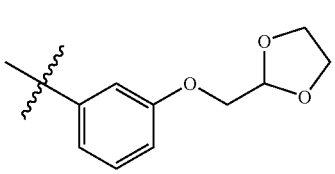 |
| 284 | O | 3-F | CH | O | CH₃ | 3-(CH₃)₂CHCH₂O—C₆H₄ |
| 285 | O | 3-F | CH | O | CH₃ | 3-CH₃(CH₂)₅O—C₆H₄ |
| 286 | O | 3-F | CH | O | CH₃ | 3-CH₃CH₂CH(CH₃)O—C₆H₄ |
| 287 | O | 3-F | CH | O | CH₃ | 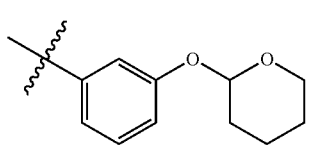 |
| 288 | O | 3-F | CH | O | CH₃ | 3-CH₃CH=CHCH₂O—C₆H₄ |
| 289 | O | 3-F | CH | O | CH₃ | 4-CH₂=CHCH₂O—C₆H₄ |
| 290 | O | 3-F | CH | O | CH₃ | 4-CH₃(CH₂)₃O—C₆H₄ |
| 291 | O | 3-F | CH | O | CH₃ | 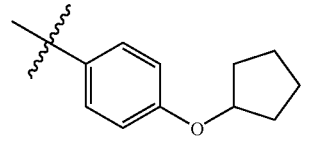 |
| 292 | O | 3-F | CH | O | CH₃ | 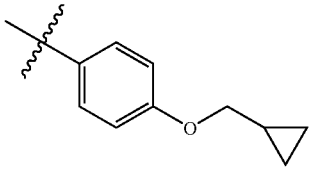 |
| 293 | O | 3-F | CH | O | CH₃ | 4-(CH₃)₂CH(CH₂)₂O—C₆H₄ |

TABLE 1j-continued

| 294 | O | 3-F | CH | O | CH₃ | 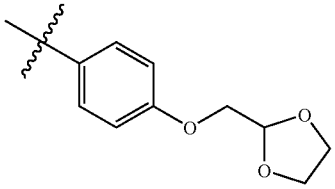 |
| --- | --- | --- | --- | --- | --- | --- |
| 295 | O | 3-F | CH | O | CH₃ | 4-(CH₃)₂CHCH₂O—C₆H₄ |
| 296 | O | 3-F | CH | O | CH₃ | 4-CH₃(CH₂)₅O—C₆H₄ |
| 297 | O | 3-F | CH | O | CH₃ | 4-CH₃CH₂CH(CH₃)O—C₆H₄ |

TABLE 1k

| 298 | O | 3-F | CH | O | CH₃ | 4-CH₃O(CH₂)₂O—C₆H₄ |
| --- | --- | --- | --- | --- | --- | --- |
| 299 | O | 3-F | CH | O | CH₃ | 4-CH₃CH=CHCH₂O—C₆H₄ |
| 300 | O | 3-F | CH | O | CH₃ | 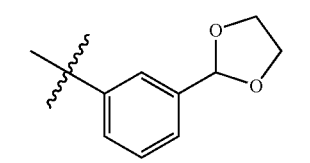 |
| 301 | O | 3-F | CH | O | CH₃ | 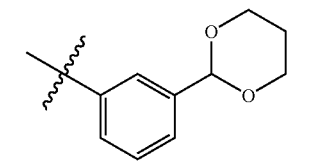 |
| 302 | O | 3-F | CH | O | CH₃ | 3-(CH₃O)₂CH—C₆H₄ |
| 303 | O | 3-F | CH | O | CH₃ | 3-HOCH₂—C₆H₄ |
| 304 | O | 3-F | CH | O | CH₃ | 3-FCH₂—C₆H₄ |
| 305 | O | 4-F | CH | O | CH₃ | 3-CH₃O(CH₂)₂O—C₆H₄ |
| 306 | O | 4-F | CH | O | CH₃ | 4-CH₃O(CH₂)₂O—C₆H₄ |
| 307 | O | 4-F | CH | O | CH₃ | 3-CH₂=CHCH₂O—C₆H₄ |
| 308 | O | 4-F | CH | O | CH₃ | 4-CH₂=CHCH₂O—C₆H₄ |
| 309 | O | 4-F | CH | O | CH₃ | 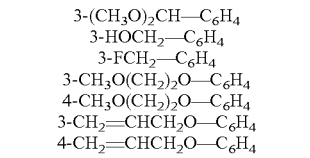 |
| 310 | O | 4-F | CH | O | CH₃ | 3-(CH₃)₂CH(CH₂)₂O—C₆H₄ |
| 311 | O | 4-F | CH | O | CH₃ | 3-CH₃(CH₂)₃O—C₆H₄ |
| 312 | O | 4-F | CH | O | CH₃ | 3-CH₃(CH₂)₅O—C₆H₄ |
| 313 | O | 4-F | CH | O | CH₃ | 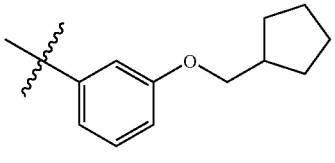 |
| 314 | O | 4-F | CH | O | CH₃ | 3-(CH₃)₂C=CHCH₂O—C₆H₄ |
| 315 | O | 4-F | CH | O | CH₃ | 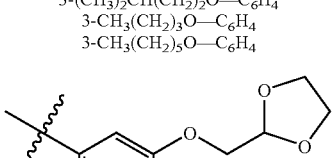 |
| 316 | O | 4-F | CH | O | CH₃ | 4-(CH₃)₂CH(CH₂)₂O—C₆H₄ |

TABLE 1k-continued

| | | | | | | |
|---|---|---|---|---|---|---|
| 317 | O | 4-F | CH | O | CH₃ | 4-CH₃(CH₂)₃O—C₆H₄ |
| 318 | O | 4-F | CH | O | CH₃ | *p-phenoxy-methyl-1,3-dioxolane substituent* |
| 319 | O | 4-F | CH | O | CH₃ | 4-CH₃CH₂CH(CH₃)O—C₆H₄ |
| 320 | O | 4-F | CH | O | CH₃ | *p-phenoxy-methyl-oxirane substituent* |
| 321 | CH₂ | H | CH | O | CH₃ | 3-HO—C₆H₄ |
| 322 | CH₂ | H | CH | O | CH₃ | 3-CH₃(CH₂)₂O—C₆H₄ |
| 323 | CH₂ | H | CH | O | CH₃ | 3-CH₃(CH₂)₃O—C₆H₄ |
| 324 | CH₂ | H | CH | O | CH₃ | 3-CH₃(CH₂)₄O—C₆H₄ |
| 325 | CH₂ | H | CH | O | CH₃ | 3-CH₃(CH₂)₅O—C₆H₄ |
| 326 | CH₂ | H | CH | O | CH₃ | 3-CH₃(CH₂)₆O—C₆H₄ |
| 327 | CH₂ | H | CH | O | CH₃ | 3-CH₃(CH₂)₇O—C₆H₄ |
| 328 | CH₂ | H | CH | O | CH₃ | 3-(CH₃)₂CH(CH₂)₂O—C₆H₄ |

TABLE 1l

| | | | | | | |
|---|---|---|---|---|---|---|
| 329 | CH₂ | H | CH | O | CH₃ | 3-(CH₃)₂CHCH₂O—C₆H₄ |
| 330 | CH₂ | H | CH | O | CH₃ | 3-CH₃CH₂CH(CH₃)O—C₆H₄ |
| 331 | CH₂ | H | CH | O | CH₃ | 3-CH₂=CHCH₂O—C₆H₄ |
| 332 | CH₂ | H | CH | O | CH₃ | 3-(CH₃)₂C=CHCH₂O—C₆H₄ |
| 333 | CH₂ | H | CH | O | CH₃ | *m-(cyclopentylmethoxy)phenyl substituent* |
| 334 | CH₂ | H | CH | O | CH₃ | 3-CH₃O(CH₂)₂O—C₆H₄ |
| 335 | CH₂ | H | CH | O | CH₃ | *m-(cyclopropylmethoxy)phenyl substituent* |
| 336 | CH₂ | H | CH | O | CH₃ | 4-CH₂=CHCH₂O—C₆H₄ |
| 337 | CH₂ | H | CH | O | CH₃ | 4-CH₃(CH₂)₃O—C₆H₄ |
| 338 | CH₂ | H | CH | O | CH₃ | *p-(cyclopentylmethoxy)phenyl substituent* |

TABLE 11-continued

| | | | | | | |
|---|---|---|---|---|---|---|
| 339 | CH$_2$ | H | CH | O | CH$_3$ | 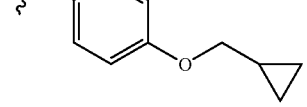 |
| 340 | CH$_2$ | H | CH | O | CH$_3$ | 4-(CH$_3$)$_2$CH(CH$_2$)$_2$O—C$_6$H$_4$ |
| 341 | CH$_2$ | H | CH | O | CH$_3$ | 4-(CH$_3$)$_2$C=CHCH$_2$O—C$_6$H$_4$ |
| 342 | CH$_2$ | H | CH | O | CH$_3$ | 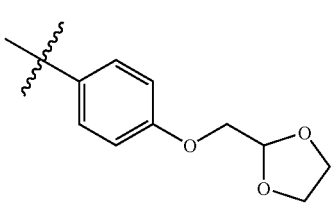 |
| 343 | CH$_2$ | H | CH | O | CH$_3$ | 4-(CH$_3$)$_2$CHCH$_2$O—C$_6$H$_4$ |
| 344 | CH$_2$ | H | CH | O | CH$_3$ | 4-CH$_3$(CH$_2$)$_5$O—C$_6$H$_4$ |
| 345 | CH$_2$ | H | CH | O | CH$_3$ | 4-CH$_3$CH$_2$CH(CH$_3$)O—C$_6$H$_4$ |
| 346 | CH$_2$ | H | CH | O | CH$_3$ | 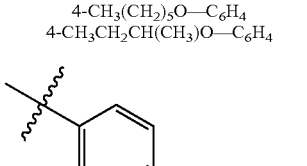 |

Among the compounds of formula (1), preferred are those wherein A is O or O—N=C(CH$_3$); X is H, F or Cl, Y is CH, Z is O, R$^1$ is methyl, and R$^2$ is substituted or unsubstituted aryl.

Particularly preferred are those of formula (1a):

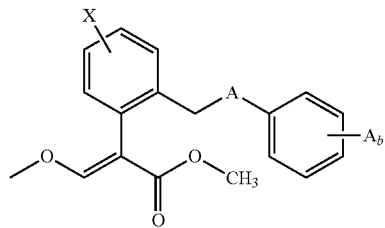

(1a)

wherein,
A is O or O—N=C(CH$_3$);
X represents H, F or Cl;
A$_b$ is at least one group selected from the group consisting of halogens, C$_{1~4}$ haloalkyl, C$_{1~4}$ haloalkenyl, C$_{1~8}$ alkyl, C$_{2~8}$ alkenyl, C$_{2~4}$ alkynyl, C$_{3~6}$ cycloalkyl, C$_{1~8}$ alkoxy, C$_{1~4}$ alkoxy C$_{1~4}$ alkyl, C$_{3~6}$ cycloalkyl C$_{1~4}$ alkyl, C$_{1~4}$ dialkoxy C$_{1~4}$ alkyl, 1,3-dioxolan-2-yl, 1,3-dioxan-2-yl, C$_{2~8}$ alkenyloxy, C$_{2~4}$ alkynyloxy, C$_{3~6}$ cycloalkyl C$_{1~4}$ alkoxy, hydroxy C$_{1~4}$ alkyl, C$_{1~4}$ dialkylamino C$_{1~4}$ alkoxy, at least one N or O-containing C$_{2~5}$ heterocyclo C$_{1~4}$ alkoxy, 2-morpholinoethoxy, 2-(piperidin-1-yl) ethoxy), unsubstituted or substituted N-containing heteroaryl, unsubstituted or substituted amino, and unsubstituted or substituted amino C$_{1~2}$ alkyl.

Specific examples of the compounds of formula (1) include:
(E)-methyl 2-(2-((4-octylphenoxy)methyl)-3-methoxyacrylate;
(E)-methyl 2-(2-((4-(cyclopropylmethoxy)phenoxy)methyl)-4-chlorophenyl)-3-methoxy-acrylate;
(E)-methyl 2-(2-((4-(2-methoxyethoxy)phenoxy)methyl)-4-chlorophenyl)-3-methoxyacrylate;
(E)-methyl 2-(2-((4-(allyloxy)phenoxy)methyl)-4-chlorophenyl)-3-methoxyacrylate;
(E)-methyl 2-(2-((4-(2-methoxyethoxy)phenoxy)methyl)-4-fluorophenyl)-3-methoxyacrylate;
(E)-methyl 2-(2-((4-(allyloxy)phenoxy)methyl)-4-fluorophenyl)-3-methoxyacrylate;
(E)-methyl 2-(2-((4-(1-methylpropaneoxy)phenoxy)methyl)-4-fluorophenyl)-3-methoxy-acrylate;
(E)-methyl 2-(2-((3-(2-morpholinoethoxy)phenoxy)methyl)phenyl)-3-methoxyacrylate;
(E)-methyl 2-(2-((3-(1,3-dioxan-2-yl)phenoxy)methyl)phenyl)-3-methoxyacrylate;
(E)-methyl 2-(2-((4-(allyloxy)phehethyl)phenyl)-3-methoxyacrylate;
(E)-methyl 2-(((({1E}-1-(3-(n-hexyloxy)phenyl)ethylidene)amino)oxy)methyl)phenyl-3-methoxyacrylate;
(E)-methyl 2-(((({1E}-1-(3-(n-cyanomethyloxy)phenyl)ethylidene)amino)oxy)methyl)phenyl-3-methoxyacrylate;
(E)-methyl 2-(2-((3-morpholinophenoxy)methyl)phenyl)-3-methoxyacrylate;
(E)-methyl 2-(2-((3-morpholinophenoxy)methyl)-4-chlorophenyl)-3-methoxyacrylate;
(E)-methyl 2-(2-((3-(piperidin-1-yl)phenoxy)methyl)phenyl)-3-methoxyacrylate;
(E)-methyl 2-(2-((4-(piperidin-1-yl)phenoxy)methyl)phenyl)-3-methoxyacrylate;
(E)-methyl 2-(2-((3-(4-methylpiperizan-1-yl)phenoxy)methyl)phenyl)-3-methoxyacrylate;
(E)-methyl 2-(2-((4-(N-isobutylamino)-2-fluorophenoxy)methyl)phenyl)-3-methoxyacrylate;

(E)-methyl 2-(2-((4-(N-isobutyl-N-methylamino)-2-fluorophenoxy)methyl)phenyl)-3-methoxyacrylate;
(E)-methyl 2-(2-((4-(N-cyclopropylmethylamino)-2-fluorophenoxy)methyl)phenyl)-3-methoxyacrylate;
(E)-methyl 2-(2-((4-(N-cyclopropylmethyl-N-methylamino)-2-fluorophenoxy)methyl)phenyl)-3-methoxyacrylate;
(E)-methyl 2-(2-((3-fluoro-4-(piperidin-1-yl)phenoxy)methyl)phenyl)-3-methoxyacrylate;
(E)-methyl 2-(2-((2-fluoro-4-morpholinophenoxy)methyl)phenyl)-3-methoxyacrylate;
(E)-methyl 2-(2-((3-(morpholinomethyl)phenoxy)methyl)phenyl)-3-methoxyacrylate;
(E)-methyl 2-(2-((3-(N-methyl-N-phenylamino)phenoxy)methyl)-4-chlorophenyl)-3-methoxy-acrylate;
(E)-methyl 2-(2-((3-((4-methylpiperizan-1-yl)methyl)phenoxy)methyl)phenyl)-3-methoxy-acrylate;
(E)-methyl 2-(2-((6-(pyrrolidin-1-yl)pyridin-2-yloxy)methyl)phenyl)-3-methoxyacrylate;
(E)-methyl 2-(2-((6-(piperidin-1-yl)pyridin-2-yloxy)methyl)phenyl)-3-methoxyacrylate;
(E)-methyl 2-(2-((5-(morpholino)pyridin-2-yloxy)methyl)phenyl)-3-methoxyacrylate; and
(E)-methyl 2-(2-((6-(morpholino)pyridin-2-yloxy)methyl)phenyl)-3-methoxyacrylate.

The inventive composition may also comprise physiologically and pharmaceutically acceptable salts of the compound of formula (1) as active ingredients. The pharmaceutically acceptable salts may be non-toxic and water-soluble salts. Representative examples thereof include alkali metal salts such as sodium and potassium salts; alkaline earth metal salts such as magnesium and calcium salts; ammonium salts such as tetramethylammonium salts; amine salts such as triethylamine, methylamine, dimethylamine, cyclopentylamine, benzylamine, phenethylamine, piperidine, monoethanolamine, diethanolamine, tris(hydroxymethyl)-aminomethane, lysine, arginine and N-methyl-D-glucamine salts; inorganic acid salts such as hydrochloric, hydrobromic, hydroiodic, sulfuric, phosphoric and nitric acid salts; organic acid salts such as acetic, lactic, tartaric, benzoic, citric, methanesulfonic, ethanesulfonic, benzenesulfonic, toluenesulfonic, isethionic, glucuronic and gluconic acid salts; hydrates; and solvates such as alcoholates (e.g., ethanolate).

The compound of formula (1) used in the present invention may be prepared by the method described in European Patent Publication No. 278,595. For example, a compound of formula (1a) may be prepared by reacting a compound of formula (2) with a compound of formula (3) in the presence of a base.

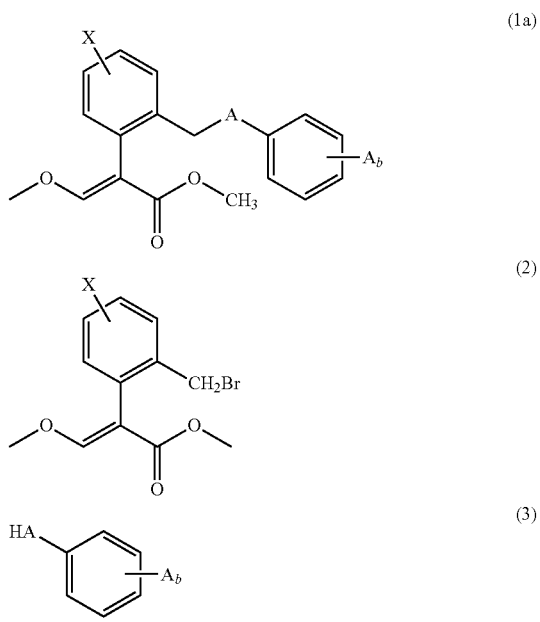

wherein, X, Y, A and $A_b$ have the same meanings as defined above.

Further, the compound of formula (2) used as the starting material in the above reaction may be prepared as shown in the Reaction Scheme 1:

Reaction Scheme 1

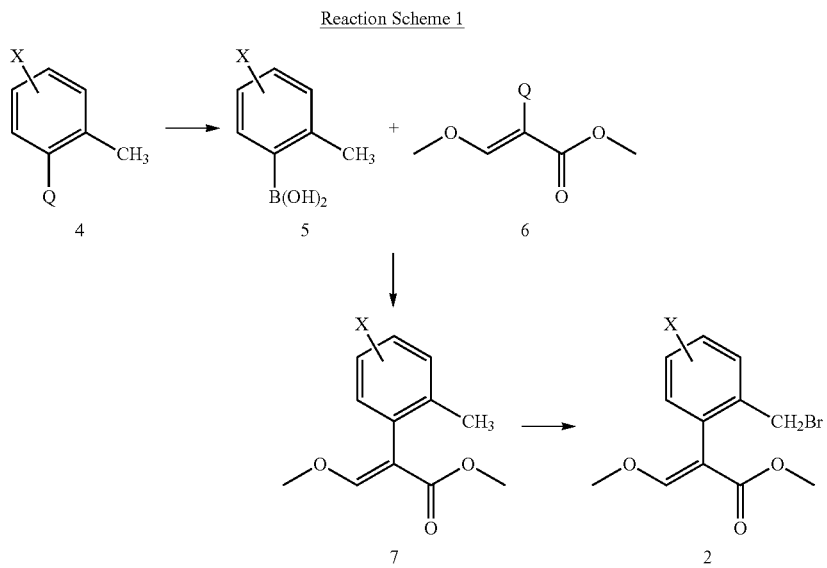

wherein, X has the same meaning as defined above; and Q is a halogen such as iodine, bromine and chorine.

As shown in Reaction Scheme 1, the compound of formula (2) may be prepared by the method comprising the steps of: reacting the aryl halide compound of formula (4) (preferably, Q is iodine or bromine) with triisopropylboronate in the presence of a base such as n-butyl lithium, and treating the resulting mixture with an acidic solution, e.g., hydrochloric acid, to form the compound of formula (5) (see W Li et al., *J. Org. Chem.*, 67, 5394, 2002); reacting the compound of formula (5) with methyl α-halomethoxyacrylate of formula (6) (preferably, Q is iodine or bromine) which is prepared from methyl propionate as a starting material according to the methods disclosed in R. E. Ireland et al., *J. Org. Chem.*, 56, 3572, 1991 and D. M. Hodgson et al., *Synlett*, 32, 1995, in the presence of a palladium catalyst, e.g., Pd(OAc)$_2$ or Pd(PPh$_3$)$_4$ and an inorganic salt, e.g., K$_2$CO$_3$, Na$_2$CO$_3$, K$_2$PO$_4$ or Cs$_2$CO$_3$, to form the compound of formula (7); and treating the compound of formula (7) with N-bromosuccinimide.

A particular compound of formula (2), (E)-methyl-2-(2-bromomethylphenyl)-3-methoxyacrylate (i.e., the compound of formula (2) wherein X is hydrogen) may be prepared by the method disclosed in European Patent Publication No. 278, 595.

The compounds of formula (3) may be also prepared in a conventional manner, and those having O—N═C(CH$_3$) as the A group in particular may be obtained by the method disclosed in Korean Patent Nos. 31195 and 311 96, and those wherein A is oxygen and A$_b$ is amino, by the method disclosed in Hassen, J. et al., *Chemical Review*, 102, 1359, 2002.

In addition, the compound of formula (1a) may be prepared according to the procedure shown in Reaction Scheme 2:

wherein, X, A$_b$ and Q have the same meanings as defined above.

In accordance with Reaction Scheme 2, the compound of formula (1a) may be prepared by the method comprising the steps of: treating the halotoluene compound of formula (8) (preferably, Q is iodine or bromine) with N-bromosuccinimide to form the benzylbromide compound of formula (9); reacting the compound of formula (9) with the phenol compound of formula (3a) to form the compound of formula (10); allowing the compound of formula (10) to react with triisopropylboronate in the presence of a base, e.g., n-butyl lithium and treating the resulting mixture with an acidic solution, e.g., hydrochloric acid, to form the compound of formula (11); and reacting the compound of formula (11) with the compound of formula (6) in the presence of a palladium catalyst, e.g., Pd(OAc)$_2$ and Pd(PPh$_3$)$_4$ and an inorganic salt, e.g., K$_2$CO$_3$, Na$_2$CO$_3$, K$_2$PO$_4$ and Cs$_2$CO$_3$.

The compound of formula (3a) used in the above method may be prepared by a known method, that having an amino group for A$_b$ may be synthesized by the method disclosed in Hassen, J. et al., *Chemical Review*, 102, 1359, 2002 and Wolfe, J. P. et al., *J. Org. Chem.*, 65, 1158, 2000, and that having —NR$^3$R$^4$ for A$_b$ (the compound of formula (3a-1)) may be prepared according to the procedure shown in Reaction Scheme 3.

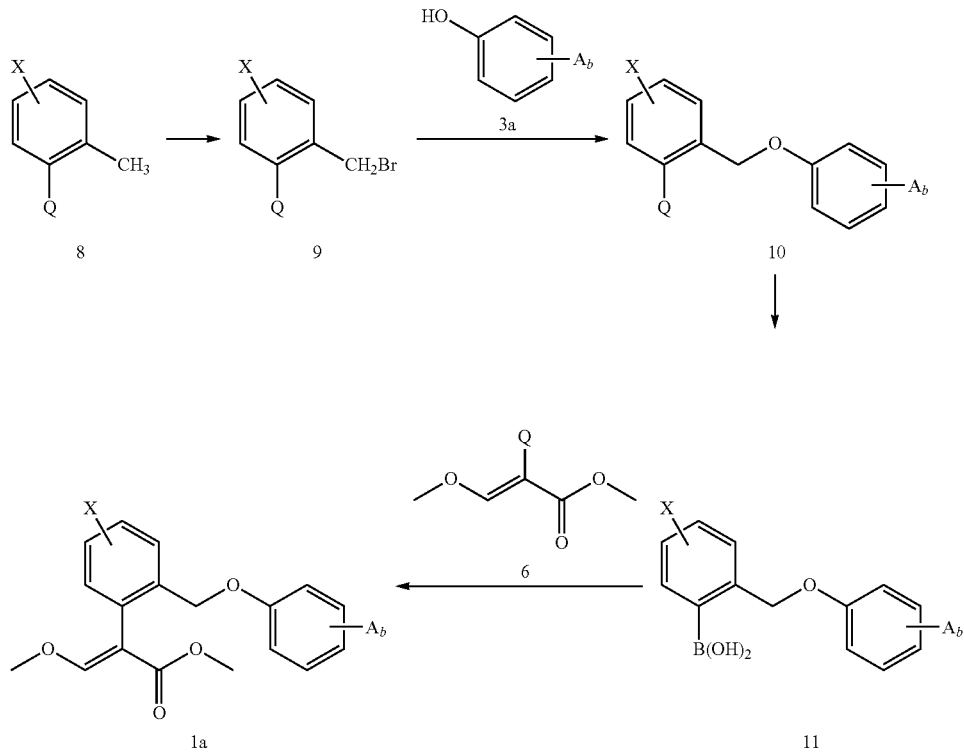

Reaction Scheme 2

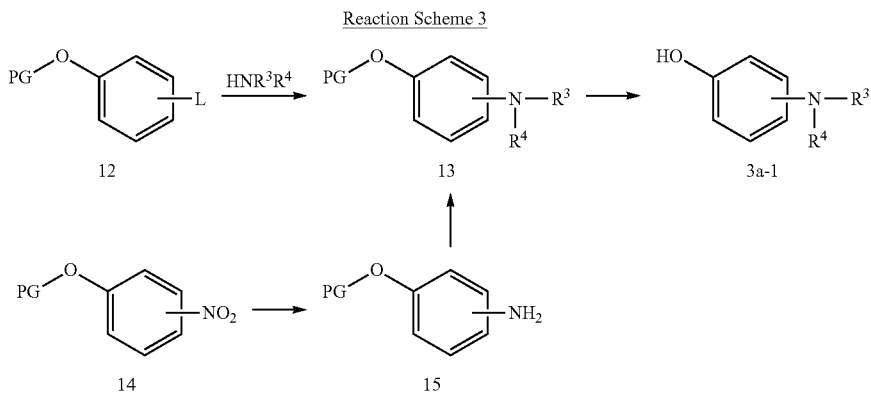

Reaction Scheme 3 wherein, $R^3$ and $R^4$ have the same meanings as defined above; L is a halogen or $OSO_2CF_3$; and PG is methyl, benzyl or trialkylsilyl (e.g., trimethylsilyl, triethylsilyl, triisopropylsilyl or t-butyldimethylsilyl).

That is, the compound of formula (3a-1) may be prepared by amination of the compound of formula (12), followed by deprotection of the compound of formula (13) obtained from the amination.

The amination of the compound of formula (12) may be carried out by a conventional amination method (see Smith, M. B. et al., *Advanced Organic Chemistry*, 5$^{th}$ Ed., pp 850-893, 2001) and the deprotection may be carried out by a conventional deprotection method (see Greene, T. W. et al., *Protective Groups in Organic Synthesis*, 3$^{rd}$ Ed., pp 23-148, 1999). The amination may be carried out in an inert solvent in the presence of a palladium catalyst, a base and a phosphine ligand. Exemplary palladium catalysts include, but are not limited to, palladium (II) acetate, palladium (II) chloride, palladium (II) bromide, dichlorobis(triphenylphosphine) palladium (II), tetrakis(triphenylphosphine) palladium(0) and tris(dibenzylideneacetone) dipalladium(0). Exemplary phosphine ligands include, but are not limited to, 2,2'-bis(diphenylphosphino)-1,1'-binaphthyl (BINAP), tri-o-tolylphosphine, tri-t-butylphosphine, 1,1'-bis(diphenylphosphino) ferrocene, bis[(2-diphenylphosphino)-phenyl]ether (DPEphos), 2-dicyclohexylphosphanyl-2'-dimethylaminobiphenyl, 2-(di-t-butylphosphino) biphenyl, 9,9'-dimethyl-4,6-bis (diphenylphosphino) xanthene (Xanthaphos) and a racemate thereof. Exemplary bases include sodium t-butoxide (t-BuONa) and an inorganic salt (e.g., $K_2CO_3$, $Na_2CO_3$, $K_2PO_4$ or $Cs_2CO_3$). Exemplary inert solvents include 1,4-dioxane, toluene, benzene, acetonitrile, dimethylformamide and tetrahydrofuran. The palladium catalyst and the phosphine ligand may be used in catalytic amounts, preferably in amounts ranging from 0.1 to 10% by mol based on the compound of formula 12. The amination may be carried out at 80 to 150° C. for 3 to 30 minutes under an inert gas such as argon or nitrogen.

As also shown in Reaction Scheme 3, the compound of formula 13 may be prepared by reduction of a nitro group-containing compound of formula 14, followed by an alkylation of the resulting amino-containing compound, i.e., the compound of formula 15.

Further, the compound of formula (3a) having a substituted aminomethyl group ($-CH_2-NR^3R^4$) for $A_b$ (the compound of formula (3a-2)) may be prepared by a method as shown in Reaction Scheme 4.

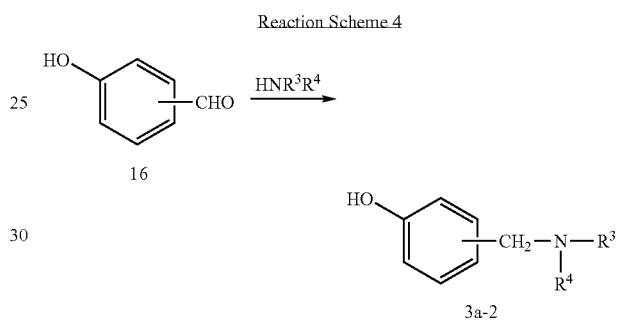

Reaction Scheme 4 wherein, $R^3$ and $R^4$ have the same meanings as defined above.

That is, the compound of formula (3a-2) may be prepared by amination of the aldehyde compound of formula (16) in a conventional manner. The amination of Reaction Scheme 4 may be carried out in an inert solvent in the presence of a reducing agent. Exemplary reducing agents include, but are not limited to, sodium borohydride ($NaBH_4$), sodium cyanoborohydride ($NaBH_3CN$) and sodium triacetoxyborohydride ($NaBH(OAc)_3$).

The compound of formula (1) is used in a pharmaceutical composition for treating or preventing metabolic bone diseases, as an active ingredient, together with pharmaceutically acceptable carriers. Exemplary pharmaceutically acceptable carriers include excipients, disintegrants, sweeting agents, lubricants and flavoring agents. The inventive composition may further comprise other components such as vitamin C for enhancing health, if necessary.

The pharmaceutical composition of the present invention may be formulated in various forms such as a tablet, capsule, powder, granule, and solution such as suspension, emulsion and syrup, and other forms for oral or parenteral administration. The inventive pharmaceutical composition may be administrated in a single dose or in divided doses. In case of the parenteral administration, a typical daily dose of the active ingredient ranges from 0.5 to 5 mg/kg of body weight, preferably 1 to 4 mg/kg of body weight, and in case of oral administration, 5 to 50 mg/kg of body weight, preferably 10 to 40 mg/kg of body weight. However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

In accordance with another aspect of the present invention, there is provided a healthy food or drink composition for treating or preventing metabolic bone diseases such as osteoporosis, comprising the compound of formula (1) as an active ingredient. Exemplary foods and drinks to which the compound of formula (1) may be applied include, but are not limited to, meats, beverages, chocolates, snacks, confectionery, pizza, instant noodles, various noodles, gums, ice creams, alcoholic beverages, and vitamin formulations. In the healthy food or drink composition, the compound of formula (1) may be employed in an amount ranging from 0.1 to 80% by weight of the composition.

The present invention will be described in further detail with reference to Examples. However, it should be understood that the present is not restricted by the specific Examples.

EXAMPLE 1

Preparation of (E)-methyl-2-(2-((4-(cyclopropylmethyl)phenoxy)methyl)-4-chlorophenyl)-3-methoxyacrylate (Compound No. 267)

Step 1)

13.3 ml (0.1 mol) of 2-bromo-5-chlorotoluene was dissolved in 200 ml of anhydrous THF, and 27.7 ml (0.12 mol) of triisopropyl borate was added thereto. After cooling the reaction mixture to −78° C. over a dry ice-acetone bath, 48 ml (0.12 mol) of 2.5 M n-BuLi (in hexane) was added dropwise thereto for 1 hour, the dry ice-acetone bath was removed, and 150 ml of 3 N HCl was added thereto. The resulting mixture was stirred for 1 hour, and the separated water layer was extracted twice with 100 ml portions of ethyl acetate. The organic layers were combined, washed with a brine solution, dried over anhydrous $MgSO_4$, and filtered under a reduced pressure to remove the solvent. The residue was recrystallized from 10% ethyacetate/hexane to obtain 13.8 g (yield 81%) of 4-chloro-2-methylboronic acid as a white solid.

$^1$H NMR (300 MHz, $CDCl_3$) d 8.07 (dd, 1H, J=5.7 Hz, 2.8 Hz), 7.28–7.26 (m, 2H), 2.76 (s, 3H)

Step 2)

13.8 g (80 mmol) of the compound obtained in Step 1, 3.1 g (2.7 mmol) of tetrakis(triphenylphosphine) palladium and 42.7 g (200 mmol) of $K_3PO_4$ were placed successively in a flask, and 450 ml of dioxane and 90 ml of water were added thereto. After adding 16.2 g (67 mmol) of (E)-methyl-2-iodo-3-methoxy-2-propenoate thereto, the mixture was stirred at 90° C. for 22 hours and cooled to room temperature, and 200 ml of ethyl acetate was added thereto. The separated water layer was extracted twice with 50 ml portions of ethyl acetate, and the organic layers were combined, washed with 100 ml of water and 100 ml of a brine solution. The resulting solution was dried over anhydrous $MgSO_4$, and concentrated under a reduced pressure. The concentrate was subjected to column chromatography using a mixture of 10% ethyl acetate/hexane as an eluent to obtain 12.6 g (yield 78%) of (E)-methyl-2-(4-chloro-2-methylphenyl)-3-methoxyacrylate as a solid.

$^1$H NMR (300 MHz, $CDCl_3$) d 7.56 (s, 1H), 7.22–7.14 (m, 2H), 7.03 (d, 1H, J=8.2 Hz), 3.83 (s, 3H), 3.70 (s, 3H), 2.15 (s, 3H)

Step 3)

9.7 g (40 mmol) of the compound obtained in Step 2 was dissolved in 200 ml of carbon tetrachloride, and 0.7 g (4 mmol) of AIBN and 7.9 g (44 mmol) of N-bromosuccinimide were added thereto. The mixture was refluxed for 5 hours, and cooled to room temperature. The reaction mixture was washed with 50 ml of water twice and 50 ml portions of a brine solution, dried over anhydrous $MgSO_4$, and distilled under a reduced pressure to obtain (E)-methyl-2-(2-bromomethyl-4-chlorophenyl)-3-methoxyacrylate containing a small amount of the starting material as an oil.

Step 4)

0.6 g (1.8 mmol) of the compound obtained in Step 3 was dissolved in 5 ml of acetonitrile, 0.5 g (3.6 mmol) of $K_2CO_3$ and 0.27 g (1.8 mmol) of 4-cyclopropylmethoxyphenol were added thereto, the resulting mixture was refluxed for 15 hours, and distilled under a reduced pressure to remove the solvent. To the residue, 30 ml of ethyl acetate was added, the resulting mixture was washed twice with water, dried over anhydrous $MgSO_4$, and concentrated under a reduced pressure. The concentrate was subjected to column chromatography to obtain 0.6 g (yield 85%) of (E)-methyl-2-(2-((4-(cyclopropylmethoxy)phenoxy)methyl)-4-chlorophenyl)-3-methoxyacrylate as a white solid.

$^1$H NMR (300 MHz, $CDCl_3$) d 7.58 (s, 1H), 7.55 (d, J=2.4 Hz, 1H), 7.26 (dd, J=8.1 Hz, 2.1 Hz, 1H), 7.07 (d, J=8.1 Hz, 1H), 6.83 (s, 4H), 4.85 (s, 2H), 3.82 (s, 3H), 3.73 (d, J=7.2 Hz, 2H), 3.69 (s, 3H), 1.27–1.22 (m, 1H), 0.65–0.59 (m, 2H), 0.35–0.30 (m, 2H)

EXAMPLE 2

Preparation of (E)-methyl-2-(2-((4-(2-methoxyethoxy)phenoxy)methyl)-4-chlorophenyl)-3-methoxyacrylate (Compound No. 274)

Step 1)

20.5 g (100 mmol) of 2-bromo-5-chlorotoluene was dissolved in 200 ml of carbon tetrachloride, 0.2 g (1 mmol) of AIBN and 19.6 g (110 mmol) of N-bromosuccinimide were added thereto, the resulting mixture was refluxed for 2 hours and cooled to room temperature. The reaction mixture was washed with 50 ml of water twice and with 50 ml of a brine solution, dried over anhydrous $MgSO_4$, and distilled under a reduced pressure to obtain an oil containing a small amount of the starting material. The oil was dissolved in 20 ml of hexane, and recrystallized at room temperature to obtain 22.7 g (yield 80%) of 2-bromo-1-bromomethyl-5-chlorobenzene.

$^1$H NMR (300 MHz, $CDCl_3$) d 7.50 (d, 1H, J=8.7 Hz), 7.45 (d, 1H, J=2.4 Hz), 7.15 (dd, 1H, J=8.7 Hz, 2.4 Hz), 4.53 (s, 2H)

Step 2)

1.42 g (5 mmol) of the compound obtained in Step 1 was dissolved in 20 ml of acetonitrile, 1.38 g (10 mmol) of $K_2CO_3$ and 0.84 g (5 mmol) of 4-(2-methoxyethoxy)phenol were added thereto, which was refluxed for 15 hours. The reaction mixture was distilled under a reduced pressure to remove the solvent, and 20 ml of ethyl acetate was added thereto. The resulting mixture was washed twice with water, dried over anhydrous $MgSO_4$, and concentrated under a reduced pressure. The concentrate was subjected to column chromatography using 20% ethyl acetate/hexane to obtain 1.76 g (yield 95%) of 1-(2-bromo-5-chlorobenzyloxy)-4-(2-methoxyethoxy)benzene.

Step 3)

In a flask, 1.8 g (4.8 mmol) of the compound obtained in Step 2 was dissolved in 10 ml of anhydrous THF, and 1.34 ml (5.8 mmol) of triisopropyl borate was added thereto. The flask was cooled to −78° C. over a dry ice-acetone bath, 2.3 ml (5.8 mmol) of 2.5 M n-BuLi (in hexane) was added dropwise to the mixture over 15 min. After the reaction mixture was kept for 1 hour, the dry ice-acetone bath was removed, and 5 ml of 2 N HCl was added to the mixture. After stirring the mixture for 1 hour, the water layer was separated and extracted twice with 10 ml portions of ethyl acetate. The organic layers were combined, washed with a brine solution, dried over anhydrous $MgSO_4$, and filtered under a reduced pressure to remove the solvent. The residue was recrystallized from ethyl acetate/hexane to obtain 1.12 g (yield 69%) of 2-((4-(2-methoxyethoxy)phenoxy)methyl)-4-chlorophenylboronic acid.

Step 4)

1.1 g (3.3 mmol) of the compound obtained in Step 3, 0.17 g (0.15 mmol) of tetrakis(triphenylphosphine) palladium and 1.96 g (9.0 mmol) of $K_3PO_4$ were placed in a flask, and 5 ml of dioxane and 1 ml of water were added thereto. After adding 0.73 g (3.0 mmol) of (E)-methyl-2-iodo-3-methoxy-2-propenoate thereto, the resulting mixture was stirred at 90° C. for 22 hours. The mixture was cooled to room temperature, and 10 ml of ethyl acetate was added thereto. The water layer was separated and extracted twice with 10 ml of ethyl acetate, and the organic layers were combined, washed with 20 ml of water and then with 20 ml of a brine solution, dried over anhydrous $MgSO_4$ and concentrated under a reduced pressure. The resulting residue was subjected to column chromatography using 20% ethyl acetate/hexane as an eluent to obtain 0.87 g (yield 71%) of (E)-methyl-2-(2-((4-(2-methoxyethoxy)phenoxy)methyl)-4-chlorophenyl)-3-methoxyacrylate.

$^1$H NMR (300 MHz, $CDCl_3$) d 7.58 (s, 1H), 7.56 (d, J=2.3 Hz, 1H), 7.26 (dd, J=8.1 Hz, 2.1 Hz, 1H), 7.00 (d, J=8.0 Hz, 1H), 6.83 (s, 4H), 4.85 (s, 2H), 4.06 (t, J=6.1 Hz, 2H), 3.82 (s, 3H), 3.73 (t, J=6.1 Hz, 2H), 3.70 (s, 3H), 3.44 (s, 3H)

Similar procedures to Examples 1 and 2 were conducted to obtain the alpha-arylmethoxyacrylate derivatives as shown in Tables 1a to 1l, and the $^1$H-NMR and MS analysis results of the representative compounds obtained are shown in Table 2a to 2c.

TABLE 2a

| Com. No. | $^1$H-NMR ($CDCl_3$, 300 MHz) δ (ppm) | MS (m/e) (M$^+$, int) |
|---|---|---|
| 15 | 7.58 (s, 1H), 7.51~6.88 (m, 8H), 5.15 (s, 2H), 3.97 (t, J = 6.6 Hz, 2H), 3.80 (s, 3H), 3.68 (s, 3H), 2.22 (s, 3H), 1.82~1.73 (m, 2H), 1.58~1.26 (m, 6H), 0.91 (t, J = 6.9 Hz, 3H) | 439 (12), 348 (31), 145 (71), 43 (100) |
| 20 | 7.58 (s, 1H), 7.55~6.91 (m, 8H), 5.15 (s, 2H), 4.14 (t, J = 5.7 Hz, 2H), 3.81 (s, 3H), 3.76~3.72 (m, 4H), 3.68 (s, 3H), 2.81 (t, J = 6.7 Hz, 2H), 2.60~2.57 (m, 4H), 2.22 (s, 3H) | 468 (21), 377 (57), 145 (100), 43 (61) |
| 133 | 7.58 (s, 1H), 7.56~6.85 (m, 8H), 5.33 (s, 1H), 4.96 (s, 2H), 3.81 (s, 3H), 3.69 (s, 3H), 3.31 (s, 6H) | 372 (24), 205 (56), 145 (100), 102 (29) |
| 161 | 7.56 (s, 1H), 7.51 (t, J = 4.1 Hz, 1H), 7.35 (d, J = 8.7 Hz, 2H), 7.34~7.29 (m, 2H), 7.16 (t, J = 4.1 Hz, 1H), 6.86 (d, J = 8.6 Hz, 2H), 5.43 (s, 1H), 4.95 (s, 2H), 4.23 (dd, J = 10.9 Hz, 5.0 Hz, 2H), 3.95 (td, J = 12.3 Hz, 2.2 Hz, 2H), 3.80 (s, 3H), 3.69 (s, 3H), 2.22~2.18 (m, 2H) | 384 (21), 205 (39), 145 (100), 103 (25) |
| 170 | 7.58 (s, 1H), 7.55~7.52 (m, 1H), 7.34~7.27 (m, 4H), 6.91~6.83 (m, 3H), 5.51 (qd, J = 47.7 Hz, 6.4 Hz, 1H), 3.80 (s, 3H), 3.69 (s, 3H), 1.59 (dd, J = 23.9 Hz, 6.4 Hz, 3H) | 344 (31), 145 (100), 130 (22), 102 (37) |
| 172 | 7.57 (s, 1H), 7.56~6.74 (m, 8H), 4.89 (s, 2H), 4.65~4.64 (m, 1H), 3.81 (s, 3H), 3.69 (s, 3H), 1.82~1.56 (m, 8H) | 382 (22), 204 (29), 144 (100), 130 (14), 68 (22), 41 (41) |
| 174 | 7.57 (s, 1H), 7.56~6.79 (m, 8H), 4.90 (s, 2H), 3.81 (s, 3H), 3.69 (s, 3H), 3.64 (d, J = 6.3 Hz, 2H), 2.04~2.01 (m, 1H), 0.99 (d, J = 6.6 Hz, 6H) | 370 (13), 205 (22), 144 (100), 131 (11), 102 (11), 56 (29), 41 (27) |
| 175 | 7.58 (s, 1H), 7.57~6.79 (m, 8H), 4.90 (s, 2H), 4.19~4.03 (m, 1H), 3.81 (s, 3H), 3.69 (s, 3H), 1.67~1.52 (m, 2H), 1.24 (d, J = 6.1 Hz, 3H), 0.96 (t, J = 7.4 Hz, 3H) | 370 (24), 204 (34), 144 (100), 56 (26), 41 (26) |
| 178 | 7.57 (s, 1H), 7.56~6.77 (m, 8H), 5.93~5.82 (m, 1H), 5.17~5.07 (m, 2H), 4.90 (s, 2H), 3.94 (t, J = 6.6 Hz, 2H), 3.81 (s, 3H), 3.69 (s, 3H), 2.40 (q, J = 6.6 Hz, 2H) | 368 (18), 205 (57), 145 (100), 131 (21), 114 (17), 103 (14), 55 (25) |
| 179 | 7.57 (s, 1H), 7.53 (d, J = 6.6 Hz, 1H), 7.34~7.30 (m, 2H), 7.16 (d, J = 6.3 Hz, 1H), 6.82 (s, 4H), 5.12~5.94 (m, 1H), 5.38 (dd, J = 17.4 Hz, 1.5 Hz, 1H), 5.25 (dd, J = 10.5 Hz, 1.2 Hz, 1H), 4.09 (s, 2H), 4.45 (d, J = 5.4 Hz, 2H), 3.81 (s, 3H), 3.68 (s, 3H) | 354 (18), 204 (18), 145 (100), 130 (24), 114 (14), 41 (19) |
| 183 | 7.58 (s, 1H), 7.56~6.80 (m, 8H), 4.90 (s, 2H), 3.98 (q, J = 6.9 Hz, 2H), 3.82 (s, 3H), 3.69 (s, 3H), 1.38 (t, J = 6.9 Hz, 3H) | 342 (25), 205 (21), 145 (100) |
| 192 | 7.87 (s, 1H), 7.57~6.77 (m, 8H), 4.90 (s, 2H), 3.85 (t, J = 6.6 Hz, 2H), 3.80 (s, 3H), 3.69 (s, 3H), 1.83~1.71 (m, 2H), 1.01 (t, J = 7.5 Hz, 3H) | 356 (24), 205 (64), 145 (100), 102 (43) |

TABLE 2b

| | | |
|---|---|---|
| 197 | 7.58 (s, 1H), 7.57~7.09 (m, 5H), 6.51~6.46 (m, 3H), 5.92~5.71 (m, 1H), 5.05~4.95 (m, 2H), 4.93 (s, 2H), 3.91 (t, J = 6.5 Hz, 2H), 3.82 (s, 3H), 3.70 (s, 3H), 2.11~2.00 (m, 2H), 1.81~1.71 (m, 2H), 1.55~1.26 (m, 6H) | 424 (21), 205 (71), 144 (100), 130 (42), 102 (51) |
| 201 | 7.58 (s, 1H), 7.56~7.53 (m, 1H), 7.34~7.28 (m, 2H), 7.18~7.09 (m, 2H), 6.49~6.47 (m, 3H), 4.93 (s, 2H), 3.91 (t, J = 6.6 Hz, 2H), 3.82 (s, 3H), 3.69 (s, 3H), 1.77~1.70 (m, 2H), 1.43~1.26 (m, 8H), 0.89 (t, J = 6.3 Hz, 3H) | 412 (13), 312 (48), 144 (100), 102 (44) |
| 205 | 7.59 (s, 1H), 7.54~6.86 (m, 8H), 5.75~5.54 (m, 1H), 4.98 (s, 2H ), 3.82 (s, 3H), 3.68 (s, 3H), 2.55~2.20 (m, 2H), 1.70 (t, J = 18.9 Hz, 3H) | 408 (24), 205 (100), 130 (47), 115 (30), 102 (26) |
| 206 | 7.60 (s, 1H), 7.59~6.85 (m, 8H), 5.97~5.79 (m, 1H), 4.97 (s, 2H), 3.81 (s, 3H), 3.69 (s, 3H), 3.15~2.68 (m, 2H), 2.18 (s, 3H) | 386 (21), 205 (55), 145 (100), 130 (21) |
| 211 | 7.61 (s, 1H), 7.60~6.49 (m, 8H), 6.18~5.91 (m, 1H), 5.31 (dd, J = 11.4 Hz, 7.0 Hz, 2H), 4.94 (s, 2H), 4.46 (t, J = 1.6 Hz, 2H), 3.82 (s, 3H), 3.69 (s, 3H) | 354 (35), 204 (41), 144 (100), 130 (30), 102 (45), 41 (67) |
| 215 | 7.58 (s, 1H), 7.57~6.48 (m, 8H ), 4.92 (s, 2H), 3.83 (s, 3H), 3.80~3.70 (m, 2H), 3.68 (s, 3H), 0.54~0.41 (m, 5H) | 368 (75), 205 (65), 144 (100), 129 (35), 102 (35) |
| 217 | 7.59 (s, 1H), 7.58~6.48 (m, 8H), 5.58~5.41 (m, 1H), 4.93 (s, 2H, 4.42 (d, J = 6.8 Hz, 2H), 3.81 (s, 3H), 3.69 (s, 3H), 1.75 (d, J = 18.6 Hz, 6H) | 382 (18), 214 (22), 205 (79), 144 (100), 102 (26), 69 (16) |
| 219 | 7.59 (s, 1H), 7.58~6.47 (m, 8H), 4.93 (s, 2H), 3.82 (s, 3H), 3.69 (s, 3H), 3.67 (d, J = 6.6 Hz, 2H), 2.09~2.01 (m, 1H), 1.00 (d, J = 6.6 Hz, 6H) | 370 (55), 205 (48), 144 (100), 130 (22), 102 (32) |
| 220 | 7.58 (s, 1H), 7.57~6.47 (m, 8H), 4.93 (s, 2H), 3.91 (t, J = 6.6 Hz, 2H), 3.82 (s, 3H), 3.69 (s, 3H, 1.79~1.25 (m, 8H), 0.90 (t, J = 6.6 Hz, 3H) | 398 (56), 204 (46), 144 (100), 130 (14), 102 (17), 43 (21) |
| 221 | 7.58 (s, 1H), 7.57~6.46 (m, 8H, 4.93 (s, 2H), 4.37~4.21 (m, 1H), 3.81 (s, 3H), 3.69 (s, 3H), 1.81~1.64 (m, 2H), 1.26 (d, J = 6.2 Hz, 3H), 0.95 (t, J = 7.4 Hz, 3H) | 370 (46), 204 (39), 144 (100), 102 (28) |
| 222 | 7.60 (s, 1H), 7.59~6.47 (m, 8H), 4.96 (s, 2H), 4.83~4.72 (m, 1H), 3.83 (s, 3H), 3.72 (s, 3H), 1.92~1.59 (m, 8H) | 382 (47), 205 (69), 144 (100), 102 (24) |
| 234 | 7.58 (s, 1H), 7.56~6.46 (m, 8H), 4.93 (s, 2H), 4.07 (t, J = 5.7 Hz, 2H), 3.81 (s, 3H), 3.72 (t, J = 4.9 Hz, 4H), 3.69 (s, 3H), 2.77 (t, J = 5.7 Hz, 2H), 2.56 (t, J = 4.8 Hz, 4H) | 427 (14), 100 (100), 55 (25), 41 (26) |

TABLE 2c

| | | |
|---|---|---|
| 262 | 8.45 (s, 1H), 8.30~6.01 (m, 7H), 4.92 (s, 2H), 4.57 (s, 2H, 3.80 (s, 3H), 3.70 (s, 3H), 2.96 (br s, 1H) | 362 (21), 238 (41), 178 (100), 136 (38), 101 (37) |
| 264 | 7.58 (s, 1H), 7.56 (d, J = 2.4 Hz, 1H), 7.27 (dd, J = 8.1 Hz, 2.0 Hz, 1H), 7.08 (d, J = 8.1 Hz, 1H), 6.82 (s, 4H), 6.17~5.91 (m, 1H), 5.38 (dd, J = 17.1 Hz, 1.6 Hz, 1H), 5.26 (dd, J = 10.2 Hz, 1.6 Hz, 1H), 4.85 (s, 2H), 4.47 (td, J = 5.3 Hz, 1.6 Hz, 2H), 3.83 (s, 3H) 3.70 (s, 3H) | 388 (22), 239 (67), 178 (75), 136 (43), 41 (100) |
| 267 | 7.58 (s; 1H), 7.55 (d, J = 2.4 Hz, 1H), 7.26 (dd, J = 8.1 Hz, 2.1 Hz, 1H), 7.07 (d, J = 8.1 Hz, 1H), 6.83 (s, 4H), 4.85 (s, 2H), 3.82 (s, 3H), 3.73 (d, J = 7.2 Hz, 2H), 3.69 (s, 3H), 0.64~0.35 (m, 5H) | 402 (42), 239 (60), 178 (100), 136 (34), 55 (43) |
| 269 | 7.57 (s, 1H), 7.55 (d, J = 2.4 Hz, 1H), 7.26 (dd, J = 8.1 Hz, 2.0 Hz, 1H), 7.08 (d, J = 8.0 Hz, 1H), 6.83 (s, 4H), 5.51~5.34 (m, 1H), 4.84 (s, 2H), 4.52 (d, J = 5.3 Hz, 2H), 3.82 (s, 3H), 3.70 (s, 3H, 1.56 (d, J = 6.4 Hz, 6H) | 416 (41), 239 (54), 178 (100) |
| 271 | 7.58 (s, 1H), 7.56 (d, J = 2.3 Hz, 1H), 7.27 (dd, J = 8.0 Hz, 2.1 Hz, 1H), 7.09 (d, J = 8.0 Hz, 1H), 6.81 (s, 4H), 4.85 (s, 2H), 3.89 (t, J = 6.9 Hz, 2H), 3.82 (s, 3H), 3.69 (s, 3H), 1.78~1.26 (m, 8H), 0.89 (t, J = 4.1 Hz, 3H) | 432 (21), 239 (52), 179 (100), 145 (42), 43 (84) |
| 274 | 7.58 (s, 1H), 7.56 (d, J = 2.3 Hz, 1H), 7.26 (dd, J = 8.1 Hz, 2.1 Hz, 1H), 7.00 (d, J = 8.0 Hz, 1H), 6.83 (s, 4H), 4.85 (s, 2H), 4.06 (t, J = 6.1 Hz, 2H), 3.82 (s, 3H), 3.73 (t, J = 6.1 Hz, 2H), 3.70 (s, 3H), 3.44 (s, 3H) | 406 (16), 239 (69), 179 (100), 136 (40), 59 (43) |
| 319 | 7.58 (s, 1H), 7.34~6.46 (m, 7H), 4.86 (s, 2H), 4.37~4.21 (m, 1H), 3.82 (s, 3H), 3.70 (s, 3H), 1.81~1.64 (m, 2H), 1.26 (d, J = 6.2 Hz, 3H), 0.95 (t, J = 7.4 Hz, 3H) | 388 (18), 223 (100), 163 (75), 59 (41) |

EXAMPLE 3

Preparation of (E)-methyl-2-[2-((3-morpholinophenoxy)methyl)-4-chlorophenyl]-3-methoxyacrylate (Compound No. 386)

Step 1)

Method 1

526 mg (2.0 mmol) of 1-(benzyloxy)-3-bromobenzene, 209 μl (2.4 mmol) of morpholine, 283 mg (2.8 mmol) of sodium t-butoxide, 9 mg (0.005 mmol) of tris(dibenzylidine acetone)dipalladium(0) and 19 mg (0.015 mmol) of (±)-BINAP were placed in a flask, 5 ml of toluene was added thereto, and the mixture was stirred at 80° C. for 20 hours. The reaction mixture was cooled to room temperature, 20 ml of ethyl acetate was added thereto, and filtered through Cellite. The resulting filtrate was concentrated under a reduced pressure, and the residue was subjected to column chromatography using 30% ethyl acetate/hexane as an eluent to obtain 430 mg (yield 80%) of 4-(3-(benzyloxy)phenyl)morpholine.

Method 2

The procedure of Method 1 was repeated except for conducting the reaction at 120° C. for 10 min in an air-tighten microwave reactor to obtain 450 mg (yield 85%) of 4-(3-(benzyloxy)phenyl)morpholine.

$^1$H NMR (300 MHz, CDCl$_3$) δ 7.44-7.32 (m, 5H), 7.18 (t, 1H, J=8.7 Hz), 6.55–6.53 (m, 3H), 5.04 (s, 2H), 3.84 (t, 4H, J=4.7 Hz), 3.14 (t, 4H, J=4.9 Hz)

Step 2)

400 mg (1.4 mmol) of the compound obtained in Step 1 was dissolved in a mixture of 10 ml of methanol and 5 ml of ethyl acetate, and 32 mg of 10% palladium/carbon was added thereto. The mixture was placed in a hydrogenation reactor, kept under a hydrogen pressure of 30 to 40 psi for 36 hours, filtered through Cellite, and concentrated under a reduced pressure. The resulting residue was subjected to column chromatography using 5% methanol/methylene chloride as an eluent to obtain 240 mg (yield 80%) of 3-morpholinophenol as a solid form.

M.P.: 116-118° C.;

$^1$H NMR (300 MHz, CDCl$_3$) δ 7.13 (t, 1H, J=8.3 Hz), 6.50 (dd, 1H, J=8.3, 2.5 Hz), 6.40–6.32 (m, 2H), 4.73 (s, 1H), 3.85 (t, 4H, J=4.8 Hz), 3.15 (t, 4H, J=4.8 Hz);

MS (EI) M+ calc. 179.0946 for $C_{10}H_{13}NO_2$. found 179.

Step 3)

58 mg (0.42 mmol) of (E)-methyl-2-(2-bromomethyl-4-chloro)phenyl-3-methoxyacrylate was dissolved in 2 ml of acetonitrile, 110 mg (0.84 mmol) of $K_2CO_3$ and 50 mg (0.28 mmol) of 3-morpholinophenol were added thereto, and the mixture was refluxed for 15 hours. The reaction mixture was distilled under a reduced pressure to remove the solvent, and 10 ml of ethyl acetate was added thereto. The resulting mixture was washed twice with water, dried over anhydrous $MgSO_4$, and concentrated under a reduced pressure. The concentrate was subjected to column chromatography using 20% ethyl acetate/hexane as an eluent to obtain 70 mg (yield 60%) of (E)-methyl-2-[2-((3-morpholinophenoxy)methyl)-4-chlorophenyl]-3-methoxyacrylate as an oil.

$^1$H NMR (300 MHz, $CDCl_3$) δ 7.58 (s, 1H), 7.56-7.09 (m, 4H), 6.54-6.39 (m, 3H), 4.95 (s, 2H), 3.87-3.83 (m, 4H), 3.81 (s, 3H), 3.68 (s, 3H), 3.07-3.02 (m, 4H);

MS (EI) M+ calc. 417.1343 for $C_{22}H_{24}ClNO_5$. found 417.

EXAMPLE 4

Preparation of (E)-methyl-2-[2-((3-(piperidin-1-yl)phenoxy)methyl)phenyl]-3-methoxyacrylate (Compound No. 388)

Step 1)

10.91 g (100 mmol) of 3-aminophenol was dissolved in 100 ml of toluene, and 18.5 g (220 mmol) of sodium bicarbonate and 16.0 ml (110 mmol) of 1,5-dibromopentane were added thereto, followed by refluxing the resulting mixture for 17 hours. The reaction mixture was cooled to room temperature, and 100 ml of water and 100 ml of ethyl acetate were added thereto. The water layer was separated, extracted twice with 100 ml portions of ethyl acetate, and the organic layers were combined, dried over anhydrous $MgSO_4$, and concentrated under a reduced pressure. The concentrate was subjected to column chromatography using 20% ethyl acetate/hexane as an eluent to obtain 12.9 g (yield 73%) of 3-(piperidin-1-yl)phenol as a solid.

M.P.: 112-114° C.;

$^1$H NMR (300 MHz, $CDCl_3$) δ 7.09 (t, 1H, J=7.9 Hz), 6.52 (dd, 1H, J=8.3, 2.3 Hz), 6.41 (t, 1H, J=2.3 Hz), 6.26 (dd, 1H, J=8.2, 2.4 Hz), 4.60 (s, 1H), 3.17-3.12 (m, 4H), 1.69-1.55 (m, 6H);

MS (EI) M+ calc. 177.1154 for $C_{10}H_{15}NO$. found 177.

Step 2)

96 mg (0.33 mmol) of (E)-methyl-2-(2-bromomethyl)phenyl-3-methoxyacrylate was dissolved in 2 ml of acetonitrile, and 58 mg (0.42 mmol) of $K_2CO_3$ and 50 mg (0.28 mmol) of the compound obtained in Step 1 were added thereto, followed by refluxing the mixture for 15 hours. The reaction mixture was distilled under a reduced pressure to remove the solvent, and 10 ml of ethyl acetate was added thereto. The resulting mixture was washed twice with water, dried over anhydrous $MgSO_4$, and concentrated under a reduced pressure. The residue was subjected to column chromatography using 20% ethyl acetate/hexane chloride as an eluent to obtain 56 mg (yield 52%) of (E)-methyl-2-[2-((3-(piperidin-1-yl)phenoxy)methyl)phenyl]-3-methoxyacrylate as a white solid.

M.P.: 64-66° C.;

$^1$H NMR (300 MHz, $CDCl_3$) δ 7.58 (s, 1H), 7.53-7.06 (m, 5H), 6.55-6.34 (m, 3H), 4.93 (s, 2H), 3.81 (s, 3H), 3.69 (s, 3H), 3.15-3.10 (m, 4H), 1.68-1.54 (m, 6H);

MS (EI) M+ calc. 381.194 for $C_{23}H_{27}NO_4$. found 381 (10, M+), 205 (11), 145 (36), 43 (100).

EXAMPLE 5

Preparation of (E)-methyl-2-[2-((4-(N-isobutylamino)-2-fluorophenoxy)methyl)phenyl]-3-methoxyacrylate (Compound No. 425) and (E)-methyl-2-[2-((4-(N-isobutyl-N-methylamino)-2-fluorophenoxy)methyl)phenyl]-3-met hoxyacrylate (Compound No. 426)

Step 1)

1.2 g (3.6 mmol) of (E)-methyl-2-(2-bromomethyl)phenyl-3-methoxyacrylate was dissolved in 20 ml of acetonitrile, 1.0 g (7.2 mmol) of $K_2CO_3$ and 0.57 g (3.6 mmol) of 2-fluoro-4-nitrophenol were added thereto, followed by refluxing the mixture for 15 hours. The reaction mixture was distilled under a reduced pressure to remove the solvent, 50 ml of ethyl acetate was added thereto. The resulting mixture was washed twice with water, dried over anhydrous $MgSO_4$, and concentrated under a reduced pressure. The residue was subjected to column chromatography using 30% ethyl acetate/hexane as a eluent to obtain 1.07 g (yield 82%) of (E)-methyl-2-[2-((2-fluoro-4-nitrophenoxy)methyl)phenyl]-3-methoxyacrylate as a white solid.

Step 2)

1.0 g (2.7 mmol) of the compound obtained in Step 1 was dissolved in a mixture of 5 ml of methanol and 5 ml of ethyl acetate, and 200 mg of 10% palladium/carbon was added thereto. The resulting mixture was placed in a hydrogenation reactor, and hydrogen gas was introduced therein with stirring the mixture for 18 hours. The reaction mixture was filtered through Cellite, and concentrated under a reduced pressure. The residue was subjected to column chromatography using 40% ethyl acetate/hexane as an eluent to obtain 0.84 g (yield 92%) of (E)-methyl-2-[2-((2-fluoro-4-aminophenoxy)methyl)phenyl]-3-methoxyacrylate.

Step 3)

150 mg (0.45 mmol) of the compound obtained in Step 2 was dissolved in 2 ml of methylene chloride, 134 mg (0.63 mmol) of $NaBH(OAc)_3$ and 41 μl (0.45 mmol) of isobutyl aldehyde were added thereto. After stirring at room temperature for 6 hours, the reaction mixture was treated with a saturated sodium bicarbonate, and the water layer was separated, and extracted twice with 10 ml portions of methylene chloride. The organic layers were combined, dried over anhydrous $MgSO_4$, and concentrated under a reduced pressure. The residue was subjected to column chromatography using 20% ethyl acetate/hexane as an eluent to obtain 103 mg (yield 60%) of (E)-methyl-2-[2-((4-(N-isobutylamino)-2-fluorophenoxy)methyl)phenyl]-3-methoxyacrylate as an oil.

$^1$H NMR (300 MHz, $CDCl_3$) δ 7.59 (s, 1H), 7.58-7.56 (m, 1H), 7.34-7.29 (m, 2H), 7.16-7.13 (m, 1H), 6.76-6.70 (m, 1H), 6.38-6.21 (m, 2H), 4.90 (s, 2H), 3.79 (s, 3H), 3.68 (s, 3H), 3.54 (bs, 1H), 2.83 (d, J=6.6, 2H), 1.88-1.79 (m, 1H), 0.96-0.94 (m, 6H)

Step 4)

70 mg (0.18 mmol) of the compound obtained in Step 3 was dissolved in 1.5 ml of methylene chloride, and 57 mg (0.27 mmol) of $NaBH(OAc)_3$ and 30 μl (0.40 mmol) of formaldehyde were added thereto. After stirring at room temperature for 22 hours, the reaction mixture was treated with a saturated sodium bicarbonate aqueous solution, and the water layer was separated and extracted twice with 10 ml of methylene chloride. The organic layers were combined, dried over anhydrous MgSO$_4$, and concentrated under a reduced pressure. The residue was subjected to column chromatography using 20% ethyl acetate/hexane as an eluent to obtain 50 mg (yield 73%) of (E)-methyl-2-[2-((4-(N-isobutyl-N-methylamino)-2-fluorophenoxy)methyl)phenyl]-3-methoxyacrylate as an oil.

$^1$H NMR (300 MHz, CDCl$_3$) δ 7.60 (s, 1H), 7.59–7.57 (m, 1H), 7.34–7.30 (m, 2H), 7.16–7.13 (m, 1H), 6.82–6.76 (m, 1H), 6.45–6.23 (m, 2H), 4.91 (s, 2H), 3.80 (s, 3H), 3.68 (s, 3H), 2.98 (d, J=7.2, 2H), 2.86 (s, 3H), 2.03–1.94 (m, 1H), 0.91–0.88 (m, 6H)

EXAMPLE 6

Preparation of (E)-methyl-2-[2-((3-(morpholinomethyl)phenoxy)-methyl)phenyl]-3-methoxyacrylate (Compound No. 404)

Step 1)

1.2 g (4.0 mmol) of (E)-methyl-2-(2-bromomethyl)phenyl-3-methoxyacrylate was dissolved in 20 ml of acetonitrile, 1.11 g (8.0 mmol) of K$_2$CO$_3$ and 0.59 g (4.8 mmol) of 3-hydroxybenzaldehyde were added thereto, followed by refluxing the mixture for 15 hours. The reaction mixture was distilled under a reduced pressure to remove the solvent, and 50 ml of ethyl acetate was added thereto. The resulting mixture was washed twice with water, dried over anhydrous MgSO$_4$, and concentrated under a reduced pressure. The residue was subjected to column chromatography using 30% ethyl acetate/hexane as an eluent to obtain 0.98 g (yield 75%) of (E)-methyl-2-[2-((3-formylphenoxy)methyl)phenyl]-3-methoxyacrylate as an oil.

Step 2)

326 mg (1.0 mmol) of the compound obtained in Step 1 was dissolved in 5 ml of methylene chloride, and 297 mg (1.4 mmol) of NaBH(OAc)$_3$ and 87 μl (1.0 mmol) of morpholine were added thereto. After stirring at room temperature for 4 hours, the reaction mixture was treated with a saturated sodium bicarbonate aqueous solution, and the water layer was separated, and extracted twice with 20 ml portions of methylene chloride. The organic layers were combined, dried over anhydrous MgSO$_4$, and concentrated under a reduced pressure. The residue was subjected to column chromatography using 3% methanol/chloroform as an eluent to obtain 385 mg (yield 97%) of (E)-methyl-2-[2-((3-(morpholinomethyl)phenoxy)methyl)phenyl]-3-methoxyacrylate as an oil.

$^1$H NMR (300 MHz, CDCl$_3$) δ 7.57 (s, 1H), 7.54–7.51 (m, 1H), 7.31–7.28 (m, 2H), 7.17–7.14 (m, 2H), 6.89–6.86 (m, 2H), 6.80–6.79 (m, 1H), 4.95 (s, 2H), 3.78 (s, 3H), 3.68 (s, 3H), 3.65–3.61 (m, 4H), 3.44 (m, 2H), 2.44–2.34 (m, 4H)

EXAMPLE 7

Preparation of (E)-methyl-2-[2-((6-(pyrrolidin-1-yl)pyridin-2-yloxy)-methyl)phenyl]-3-methoxyacrylate (Compound No. 415).

Step 1)

Method 1

In a dried microwave reactor, 526 mg (2.0 mmol) of 2-(benzyloxy)-6-bromopyridine and 1.70 ml (20 mmol) of pyrrolidine were placed, and the mixture was reacted using microwave at 150° C. for 10 min. The reaction mixture was mixed with 20 ml of water, extracted twice with 100 ml portions of ethyl acetate, and the organic layer was separated dried over anhydrous and kept under a reduced pressure to remove the solvent. The residue thus obtained was subjected to column chromatography using 10% ethyl acetate/hexane as an eluent to obtain 485 mg (yield 95%) of 2-(benzyloxy)-6-(pyrrolidin-1-yl)pyridine.

Method 2

In a dried microwave reactor into which an argon gas was introduced, 526 mg (2.0 mmol) of 2-(benzyloxy)-6-bromopyridine, 200 μl (2.4 mmol) of pyrrolidine, 283 mg (2.8 mmol) of sodium t-butoxide, 9 mg (0.005 mmol) of tris(dibenzylideneacetone)dipalladium(O) (0.5 mol % of Pd), 19 mg (0.015 mmol, 1.5 mol %) of (±)-BINAP and 3 ml of toluene were placed, followed by stirring and reacting the mixture using microwave at 120° C. for 10 min. The reaction mixture was diluted with 20 ml of ethyl acetate, filtered through Cellite, and kept under a reduced pressure to remove the solvent. The residue was subjected to column chromatography using 10% ethyl acetate/hexane as an eluent to obtain 470 mg (yield 92%) of 2-(benzyloxy)-6-(pyrrolidin-1-yl)pyridine.

$^1$H NMR (300 MHz, CDCl$_3$) δ 7.48–7.23 (m, 6H), 6.03–5.99 (m, 1H), 5.89–5.85 (m, 1H), 5.36 (s, 2H), 3.45–3.39 (m, 4H), 2.00–1.93 (m, 4H);

MS (EI) M$^+$ calc. 164.095 for C$_9$H$_{12}$N$_2$O. found 254 (23, M$^+$), 163 (52), 91 (100), 70 (40), 65 (40).

Step 2)

450 mg (1.7 mmol) of the compound obtained in Step 1 was dissolved in a mixture of 5 ml of methanol and 5 ml of ethyl acetate, and 30 mg of 10% palladium/carbon was added thereto. The resulting mixture was placed in a hydrogenation reactor and hydrogen gas was introduced therein with stirring the mixture at room temperature for 18 hours. The reaction mixture was filtered through Cellite, and concentrated under a reduced pressure. The residue was subjected to column chromatography using 50% ethyl acetate/hexane as an eluent to obtain 260 mg (yield 92%) of 6-pyrrolidin-1-yl)pyridin-2-ol.

M.P.: 154-158° C.;

$^1$H NMR (300 MHz, CDCl$_3$) δ 7.26 (td, 1H, J=8.7, 0.8 Hz), 5.75–5.70 (m, 1H), 5.25–5.21 (m, 1H), 4.65 (s, 1H), 3.45–3.39 (m, 4H), 2.00–1.93 (m, 4H);

MS (EI) M$^+$ calc. 164.095 for C$_9$H$_{12}$N$_2$O. found 164 (52, M$^+$), 135 (45), 70 (85), 66 (28), 43 (100).

Step 3)

In a dried reactor, 63 mg (0.46 mmol) of K$_2$CO$_3$ and 50 mg (0.30 mmol) of the compound obtained in Step 2 were added to 4 ml of acetonitrile. The resulting mixture was stirred for 20 min, and 104 mg (0.36 mmol) of (E)-methyl-2-(2-bromomethyl)phenyl)-3-methoxy acrylate was added thereto. The resulting mixture was refluxed for 16 hours, cooled, distilled under a reduced pressure to remove the solvent, and then 10 ml of ethyl acetate was added thereto. The organic layer was separated, washed twice with water, dried over anhydrous MgSO$_4$, and concentrated under a reduced pressure. The residue was subjected to column chromatography using 30% ethyl acetate/hexane as an eluent to obtain 70 mg (yield 64%) of (E)-methyl-2-[2-((6-(pyrrolidin-1-yl)pyridin-2-yloxy)methyl)phenyl]-3-methoxyacrylate.

$^1$H NMR (300 MHz, CDCl$_3$) δ 7.58 (s, 1H), 7.56–7.13 (m, 5H), 5.97–5.25 (m, 2H), 5.25 (s, 2H), 3.79 (s, 3H), 3.68 (s, 3H), 3.43–3.36 (m, 4H), 2.04–1.92 (m, 4H);

MS (EI) M$^+$ calc. 368.1736 for C$_{21}$H$_{24}$N$_2$O$_4$. found 368 (31, M$^+$), 205 (44), 163 (46), 145 (100), 103 (36), 40 (74).

Similar procedures to Examples 3 to 7 were conducted to obtain various alpha-arylmethoxyacrylate derivatives, and the $^1$H-NMR and MS analysis results of the representative compounds thus obtained were shown in Tables 3a to 3n.

TABLE 3a

| Com. No. | structure | ¹H NMR (CDCl₃, TMS) δ (ppm) | MS (m/z, relative intensity) | mp (° C.) |
| --- | --- | --- | --- | --- |
| 347 | 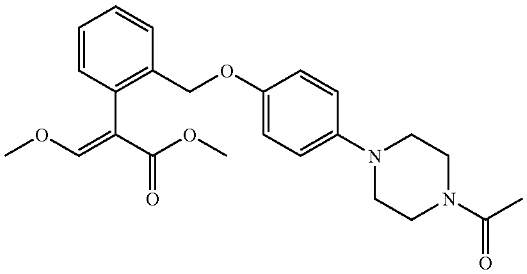 | 7.57 (s, 1H), 7.54~7.51 (m, 1H), 7.36~7.33 (m, 1H), 7.31~7.26 (m, 1H), 7.18~7.15 (m, 1H), 6.85~6.81 (m, 4H), 4.91 (s, 2H), 3.81 (s, 3H), 3.77~3.73 (m, 2H), 3.69 (s, 3H), 3.61~3.58 (m, 2H), 3.05~2.99 (m, 4H), 2.13 (s, 3H) | | |
| 348 | 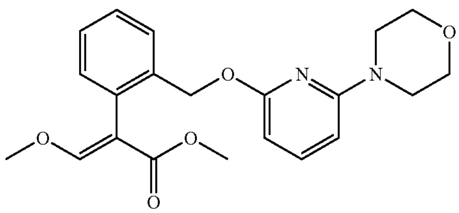 | 7.59 (s, 1H), 7.53~7.26 (m, 5H), 6.14~6.10 (m, 2H), 5.21 (s, 2H), 3.81~3.79 (m, 4H), 3.77 (s, 3H), 3.67 (s, 3H), 3.44~3.41 (m, 4H) | 384 (34, M⁺), 205 (41), 179 (33), 145 (100), 130 (29), 103 (29) | |
| 349 | 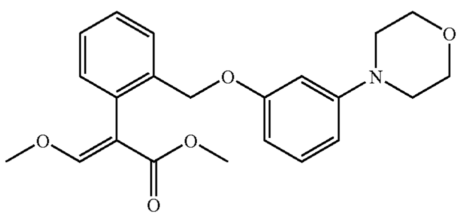 | 7.58 (s, 1H), 7.56~7.09 (m, 5H), 6.54~6.39 (m, 3H), 4.95 (s, 2H), 3.87~3.83 (m, 4H), 3.81 (s, 3H), 3.68 (s, 3H), 3.07~3.02 (m, 4H) | | |
| 350 | 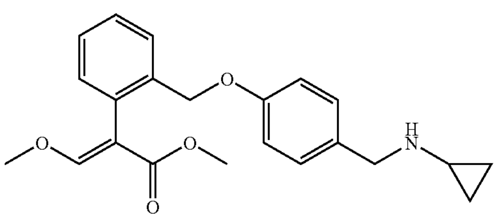 | 7.58 (s, 1H), 7.56~7.53 (m, 1H), 7.35~7.27 (m, 2H), 7.19~7.12 (m, 3H), 6.85~6.81 (m, 2H), 4.95 (s, 2H), 3.81 (s, 3H), 3.69 (s, 3H), 3.57 (s, 2H), 1.78~1.69 (m, 1H), 0.88~0.85 (m, 2H), 0.39~0.29 (m, 2H) | | |
| 351 | 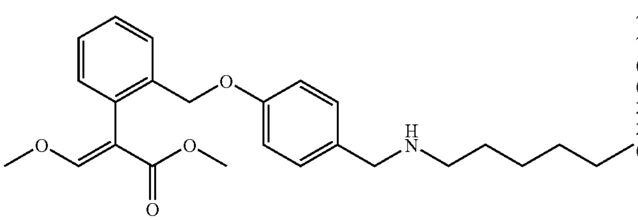 | 7.57 (s, 1H), 7.65~7.52 (m, 1H), 7.34~7.26 (m, 2H), 7.23~7.13 (m, 3H), 6.85~6.81 (m, 2H), 4.93 (s, 2H), 3.80 (s, 3H), 3.69 (s, 3H), 2.34 (t, J = 6.7, 2H), 1.55~1.19 (m, 8H), 0.84 (t, J = 6.3, 3H) | | |
| 352 | 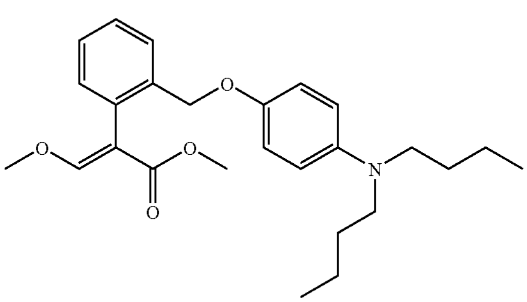 | 7.57 (s, 1H), 7.54~7.17 (m, 6H), 6.83~6.78 (m, 1H), 6.61~6.56 (m, 1H), 4.87 (s, 2H), 3.80 (s, 3H), 3.69 (s, 3H), 3.19~3.11 (m, 4H), 1.50~1.26 (m, 8H), 0.95~0.88 (m, 6H) | | |

TABLE 3a-continued

| Com. No. | structure | ¹H NMR (CDCl₃, TMS) δ (ppm) | MS (m/z, relative intensity) | mp (° C.) |
|---|---|---|---|---|
| 353 | 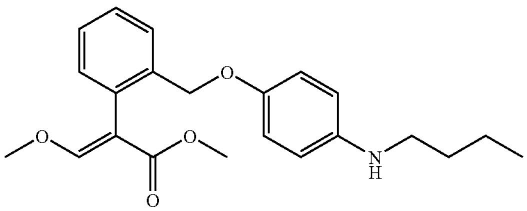 | 7.57 (s, 1H), 7.55~7.26 (m, 3H), 7.17~7.13 (m, 1H), 6.79~6.75 (m, 2H), 6.55~6.51(m, 2H), 4.87 (s, 2H), 4.02 (b, 1H), 3.80 (s, 3H), 3.69 (s, 3H), 3.04 (t, J = 6.9, 2H), 1.62~1.39 (m, 4H), 0.94 (t, J = 7.1, 3H) | | |

TABLE 3b

| Com. No. | structure | ¹H NMR (CDCl₃, TMS) δ (ppm) |
|---|---|---|
| 354 | 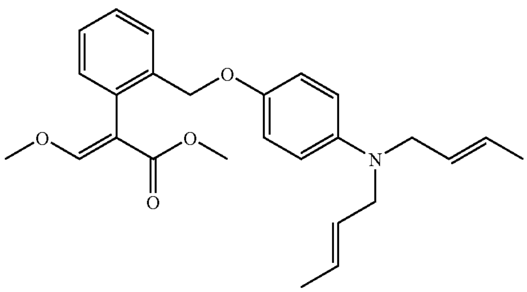 | 7.57 (s, 1H), 7.56~7.54 (m, 1H), 7.34~7.17 (m, 5H), 6.82~6.77 (m, 1H), 6.68~6.62 (m, 1H), 5.56~5.48 (m, 4H), 4.87 (s, 2H), 3.81 (s, 3H), 3.74~3.70 (m, 4H), 3.69 (s, 3H), 1.69~1.66 (m, 6H) |
| 355 | 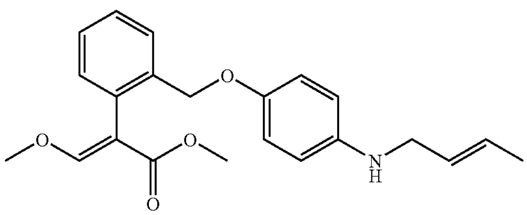 | 7.56 (s, 1H), 7.55~7.53 (m, 1H), 7.33~7.29 (m, 2H), 7.16~7.14 (m, 1H), 6.79~6.76 (m, 2H), 6.60~6.56 (m, 2H), 5.66~5.61 (m, 2H), 4.87 (s, 2H), 4.01 (b, 1H), 3.80 (s, 3H), 3.69 (s, 3H), 3.62 (d, J = 5.6, 2H), 1.70~1.68 (m, 3H) |
| 356 | 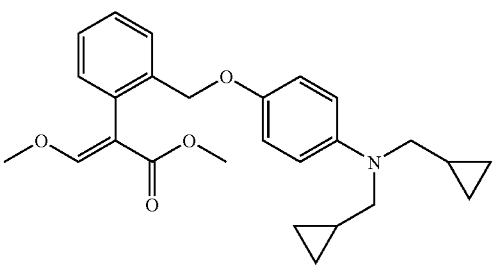 | 7.57 (s, 1H), 7.56~7.54 (m, 1H), 7.31~7.26 (m, 2H), 7.17~7.13 (m, 1H), 6.82~6.71 (m, 4H), 4.89 (s, 2H), 3.81 (s, 3H), 3.69 (s, 3H), 3.16~3.14 (m, 4H), 1.08~0.95 (m, 2H), 0.48~0.46 (m, 4H), 0.17~0.15 (m, 4H) |
| 357 | 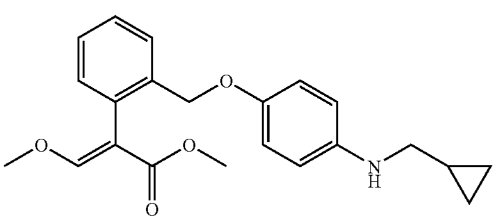 | 7.56 (s, 1H), 7.55~7.53 (m, 1H), 7.31~7.25 (m, 2H), 7.15~7.11 (m, 1H), 6.78~6.75 (m, 2H), 6.56~6.53 (m, 2H), 4.87 (s, 2H), 4.01 (b, 1H), 3.81 (s, 3H), 3.68 (s, 3H), 2.89 (d, J = 6.9, 2H), 1.16~1.04 (m, 1H), 0.54~0.51 (m, 2H), 0.21~0.20 (m, 2H) |
| 358 | 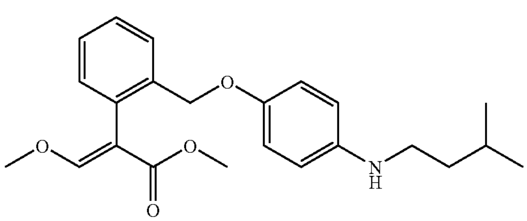 | 7.57 (s, 1H), 7.55~7.53 (m, 1H), 7.34~7.26 (m, 2H), 7.17~7.13 (m, 1H), 6.81~6.75 (m, 2H), 6.55~6.51 (m, 2H), 4.87 (s, 2H), 4.03 (b, 1H), 3.81 (s, 3H), 3.69 (s, 3H), 3.05 (t, J = 7.3, 2H), 1.56~1.51 (m, 1H), 1.50~1.43 (m, 2H), 0.95~0.91 (m, 6H) |

TABLE 3b-continued

| | | |
|---|---|---|
| 359 | (structure) | 7.57 (s, 1H), 7.55~7.52 (m, 1H), 7.36~7.25 (m, 2H), 7.17~7.13 (m, 1H), 6.86~6.73 (m, 3H), 6.69~6.54 (m, 1H), 4.89 (s, 2H), 4.01 (b, 1H), 3.82 (s, 3H), 3.69 (s, 3H), 3.63~3.14 (m, 2H), 2.83~2.67 (m, 1H), 2.58~2.54 (m, 2H) |

TABLE 3c

| | | |
|---|---|---|
| 360 | (structure) | 7.57 (s, 1H), 7.55~7.53 (m, 1H), 7.34~7.28 (m, 2H), 7.17~7.13 (m, 1H), 6.79~6.74 (m, 2H), 6.54~6.50 (m, 2H), 4.87 (s, 2H), 4.02 (b, 1H), 3.80 (s, 3H), 3.69 (s, 3H), 1.99~1.93 (m, 1H), 1.71~1.59 (m, 4H), 1.50~1.43 (m, 4H) |
| 361 | (structure) | 7.57 (s, 1H), 7.55~7.53 (m, 1H), 7.34~7.26 (m, 2H), 7.17~7.12 (m, 1H), 6.79~6.73 (m, 2H), 6.56~6.50 (m, 2H), 4.87 (s, 2H), 4.01 (b, 1H), 3.80 (s, 3H), 3.69 (s, 3H), 2.86 (d, J = 6.7, 2H), 1.88~1.82 (m, 1H), 0.96 (d, J = 6.7, 6H) |
| 362 | (structure) | 7.58 (s, 1H), 7.57~7.53 (m, 1H), 7.34~7.25 (m, 2H), 7.17~7.12 (m, 1H), 6.79~6.74 (m, 2H), 6.52~6.49 (m, 2H), 4.87 (s, 2H), 4.02 (b, 1H), 3.80 (s, 3H), 3.69 (s, 3H), 3.27~3.03 (m, 1H), 1.58~1.41 (m, 2H), 1.13 (d, J = 6.3, 3H), 0.93 (t, J = 7.5, 3H) |
| 363 | (structure) | 7.57 (s, 1H), 7.55~7.53 (m, 1H), 7.34~7.26 (m, 2H), 7.17~7.13 (m, 1H), 6.80~6.75 (m, 2H), 6.59~6.54 (m, 2H), 4.88 (s, 2H), 4.02 (b, 1H), 3.80 (s, 3H), 3.68 (s, 3H), 3.58 (t, J = 4.9, 2H), 3.38 (s, 3H), 3.22 (t, J = 5.3, 2H) |
| 364 | (structure) | 7.58 (s, 1H), 7.54~7.50 (m, 1H), 7.34~7.13 (m, 3H), 6.64~6.56 (m, 3H), 4.87 (s, 2H), 4.01 (b, 1H), 3.82 (s, 3H), 3.69 (s, 3H), 2.89 (d, J = 6.7, 2H), 1.31~1.25 (m, 1H), 0.97 (d, J = 6.5, 6H) |
| 365 | (structure) | 7.58 (s, 1H), 7.55~7.50 (m, 1H), 7.34~7.23 (m, 2H), 7.18~7.13 (m, 1H), 6.65~6.57 (m, 3H), 4.86 (s, 2H), 4.01 (b, 1H), 3.82 (s, 3H), 3.69 (s, 3H), 3.34~3.28 (m, 1H), 1.59~1.48 (m, 2H), 1.14 (d, J = 6.3, 3H), 0.94 (t, J = 7.3, 3H) |

TABLE 3d
| | | |
|---|---|---|
| 366 | 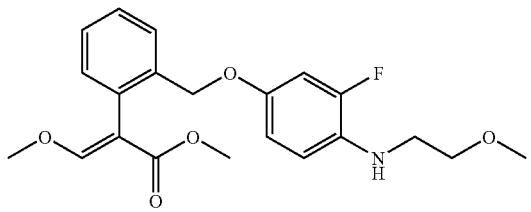 | 7.58 (s, 1H), 7.54~7.49 (m, 1H), 7.34~7.26 (m, 2H), 7.18~7.13 (m, 1H), 6.67~6.54 (m, 3H), 4.87 (s, 2H), 4.02 (b, 1H), 3.82 (s, 3H), 3.69 (s, 3H), 3.59 (t, J = 4.8, 2H), 3.38 (s, 3H), 3.25 (t, J = 5.3, 2H) |
| 367 | 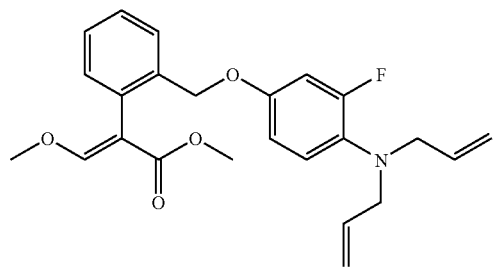 | 7.59 (s, 1H), 7.54~7.49 (m, 1H), 7.35~7.26 (m, 2H), 7.18~7.14 (m, 1H), 6.89~6.79 (m, 1H), 6.64~6.54 (m, 2H), 5.87~5.70 (m, 2H), 5.19~5.08 (m, 4H), 4.87 (s, 2H), 3.82 (s, 3H), 3.70 (s, 3H), 3.67~3.64 (m, 4H) |
| 368 | 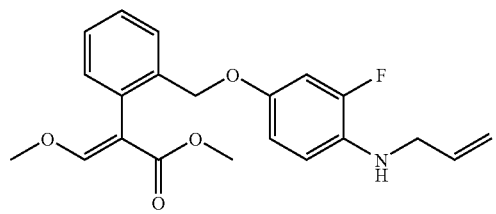 | 7.58 (s, 1H), 7.54~7.49 (m, 1H), 7.34~7.26 (m, 2H), 7.17~7.13 (m, 1H), 6.66~6.57 (m, 3H), 6.01~5.81 (m, 1H), 5.31~5.13 (m, 2H), 4.87 (s, 2H), 4.01 (b, 1H), 3.81 (s, 3H), 3.81~3.72 (m, 2H), 3.69 (s, 3H) |
| 369 | 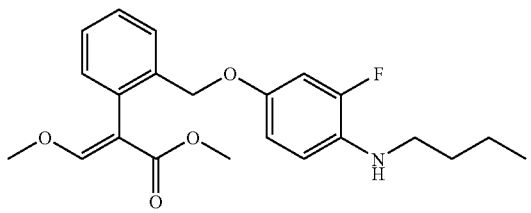 | 7.58 (s, 1H), 7.54~7.50 (m, 1H), 7.34~7.29 (m, 2H), 7.18~7.13 (m, 1H), 6.66~6.58 (m, 3H), 4.87 (s, 2H), 4.01 (b, 1H), 3.82 (s, 3H), 3.70 (s, 3H), 3.07 (t, J = 6.9, 2H), 1.64~1.43 (m, 4H), 0.95 (t, J = 7.1, 3H) |
| 370 | 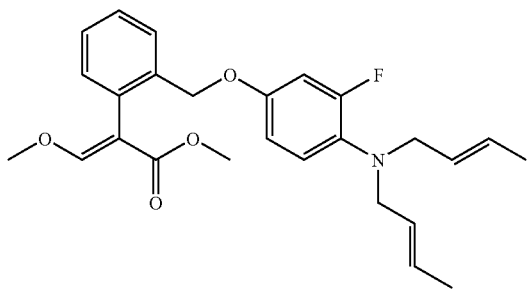 | 7.59 (s, 1H), 7.55~7.50 (m, 1H), 7.35~7.30 (m, 2H), 7.18~7.14 (m, 1H), 6.87~6.78 (m, 1H), 6.63~6.54 (m, 2H), 5.61~5.37 (m, 4H), 4.89 (s, 2H), 3.83 (s, 3H), 3.70 (s, 3H), 3.56~3.54 (m, 4H), 1.66~1.57 (m, 6H) |
| 371 | 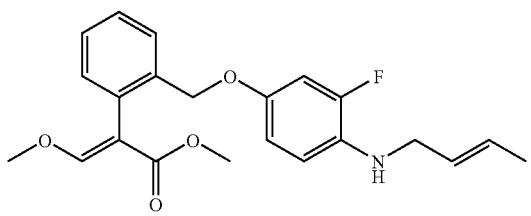 | 7.60 (s, 1H), 7.68~7.50 (m, 1H), 7.34~7.26 (m, 2H), 7.19~7.13 (m, 1H), 6.66~6.58 (m, 3H), 5.69~5.58 (m, 2H), 4.87 (s, 2H), 4.01 (b, 1H), 3.82 (s, 3H), 3.69 (s, 3H), 3.66~3.63 (m, 2H), 1.71~1.68 (m, 3H) |

TABLE 3e
| | | |
|---|---|---|
| 372 | 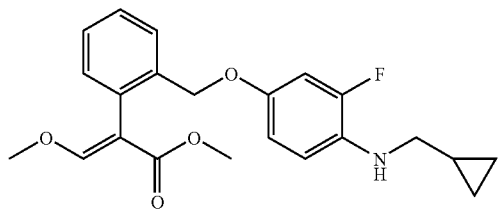 | 7.59 (s, 1H), 7.55~7.49 (m, 1H), 7.34~7.26 (m, 2H), 7.17~7.13 (m, 1H), 6.66~6.56 (m, 3H), 4.86 (s, 2H), 4.01 (b, 1H), 3.82 (s, 3H), 3.69 (s, 3H), 2.91 (d, J = 6.9, 2H), 1.25~1.09 (m, 1H), 0.59~0.50 (m, 2H), 0.26~0.20 (m, 2H) |
| 373 | 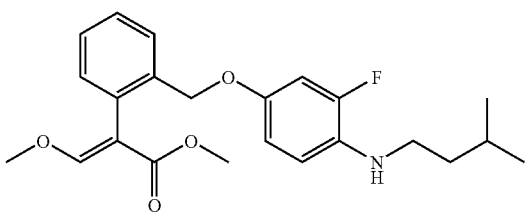 | 7.58 (s, 1H), 7.52~7.50 (m, 1H), 7.34~7.26 (m, 2H), 7.17~7.12 (m, 1H), 6.64~6.58 (m, 3H), 4.86 (s, 2H), 4.03 (b, 1H), 3.82 (s, 3H), 3.69 (s, 3H), 3.08 (t, J = 7.3, 2H), 1.54~1.48 (m, 1H), 1.25~1.20 (m, 2H), 0.95~0.85 (m, 6H) |
| 374 | 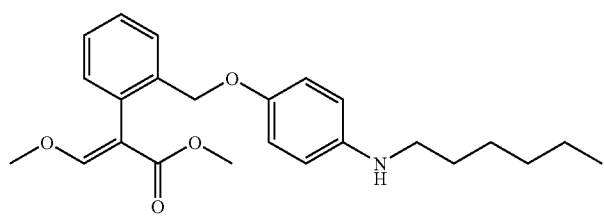 | 7.57 (s, 1H), 7.53~7.50 (m, 1H), 7.34~7.26 (m, 2H), 7.17~7.15 (m, 1H), 6.75~6.73 (m, 2H), 6.59~6.51 (m, 2H), 4.87 (s, 2H), 4.02 (b, 1H), 3.81 (s, 3H), 3.69 (s, 3H), 3.04 (t, J = 7.1, 2H), 1.59~1.54 (m, 2H), 1.32~1.25 (m, 6H), 0.89~0.81 (m, 3H) |
| 375 | 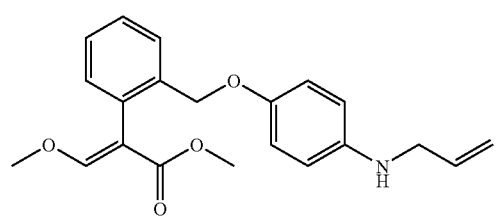 | 7.57 (s, 1H), 7.55~7.51 (m, 1H), 7.34~7.28 (m, 2H), 7.17~7.14 (m, 1H), 6.80~6.75 (m, 2H), 6.57~6.53 (m, 2H), 6.01~5.84 (m, 1H), 5.31~5.12 (m, 2H), 4.87 (s, 2H), 4.01 (b, 1H), 3.81 (s, 3H), 3.73~3.70 (m, 2H), 3.68 (s, 3H) |
| 376 | 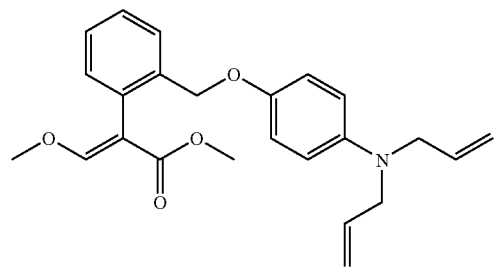 | 7.70 (s, 1H), 7.58~7.54 (m, 1H), 7.38~7.26 (m, 2H), 7.17~7.13 (m, 1H), 6.84~6.75 (m, 2H), 6.67~6.61 (m, 2H), 5.93~5.74 (m, 2H), 5.21~5.10 (m, 4H), 4.87 (s, 2H), 3.85~3.80 (m, 7H), 3.68 (s, 3H) |
| 377 | 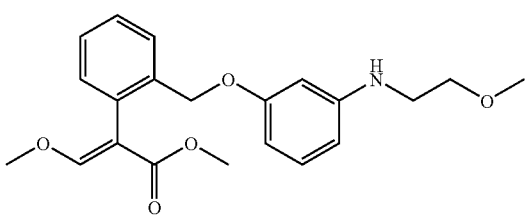 | 7.57 (s, 1H), 7.55~7.52 (m, 1H), 7.34~7.30 (m, 2H), 7.17~7.03 (m, 1H), 6.28~6.20 (m, 4H), 4.91 (s, 2H), 4.08 (b, 1H), 3.81 (s, 3H), 3.59~3.56 (m, 2H), 3.70 (s, 3H), 3.37 (s, 3H), 3.26~3.23 (m, 2H) |

TABLE 3f

| # | Structure | NMR |
|---|---|---|
| 378 | 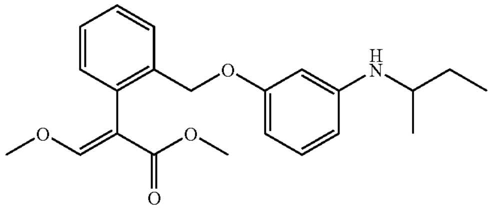 | 7.57 (s, 1H), 7.55~7.52 (m, 1H), 7.33~7.24 (m, 2H), 7.15~7.10 (m, 1H), 6.76~6.71 (m, 2H), 6.50~6.45 (m, 2H), 4.87 (s, 2H), 4.01 (b, 1H), 3.81 (s, 3H), 3.70 (s, 3H), 2.97~2.83 (m, 1H), 1.11~1.01 (m, 2H), 0.95 (d, J = 6.7, 3H), 0.85 (t, J = 7.3, 3H) |
| 379 | 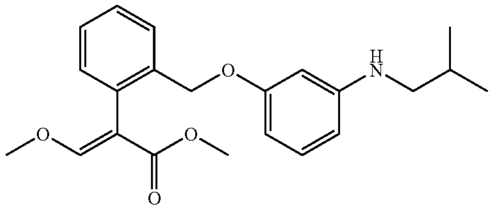 | 7.58 (s, 1H), 7.55~7.50 (m, 1H), 7.34~7.30 (m, 2H), 7.17~7.14 (m, 1H), 7.04~6.98 (m, 2H), 6.27~6.17 (m, 2H), 4.91 (s, 2H), 4.01 (b, 1H), 3.81 (s, 3H), 3.70 (s, 3H), 3.37~3.31 (m, 1H), 1.28~1.13 (m, 2H), 0.98~0.90 (m, 6H) |
| 380 | 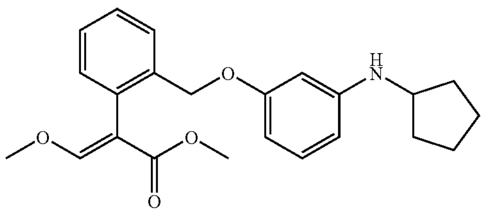 | 7.57 (s, 1H), 7.54~7.51 (m, 1H), 7.33~7.26 (m, 1H), 7.17~7.14 (m, 1H), 7.04~6.99 (m, 1H), 6.27~6.18 (m, 4H), 4.91 (s, 2H), 4.69 (b, 1H), 3.81 (s, 3H), 3.69 (s, 3H), 2.01~1.92 (m, 1H), 1.83~1.55 (m, 4H), 1.54~1.43 (m, 4H) |
| 381 | 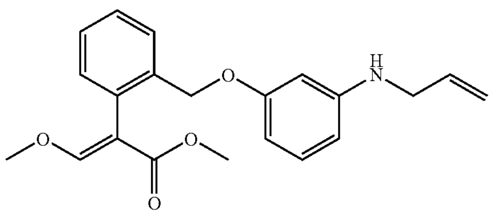 | 7.57 (s, 1H), 7.55~7.52 (m, 1H), 7.31~7.25 (m, 2H), 7.19~7.15 (m, 1H), 7.12~6.99 (m, 2H), 6.35~6.29 (m, 2H), 5.91~5.75 (m, 1H), 5.18~5.10 (m, 2H), 4.91 (s, 2H), 4.01 (b, 1H), 3.88~3.77 (m, 2H), 3.80 (s, 3H), 3.68 (s, 3H) |
| 382 | 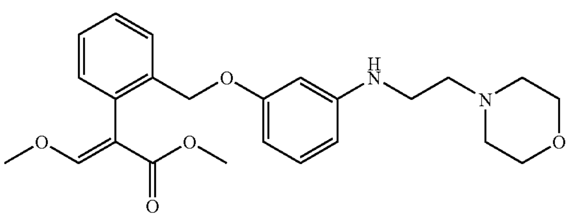 | 7.59 (s, 1H), 7.58~7.52 (m, 1H), 7.33~7.31 (m, 2H), 7.18~7.12 (m, 1H), 6.98~6.60 (m, 2H), 6.24~6.20 (m, 2H), 4.92 (s, 2H), 4.23 (b, 1H), 3.83 (s, 3H), 3.74~3.71 (m, 4H), 3.70 (s, 3H), 2.66 (t, J = 6.1, 2H), 2.59 (t, J = 5.7, 2H), 2.50~2.46 (m, 4H) |
| 383 | 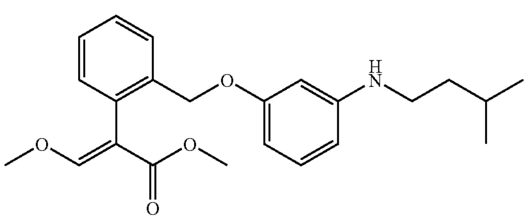 | 7.57 (s, 1H), 7.56~7.54 (m, 1H), 7.34~7.29 (m, 1H), 7.17~7.15 (m, 1H), 7.02~6.99 (m, 1H), 6.25~6.18 (m, 4H), 4.91 (s, 2H), 3.81 (s, 3H), 3.69 (s, 3H), 3.07 (t, J = 7.3, 2H), 1.72~1.63 (m, 1H), 1.54~1.44 (m, 2H), 0.96~0.92 (m, 6H) |

TABLE 3g

| # | Structure | NMR |
|---|---|---|
| 384 | 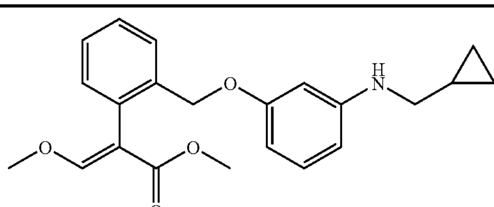 | 7.57 (s, 1H), 7.56~7.53 (m, 1H), 7.33~7.29 (m, 1H), 7.17~7.15 (m, 1H), 7.05~6.99 (m, 1H), 6.27~6.17 (m, 4H), 4.91 (s, 2H), 4.01 (b, 1H), 3.81 (s, 3H), 3.70 (s, 3H), 2.91 (d, J = 6.9, 2H), 1.09~1.07 (m, 1H), 0.56~0.50 (m, 2H), 0.24~0.19 (m, 2H) |

TABLE 3g-continued

| No. | Structure | NMR | MS | mp |
|---|---|---|---|---|
| 385 | 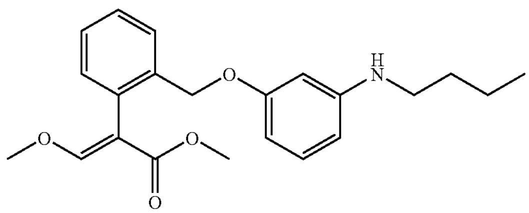 | 7.57 (s, 1H), 7.56~7.54 (m, 1H), 7.34~7.30 (m, 1H), 7.17~7.15 (m, 1H), 7.02~6.99 (m, 1H), 6.25~6.17 (m, 4H), 4.91 (s, 2H), 3.81 (s, 3H), 3.69 (s, 3H), 3.59 (b, 1H), 3.06 (t, J = 7.2, 2H), 1.60~1.46 (m, 4H), 0.98~0.91 (m, 3H) | | |
| 386 | 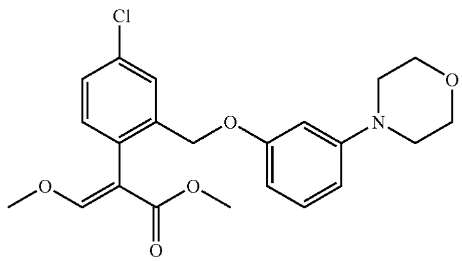 | 7.59 (s, 1H), 7.57~7.07 (m, 4H), 6.55~6.37 (m, 3H), 4.89 (s, 2H), 3.87~3.84 (m, 4H), 3.83 (s, 3H), 3.70 (s, 3H), 3.16~3.11 (m, 4H) | 417 (25, M$^+$), 179 (100), 137 (22), 92 (24), 59 (27) | |
| 387 | 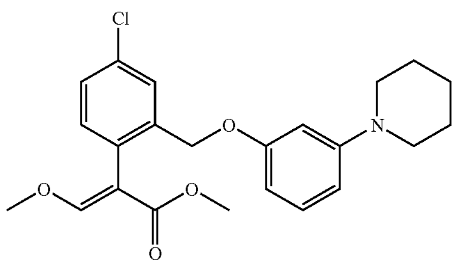 | 7.58 (s, 1H), 7.30~7.07 (m, 4H), 6.58~6.31 (m, 3H), 4.88 (s, 2H), 3.83 (s, 3H), 3.69 (s, 3H), 3.17~3.11 (m, 4H), 1.69~1.55 (m, 6H) | 415 (32 M$^+$), 179 (100), 148 (38), 59 (44), 41 (46) | 66-68 |
| 388 | 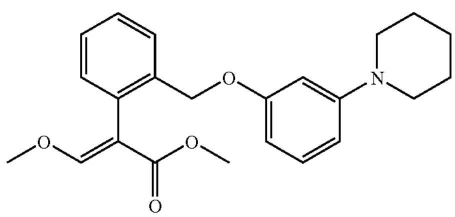 | 7.58 (s, 1H), 7.53~7.06 (m, 5H), 6.55~6.34 (m, 3H), 4.93 (s, 2H), 3.81 (s, 3H), 3.69 (s, 3H), 3.15~3.10 (m, 4H), 1.58~1.54 (m, 6H) | 381 (10, M$^+$), 205 (11), 145 (36), 43 (100) | 64-66 |
| 389 | 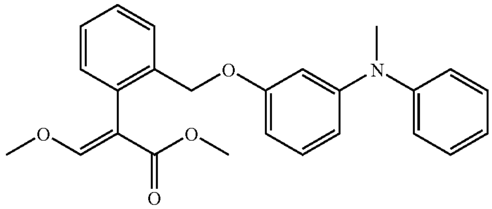 | 7.56 (s, 1H), 7.35~6.97 (m, 10H), 6.97~6.55 (m, 3H), 4.90 (s, 2H), 3.77 (s, 3H), 3.66 (s, 3H), 3.28 (s, 3H) | 403 (18, M$^+$), 145 (100), 103 (40), 77 (30), 42 (18) | |
| 390 | 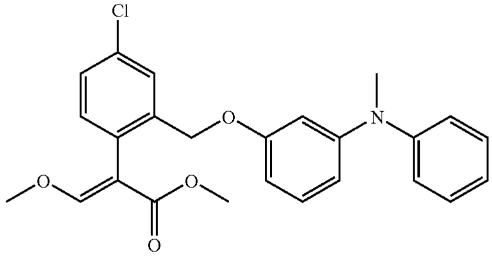 | 7.56 (s, 1H), 7.54~6.95 (m, 9H), 6.59~6.42 (m, 3H), 4.85 (s, 2H), 3.78 (s, 3H), 3.67 (s, 3H), 3.29 (s, 3H) | 437 (37, M$^+$), 239 (32) 179 (100), 59 (22), 42 (23) | |

TABLE 3g-continued

| | | | | |
|---|---|---|---|---|
| 391 | [structure] | 7.58 (s, 1H), 7.55~7.08 (m, 5H), 6.54~6.37 (m, 3H), 4.93 (s, 2H), 3.81 (s, 3H), 3.69 (s, 3H), 3.22~3.17 (m, 4H), 2.59~2.54 (m, 4H), 2.34 (s, 3H) | 397 (10, M$^+$), 145 (28) 42 (100), 39 (63) | |
| 392 | [structure] | 7.58 (s, 1H), 7.64~7.04 (m, 5H), 6.25~6.15 (m, 3H), 4.94 (s, 2H), 3.81 (s, 3H), 3.69 (s, 3H), 3.27~3.21 (m, 4H), 2.17~2.01 (m, 4H) | 367 (21, M$^+$), 205 (23) 145 (100), 77 (26), 42 (14) | 84-86 |

TABLE 3h

| | | | | |
|---|---|---|---|---|
| 393 | [structure] | 7.76 (s, 1H), 7.59~7.55 (m, 2H), 7.36~7.14 (m, 4H), 6.93~6.75 (m, 1H), 5.20 (s, 2H), 3.88~3.83 (m, 4H), 3.79 (s, 3H), 3.67 (s, 3H), 3.07~3.02 (m, 4H) | 384 (34, M$^+$), 205 (38), 145 (100), 103 (17), 59 (11) | 130-132 |
| 394 | [structure] | 7.75 (s, 1H), 7.58~7.56 (m, 2H), 7.30~7.24 (m, 2H), 7.10~7.06 (m, 1H), 6.74~6.70 (m, 1H), 5.16 (s, 2H), 3.88~3.83 (m, 4H), 3.81 (s, 3H), 3.68 (s, 3H), 3.07~3.03 (m, 4H) | 418 (34, M$^+$), 239 (50), 179 (100), 124 (26), 59 (17) | |
| 395 | [structure] | 7.58 (s, 1H), 7.32~7.13 (m, 5H), 6.57~6.46 (m, 2H), 5.04 (s, 2H), 3.85 (s, 3H), 3.65 (s, 3H), 2.71~2.66 (m, 4H), 1.62~1.48 (m, 6H) | 382 (34, M$^+$), 205 (18), 177 (31), 145 (100) 103 (18), 41 (20) | |
| 396 | [structure] | 7.57 (s, 1H), 7.35~7.14 (m, 7H), 6.97~6.96 (m, 1H), 6.82~6.57 (m, 4H), 5.11 (s, 2H), 3.80 (s, 3H), 3.61 (s, 3H), 3.07 (s, 3H) | 403 (51, M$^+$), 205 (20), 145 (100), 103 (39), 77 (26) | |

TABLE 3h-continued
| | | | |
|---|---|---|---|
| 397 | 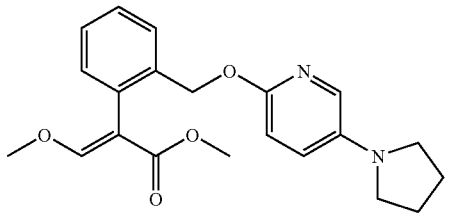 | 7.59~7.56 (m, 1H), 7.54 (s, 1H), 7.49~7.13 (m, 4H), 6.96~6.90 (m, 1H), 6.68~6.63 (m, 1H), 5.18 (s, 2H), 3.79 (s, 3H), 3.67 (s, 3H), 3.25~3.19 (m, 4H), 2.04~1.97 (m, 4H) | 368 (14, M⁺), 205 (37), 163 (31), 145 (100), 108 (38), 40 (89) | 112-114 |
| 398 | 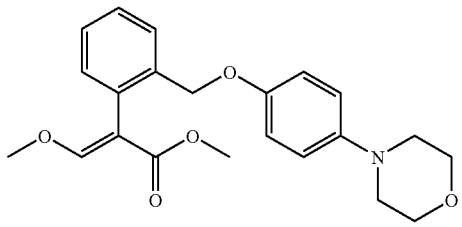 | 7.57 (s, 1H), 7.52~7.14 (m, 4H), 7.86~7.84 (m, 4H), 4.91 (s, 2H), 3.87~3.82 (m, 4H), 3.81 (s, 3H), 3.69 (s, 3H), 3.06~3.01 (m, 4H) | 383 (17, M⁺), 205 (33), 178 (100), 145 (57), 77 (64), 65 (69) | 128-130 |
| 399 | 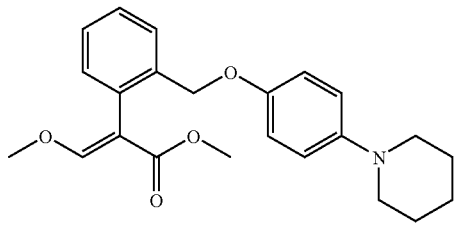 | 7.57 (s, 1H), 7.53~7.15 (m, 4H), 6.85~6.83 (m, 4H), 4.90 (s, 2H), 3.81 (s, 3H), 3.69 (s, 3H), 3.03~2.98 (m, 4H), 1.73~1.53 (m, 6H) | 381 (13, M⁺), 205 (21), 176 (100), 145 (30), 41 (31) | |
| 400 | 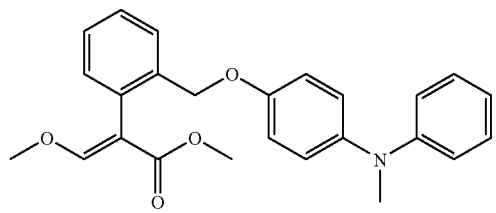 | 7.60 (s, 1H), 7.58~6.74 (m, 13H), 4.96 (s, 2H), 3.83 (s, 3H), 3.70 (s, 3H), 3.24 (s, 3H) | 403 (14, M⁺), 205 (28), 198 (100), 145 (56) | |
| 401 | 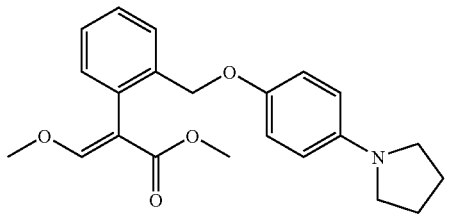 | 7.59 (s, 1H), 7.54~7.13 (m, 4H), 6.86~6.80 (m, 2H), 6.51~6.47 (m, 2H), 4.89 (s, 2H), 3.81 (s, 3H), 3.69 (s, 3H), 3.25~3.18 (m, 4H), 2.00~1.94 (m, 4H) | 367 (13, M⁺), 205 (16), 162 (100), 145 (41), 77 (20), 65 (13) | 122-124 |
TABLE 3i
| | | | |
|---|---|---|---|
| 402 | 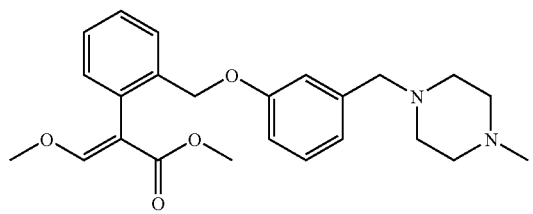 | 7.58 (s, 1H), 7.55~7.52 (m, 1H), 7.33~7.30 (m, 2H), 7.17~7.15 (m, 2H), 6.89~6.87 (m, 2H), 6.79~6.76 (m, 1H), 4.95 (s, 2H), 3.81 (s, 3H), 3.69 (s, 3H), 3.46 (m, 2H), 2.44~2.34 (m, 8H), 2.28 (s, 3H) | | |

TABLE 3i-continued

| No. | Structure | 1H NMR | MS | mp |
|---|---|---|---|---|
| 403 | 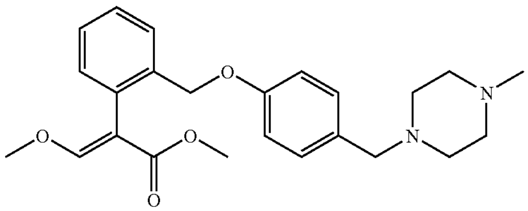 | 7.57 (s, 1H), 7.54~7.51 (m, 1H), 7.33~7.29 (m, 2H), 7.19~7.14 (m, 3H), 6.85~6.82 (m, 2H), 4.94 (s, 2H), 3.79 (s, 3H), 3.68 (s. 3H), 3.42 (m, 2H), 2.43~2.32 (m, 8H), 2.27 (s, 3H) | | |
| 404 | 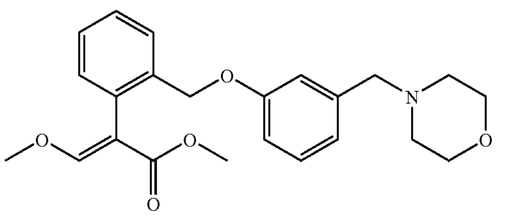 | 7.57 (s, 1H), 7.54~7.51 (m, 1H), 7.31~7.28 (m, 2H), 7.17~7.14 (m, 2H), 6.89~6.86 (m, 2H), 6.80~6.79 (m, 1H), 4.95 (s, 2H), 3.78 (s, 3H), 3.68 (s, 3H), 3.65~3.61 (m, 4H), 3.44 (m, 2H), 2.44~2.34 (m, 4H) | | |
| 405 | 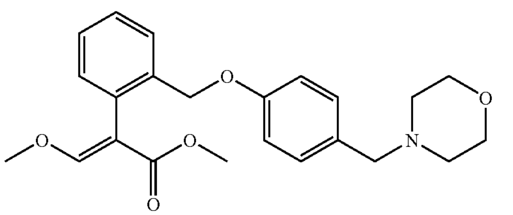 | 7.58 (s, 1H), 7.55~7.52 (m, 1H), 7.33~7.28 (m, 2H), 7.19~7.15 (m, 3H), 6.86~6.82 (m, 2H), 4.96 (s, H), 3.81 (s, 3H), 3.69 (s, 3H), 3.67~3.64 (m, 4H), 3.41 (m, 2H), 2.42~2.39 (m, 4H) | | |
| 406 | 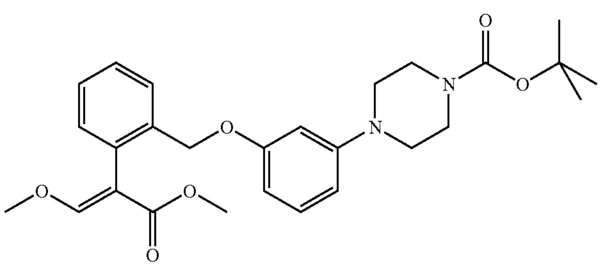 | 7.58 (s, 1H), 7.54~7.09 (m, 5H), 6.53~6.41 (m, 3H), 4.94 (s, 2H), 3.82 (s, 3H), 3.69 (s, 3H), 3.57~3.52 (m, 4H), 3.13~3.07 (m, 4H), 1.48 (s, 9H) | 482 (11, M+), 205 (26), 145 (100), 57 (51) | 138-140 |
| 407 | 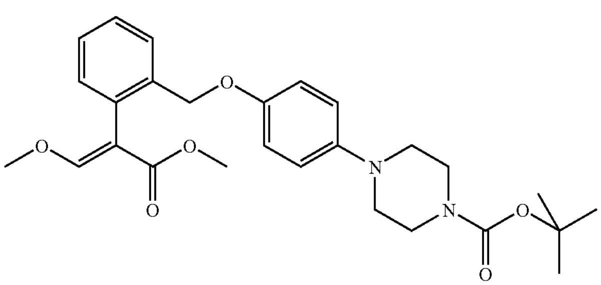 | 7.58 (s, 1H), 7.52~7.14 (m, 4H), 6.86~6.84 (m, 4H), 4.91 (s, 2H), 3.82 (s, 3H), 3.70 (s, 3H), 3.67~3.53 (m, 4H), 3.01~2.96 (m, 4H), 1.48 (s, 9H) | 483 (12, M+), 221 (62) 205 (45), 145 (100), 57 (52), | |
| 408 | 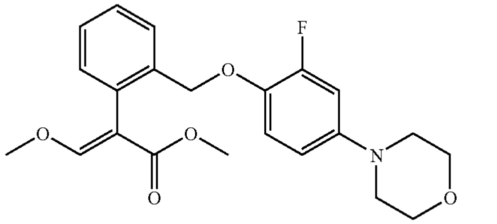 | 7.59 (s, 1H), 7.58~7.54 (m, 1H), 7.34~7.30 (m, 2H), 7.17~7.14 (m, 1H), 6.93~6.66 (m, 3H), 4.96 (s, 2H), 3.85~3.82 (m, 4H), 3.81 (s, 3H) 3.63 (s, 3H), 3.06~3.03 (m, 4H) | | |

TABLE 3j

| | | | |
|---|---|---|---|
| 409 | | 7.57 (s, 1H), 7.32~7.13 (m, 5H), 6.59~6.50 (m, 2H), 5.04 (s, 2H), 3.84 (s, 3H), 3.64 (s, 3H), 2.82~2.76 (m, 4H), 2.52~2.47 (m, 4H), 2.31 (s, 3H) | 397 (34, M$^+$), 205 (11), 145 (43), 70 (20), 43 (100) |
| 410 | | 7.59 (s, 1H), 7.52~7.14 (m, 4H), 6.89~6.59 (m, 3H), 4.91 (s, 2H), 3.87~3.84 (m, 4H), 3.82 (s, 3H), 3.70 (s, 5H), 2.99~2.95 (m, 4H) | 401 (11, M$^+$), 205 (48), 145 (100), 103 (31), 77 (21) |
| 411 | | 7.56 (s, 1H), 7.54~7.14 (m, 5H), 6.16~6.06 (m, 2H), 5.22 (s, 2H), 3.79 (s, 3H), 3.67 (s, 3H), 3.65~3.48 (m, 4H), 2.52~2.46 (m, 4H), 2.34 (s, 3H) | 397 (10, M$^+$), 205 (77), 145 (80), 70 (42), 42 (100) |
| 412 | | 7.59 (s, 1H), 7.53~7.19 (m, 4H), 6.87~6.59 (m, 3H), 4.90 (s, 2H), 3.83 (s, 3H), 3.70 (s, 3H), 3.02~2.99 (m, 4H), 2.62~2.59 (m, 4H), 2.35 (s, 3H) | 414 (11, M$^+$), 247 (31), 205 (36), 145 (57), 43 (100) |
| 413 | | 7.57 (s, 1H), 7.55~7.14 (m, 5H), 6.16~6.12 (m, 1H), 6.04~6.00 (m, 1H), 5.22 (s, 2H), 3.79 (s, 3H), 3.67 (s, 3H), 3.59~3.47 (m, 4H), 1.62~1.55 (m, 6H) | 382 (27, M$^+$), 205 (40), 177 (100), 145 (67), 103 (38), 41 (40) |
| 414 | | 7.57 (s, 1H), 7.54~7.14 (m, 10H), 6.08~6.03 (m, 2H), 5.25 (s, 2H), 3.79 (s, 3H), 3.68 (s, 3H), 3.42 (s, 3H) | 404 (12, M$^+$), 205 (40), 145 (100), 103 (38), 77 (28) |
| 415 | | 7.58 (s, 1H), 7.56~7.13 (m, 5H), 5.97~5.25 (m, 2H), 5.25 (s, 2H), 3.79 (s, 3H), 3.68 (s, 3H), 3.43~3.36 (m, 4H), 2.04~1.92 (m, 4H) | 368 (31, M$^+$), 205 (44), 163 (46), 145 (100), 103 (36), 40 (74) |

TABLE 3j-continued
| | | | |
|---|---|---|---|
| 416 | 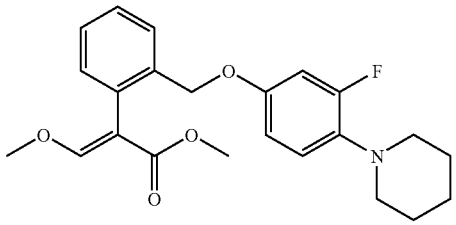 | 7.59 (s, 1H), 7.53~7.14 (m, 4H), 6.90~6.81 (m, 1H), 6.65~6.57 (m, 2H), 4.89 (s, 2H), 3.82 (s, 3H), 3.70 (s, 3H), 2.93~2.87 (m, 4H), 1.75~1.53 (m, 6H) | 399 (15, M+), 359 (32), 194 (63), 145 (85), 69 (39), 41 (100) |
| 417 | 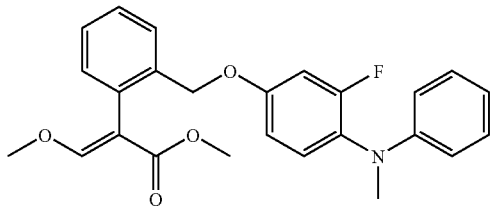 | 7.62 (s, 1H), 7.56~7.11 (m, 8H), 6.78~6.62 (m, 4H), 4.96 (s, 2H), 3.85 (s, 3H), 3.71 (s, 3H), 3.21 (s, 3H) | 421 (19, M+), 216 (56), 205 (39), 145 (100), 103 (34), 145 (100), 40 (38) |
TABLE 3k
| | | | |
|---|---|---|---|
| 418 | 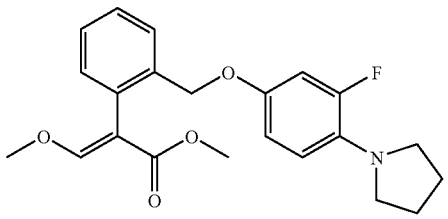 | 7.59 (s, 1H), 7.55~7.14 (m, 4H), 6.68~6.59 (m, 3H), 4.88 (s, 2H), 3.82 (s, 3H), 3.70 (s, 3H), 3.26~3.20 (m, 4H), 1.95~1.88 (m, 4H) | 385 (18, M+), 205 (32), 180 (72), 145 (100), 55 (28) |
| 419 | 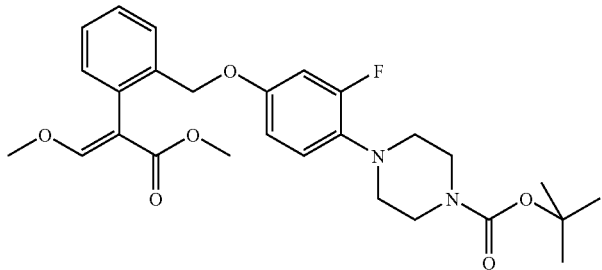 | 7.59 (s, 1H), 7.48~7.17 (m, 4H), 6.84~6.82 (m, 1H), 6.67~6.59 (m, 2H), 4.91 (s, 2H), 3.83 (s, 3H), 3.70 (s, 3H), 3.59~3.54 (m, 4H), 2.94~2.88 (m, 4H), 1.47 (s, 9H) | 500 (11, M+), 205 (62), 145 (77), 56 (49), 40 (100) |
| 420 | 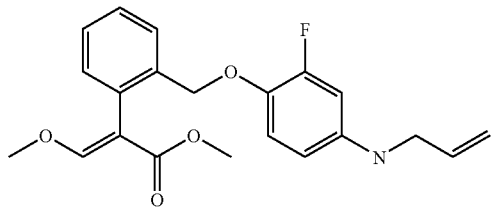 | 7.59 (s, 1H), 7.57~7.55 (m, 1H), 7.37~7.26 (m, 2H), 7.17~7.12 (m, 1H), 6.79~6.70 (m, 1H), 6.43~6.35 (m, 1H), 6.26~6.19 (m, 1H), 5.99~5.82 (m, 1H), 5.31~5.13 (m, 2H), 4.91 (s, 2H), 3.80 (s, 3H), 3.78~3.70 (m, 2H), 3.68 (s, 3H), 3.61 (b, 1H) | |
| 421 | 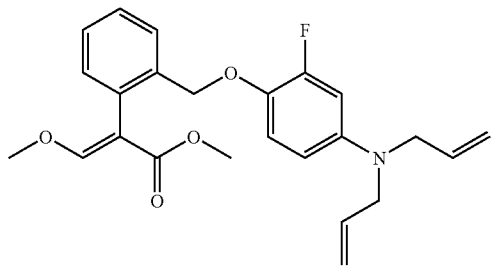 | 7.61 (s, 1H), 7.59~7.57 (m, 1H), 7.35~7.26 (m, 2H), 7.17~7.12 (m, 1H), 6.81~6.72 (m, 1H), 6.51~6.42 (m, 1H), 6.31~6.26 (m, 1H), 5.88~5.72 (m, 2H), 5.20~5.11 (m, 4H), 4.91 (s, 2H), 3.84~3.81 (m, 4H), 3.80 (s, 3H), 3.68 (s, 3H) | |

TABLE 3k-continued
| | | |
|---|---|---|
| 422 | 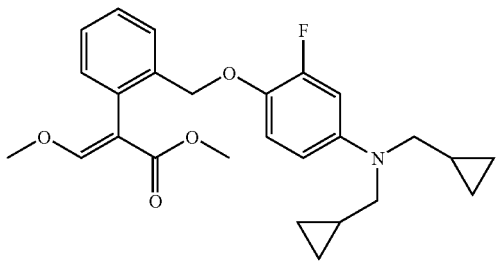 | 7.61 (s, 1H), 7.60~7.58 (m, 1H), 7.34~7.30 (m, 2H), 7.16~7.13 (m, 1H), 6.82~6.76 (m, 1H), 6.61~6.39 (m, 2H), 4.92 (s, 2H), 3.80 (s, 3H), 3.68 (s, 3H), 3.17~3.15 (m, 4H), 1.01~0.95 (m, 2H), 0.52~0.46 (m, 4H), 0.20~0.15 (m, 4H) |
| 423 | 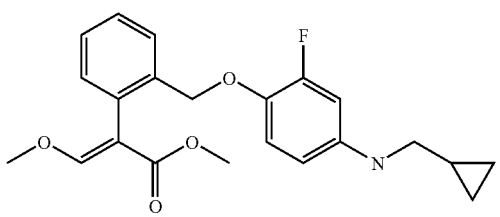 | 7.59 (s, 1H), 7.58~7.56 (m, 1H), 7.33~7.30 (m, 2H), 7.16~7.13 (m, 1H), 6.77~6.71 (m, 1H), 6.40~6.22 (m, 2H), 4.91 (s, 2H), 3.80 (s, 3H), 3.68 (s, 3H), 3.55 (b, 1H), 2.86 (d, J = 6.9, 2H), 1.08~1.03 (m, 1H), 0.56~0.50 (m, 2H), 0.23~0.18 (m, 2H) |
TABLE 3l
| | | |
|---|---|---|
| 424 | 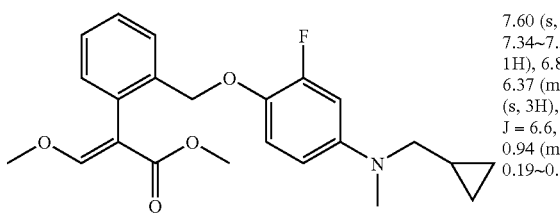 | 7.60 (s, 1H), 7.59~7.58 (m, 1H), 7.34~7.30 (m, 2H), 7.16~7.14 (m, 1H), 6.83~6.76 (m, 1H), 6.57~6.37 (m, 2H), 4.93 (s, 2H), 3.80 (s, 3H), 3.68 (s, 3H), 3.10 (d, J = 6.6, 2H), 2.88 (s, 3H), 0.96~0.94 (m, 1H), 0.52~0.46 (m, 2H), 0.19~0.14 (m, 2H) |
| 425 | 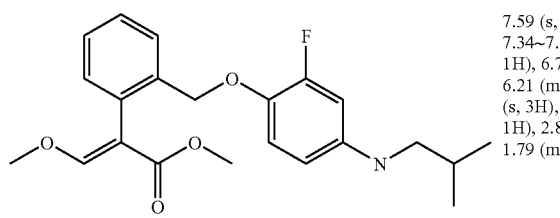 | 7.59 (s, 1H), 7.58~7.56 (m, 1H), 7.34~7.29 (m, 2H), 7.16~7.13 (m, 1H), 6.76~6.70 (m, 1H), 6.38~6.21 (m, 2H), 4.90 (s, 2H), 3.79 (s, 3H), 3.68 (s, 3H), 3.54 (b, 1H), 2.83 (d, J = 6.6, 2H), 1.88~1.79 (m, 1H), 0.96~0.94 (m, 6H) |
| 426 | 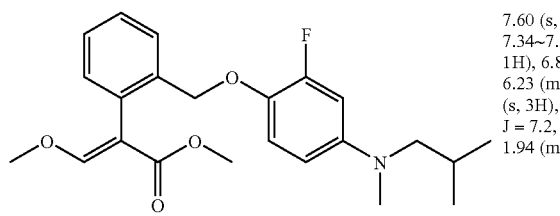 | 7.60 (s, 1H), 7.59~7.57 (m, 1H), 7.34~7.30 (m, 2H), 7.16~7.13 (m, 1H), 6.82~6.76 (m, 1H), 6.45~6.23 (m, 2H), 4.91 (s, 2H), 3.80 (s, 3H), 3.68 (s, 3H), 2.98 (d, J = 7.2, 2H), 2.86 (s, 3H), 2.03~1.94 (m, 1H), 0.91~0.88 (m, 6H) |
| 427 | 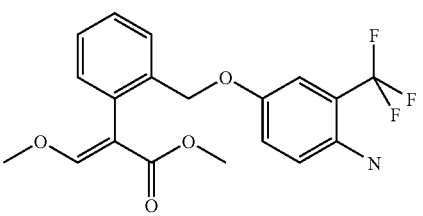 | 7.60 (s, 1H), 7.50~7.48 (m, 1H), 7.34~7.30 (m, 2H), 7.18~7.15 (m, 1H), 6.97~6.87 (m, 2H), 6.67~6.64 (m, 1H), 4.86 (s, 2H), 3.81 (s, 3H), 3.69 (s, 3H)) |

TABLE 3l-continued
| | | |
|---|---|---|
| 428 | 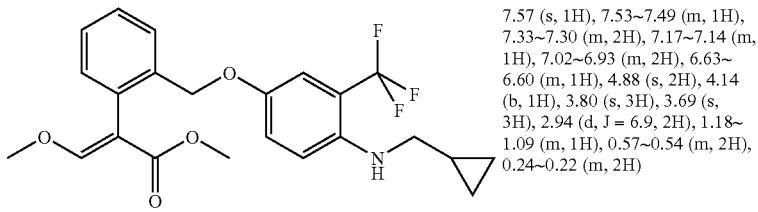 | 7.57 (s, 1H), 7.53~7.49 (m, 1H), 7.33~7.30 (m, 2H), 7.17~7.14 (m, 1H), 7.02~6.93 (m, 2H), 6.63~6.60 (m, 1H), 4.88 (s, 2H), 4.14 (b, 1H), 3.80 (s, 3H), 3.69 (s, 3H), 2.94 (d, J = 6.9, 2H), 1.18~1.09 (m, 1H), 0.57~0.54 (m, 2H), 0.24~0.22 (m, 2H) |
| 429 | 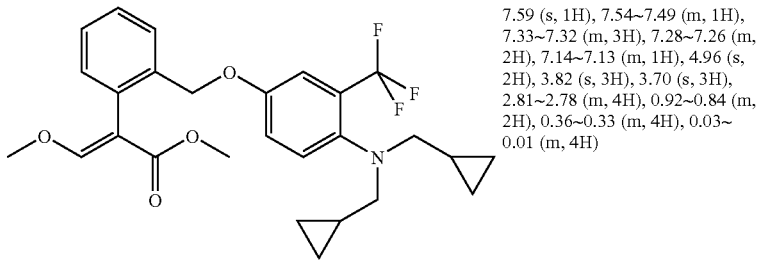 | 7.59 (s, 1H), 7.54~7.49 (m, 1H), 7.33~7.32 (m, 3H), 7.28~7.26 (m, 2H), 7.14~7.13 (m, 1H), 4.96 (s, 2H), 3.82 (s, 3H), 3.70 (s, 3H), 2.81~2.78 (m, 4H), 0.92~0.84 (m, 2H), 0.36~0.33 (m, 4H), 0.03~0.01 (m, 4H) |
TABLE 3m
| | | | |
|---|---|---|---|
| 430 | 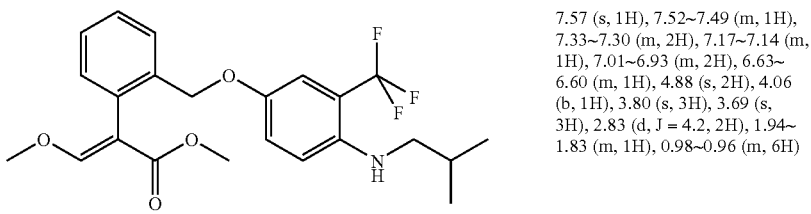 | 7.57 (s, 1H), 7.52~7.49 (m, 1H), 7.33~7.30 (m, 2H), 7.17~7.14 (m, 1H), 7.01~6.93 (m, 2H), 6.63~6.60 (m, 1H), 4.88 (s, 2H), 4.06 (b, 1H), 3.80 (s, 3H), 3.69 (s, 3H), 2.83 (d, J = 4.2, 2H), 1.94~1.83 (m, 1H), 0.98~0.96 (m, 6H) | |
| 431 | 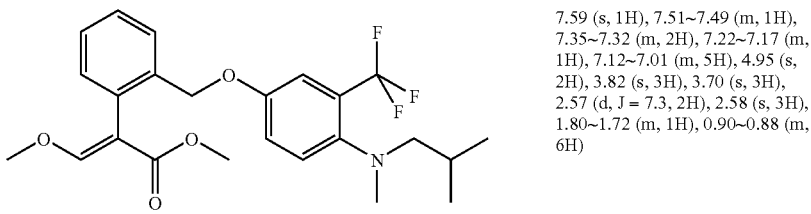 | 7.59 (s, 1H), 7.51~7.49 (m, 1H), 7.35~7.32 (m, 2H), 7.22~7.17 (m, 1H), 7.12~7.01 (m, 5H), 4.95 (s, 2H), 3.82 (s, 3H), 3.70 (s, 3H), 2.57 (d, J = 7.3, 2H), 2.58 (s, 3H), 1.80~1.72 (m, 1H), 0.90~0.88 (m, 6H) | |
| 432 | 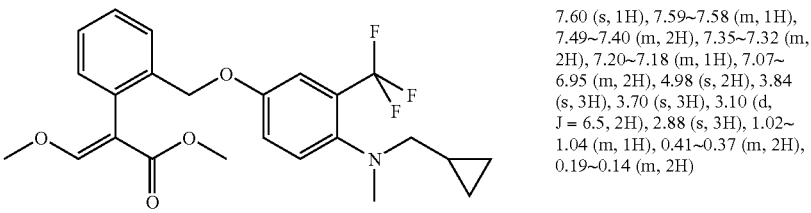 | 7.60 (s, 1H), 7.59~7.58 (m, 1H), 7.49~7.40 (m, 2H), 7.35~7.32 (m, 2H), 7.20~7.18 (m, 1H), 7.07~6.95 (m, 2H), 4.98 (s, 2H), 3.84 (s, 3H), 3.70 (s, 3H), 3.10 (d, J = 6.5, 2H), 2.88 (s, 3H), 1.02~1.04 (m, 1H), 0.41~0.37 (m, 2H), 0.19~0.14 (m, 2H) | |
| 433 | 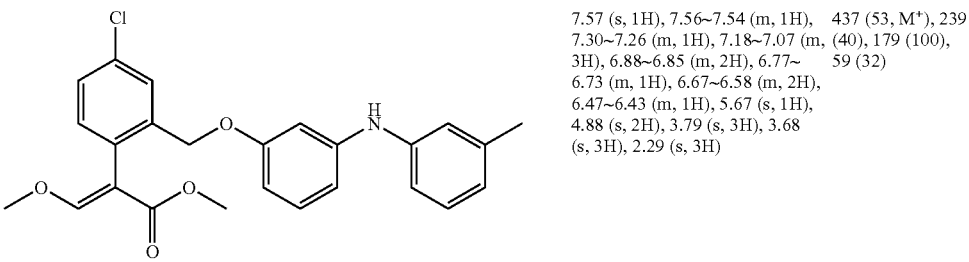 | 7.57 (s, 1H), 7.56~7.54 (m, 1H), 7.30~7.26 (m, 1H), 7.18~7.07 (m, 3H), 6.88~6.85 (m, 2H), 6.77~6.73 (m, 1H), 6.67~6.58 (m, 2H), 6.47~6.43 (m, 1H), 5.67 (s, 1H), 4.88 (s, 2H), 3.79 (s, 3H), 3.68 (s, 3H), 2.29 (s, 3H) | 437 (53, M$^+$), 239 (40), 179 (100), 59 (32) |

TABLE 3m-continued
| | | | | |
|---|---|---|---|---|
| 434 | 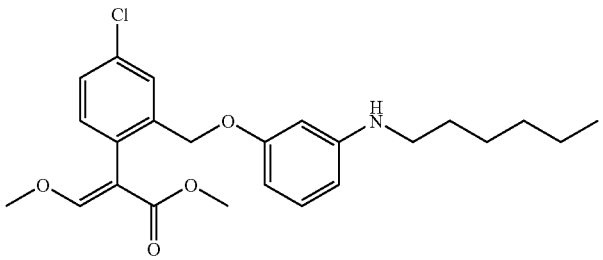 | 7.58 (s, 1H), 7.57~7.56 (m, 1H), 7.29~7.24 (m, 2H), 7.10~6.99 (m, 2H), 6.24~6.16 (m, 2H), 4.86 (s, 2H), 3.83 (s, 3H), 3.70 (s, 3H), 3.61 (s, 1H), 3.07 (t, J = 6.9, 2H), 1.59 (t, J = 6.5, 2H), 1.42~1.25 (m, 6H), 0.99 (t, J = 6.5, 3H) | 431 (18, M⁺), 239 (30), 179 (100), 59 (34) | |
| 435 | 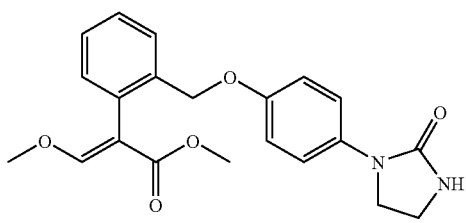 | 7.58 (s, 1H), 7.57~7.50 (m, 1H), 7.45~7.26 (m, 4H), 7.25~7.14 (m, 1H), 6.92~6.84 (m, 2H), 4.97 (b, 1H), 4.88 (s, 2H), 3.79 (s, 3H), 3.68 (s, 5H), 2.29 (s, 3H) | 382 (23, M⁺), 205 (30), 145 (100), 103 (32) | |
TABLE 3n
| | | | | |
|---|---|---|---|---|
| 436 | 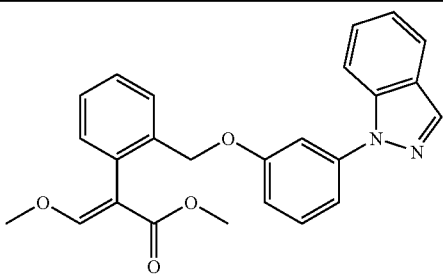 | 8.18 (s, 1H), 7.79~7.75 (m, 1H), 7.56 (s, 1H), 7.51~7.44 (m, 1H), 7.40~7.26 (m, 3H), 7.24~7.16 (m, 4H), 6.93~6.89 (m, 2H), 5.06 (s, 2H), 3.70 (s, 3H), 3.61 (s, 3H) | 414 (11, M⁺), 205 (43), 145 (100), 103 (42) | |
| 437 | 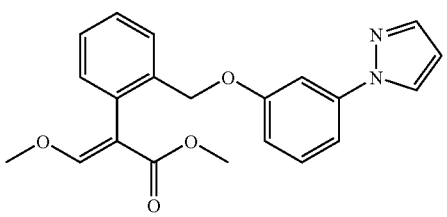 | 7.87 (s, 1H), 7.70 (s, 1H), 7.59 (s, 1H), 7.58~7.52 (m, 1H), 7.38~7.14 (m, 6H), 6.85~6.79 (m, 1H), 6.44~6.42 (m, 1H), 5.03 (s, 2H), 3.82 (s, 3H), 3.70 (s, 3H) | 364 (29, M⁺), 332 (20), 205 (41), 145 (100), 103 (37) | |
| 438 | 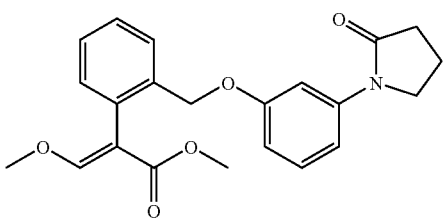 | 7.59 (s, 1H), 7.58~7.51 (m, 1H), 7.35~7.15 (m, 6H), 6.69~6.65 (m, 1H), 4.96 (s, 2H), 3.85~3.78 (m, 5H), 3.70 (s, 3H), 2.65~2.56 (m, 2H), 2.21~2.05 (m, 2H), | 381 (12, M⁺), 205 (36), 145 (100), 59 (29) | |
| 439 | 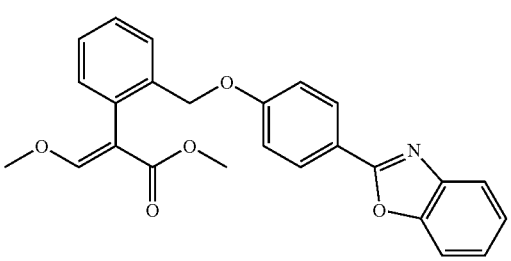 | 8.16 (d, J = 8.7 Hz, 2H), 7.72~7.12 (m, 1H), 7.61 (s, 1H), 7.56~7.53 (m, 2H), 7.37~7.30 (m, 4H), 7.26~7.21 (m, 1H), 7.01 (d, J = 8.7 Hz, 2H), 5.06 (s, 2H), 3.84 (s, 3H), 3.72 (s, 3H) | 415 (7, M⁺), 205 (41), 182 (8), 145 (100) | 138-139 |

TABLE 3n-continued

| | | | |
|---|---|---|---|
| 440 | [structure] | 8.01 (d, J = 8.7 Hz, 2H), 7.67 (s, 1H), 7.54~7.16 (m, 5H), 7.12 (d, J = 8.7 Hz, 2H), 5.11 (s, 2H), 3.91 (s, 3H), 3.67 (s, 3H) | 366 (24, M$^+$), 204 (12), 145 (100), 102 (24), 77 (28) | 146-147 |

TEST EXAMPLE 1

Inhibitory Effect on Osteoclast Formation

The inhibitory activities of the alpha-arylmethoxyacrylate derivatives prepared in the above Examples on the proliferation of osteoclasts were examined as follows.

(1-1) Isolation of Osteoclast Pregenitors and Induction of their Differentiation to Mature Osteoclasts First, a bone marrow sample containing osteoclast pregenitor cells was isolated as follows. After sacrificing 7 to 9 week-old female mice by cervical dislocation, femur and tibia were excised aseptically while removing soft tissues attached thereto, After cutting both ends of the long bones, 1 ml of an enzyme solution containing 0.1% collagenase (Gibco), 0.05% trypsin and 0.5 mM EDTA (Gibco) was injected into the bone marrow cavity at one end using a syringe with a 26-gauge needle, and the bone marrow was then collected. After stirring the recovered bone marrow for 30 min, the precipitated bone marrow cells were collected, and cultured in α-minimum essential medium (α-MEM) supplemented with 10% FBS for 24 hrs. Then, non-adherent cells, which are osteoclast pregenitors, were aliquoted onto a culture plate at a density of 2×10$^5$ cells per well, and cultured for 8 days in α-MEM supplemented with 20 ng/ml of macrophage-colony stimulating factor (M-CSF, Peprotech, USA), 30 ng/ml RANKL (Peprotech, USA), and 0.3, 1.0 or 3 µM of the compounds of the Examples. Control cells were cultured at the same condition except not adding the compounds of the Examples.

(1-2) Evaluation of Inhibition of Osteoclast (Trap-positive Multinuclear Cell) Formation After cell culture for 8 days, the adherent cells were washed with PBS and fixed with citrate-acetate-formaldehyde for 5 min. The fixed cells were incubated at 37° C. for 1 hr in acetate buffer (pH 5.0) containing naphthol AS-BI phosphate, fast Garnet GBC solution and 7 mM tartrate buffer (pH 5.0) to conduct TRAP (tartrate-resistant acid phosphatase) staining. After staining, TRAP-positive multinuclear cells having 3 or more nuclei were considered as osteoclast (see, Minkin, C., Calcif. Tissue Int. 34:285-290. 1982), and the inhibitory activities of the compounds of the Examples (0.3, 1.0 and 3.0 µM) on osteoclast formation compared to that of control are shown in Tables 4a and 4b.

TABLE 4a

| | Osteoclast formation inhibitory effects (%) | | |
|---|---|---|---|
| Compound No. | 0.3 µM | 1.0 µM | 3.0 µM |
| 15 | 92 | 100 | 100 |
| 20 | 12 | 34 | 100 |

TABLE 4a-continued

| | Osteoclast formation inhibitory effects (%) | | |
|---|---|---|---|
| Compound No. | 0.3 µM | 1.0 µM | 3.0 µM |
| 133 | 16 | 95 | 100 |
| 161 | 19 | 100 | 100 |
| 170 | 81 | 100 | 100 |
| 172 | 90 | 100 | 100 |
| 174 | 35 | 100 | 100 |
| 175 | 14 | 100 | 100 |
| 178 | 89 | 100 | 100 |
| 179 | 84 | 100 | 100 |
| 183 | 96 | 100 | 100 |
| 192 | 68 | 100 | 100 |
| 197 | 100 | 100 | 100 |
| 201 | 12 | 70 | 100 |
| 205 | 90 | 100 | 100 |
| 206 | 35 | 100 | 100 |
| 211 | 23 | 96 | 100 |
| 215 | 51 | 100 | 100 |
| 217 | 94 | 100 | 100 |
| 219 | 99 | 100 | 100 |
| 220 | 100 | 100 | 100 |
| 221 | 39 | 100 | 100 |
| 222 | 69 | 100 | 100 |
| 229 | 100 | 100 | 100 |
| 234 | 25 | 100 | 100 |
| 262 | 93 | 100 | 100 |
| 264 | 98 | 100 | 100 |
| 267 | 98 | 100 | 100 |
| 269 | 97 | 100 | 100 |
| 271 | 94 | 100 | 100 |
| 274 | 100 | 100 | 100 |
| 319 | 82 | 100 | 100 |

TABLE 4b

| | Osteoclast formation inhibitory effects (%) | | | |
|---|---|---|---|---|
| Compound No. | 0.1 µM | 0.3 µM | 1 µM | 3 µM |
| 348 | | 24 | 99 | 100 |
| 349 | 2 | 53 | 100 | 100 |
| 361 | | | 95 | 100 |
| 367 | | | 87 | 100 |
| 372 | | | 91 | 100 |
| 380 | | 8 | 51 | 100 |
| 381 | | 5 | 67 | 100 |
| 383 | | 6 | 94 | 100 |
| 386 | 100 | 100 | 100 | 100 |
| 387 | 1 | 100 | 100 | 100 |
| 388 | 0 | 99 | 100 | 100 |
| 390 | 2 | 94 | 99 | 100 |
| 391 | | 4 | 50 | 100 |
| 392 | | 2 | 95 | 100 |
| 394 | 0 | 98 | 100 | 100 |
| 397 | | 22 | 100 | 100 |
| 399 | 0 | 70 | 100 | 100 |

TABLE 4b-continued

| Compound No. | Osteoclast formation inhibitory effects (%) | | | |
|---|---|---|---|---|
| | 0.1 μM | 0.3 μM | 1 μM | 3 μM |
| 400 | 0 | 53 | 99 | 100 |
| 404 |  | 9 | 63 | 100 |
| 406 | 41 | 100 | 100 | 100 |
| 408 | 0 | 52 | 100 | 100 |
| 413 |  | 11 | 100 | 100 |
| 414 |  | 32 | 100 | 100 |
| 415 | 5 | 57 | 100 | 100 |
| 416 | 0 | 75 | 100 | 100 |
| 417 |  | 24 | 97 | 100 |
| 418 |  | 11 | 81 | 100 |
| 421 |  | 14 | 100 | 100 |
| 422 | 11 | 98 | 100 | 100 |
| 423 | 0 | 51 | 100 | 100 |
| 424 | 0 | 92 | 100 | 100 |
| 425 | 0 | 51 | 100 | 100 |
| 426 | 25 | 100 | 100 | 100 |

As can be seen from Tables 4a and 4b, the α-arylmethoxyacrylate compounds of the present invention have an excellent inhibitory effect on osteoclast formation.

(1-3) Evaluation of Inhibitory Effect on Resorption Activity of Osteoclast

In order to evaluate the effect of the compounds synthesized in the Examples on the resorption activity of the osteoclasts, the differentiated osteoclasts were cultured on a calcium phosphate-coated plate (OAAS™, OCT, Korea) (Choi et al., *Eur. J. Immunol.* 31:2179-2188, 2001). After finishing culture, the plate was washed with distilled water, and 50 μl/well of 5% sodium hypochlorite was added to the plate. The plate was let alone for 5 min, washed again with distilled water to remove the adherent cells, and dried at room temperature. Then, the area of formed resorption pits was calculated by means of Image Pro Plus software (Media Cybernetics Ver. 3.0). Reduction (%) of the resorption pit area of osteoclasts treated with the compounds of the Examples as compared to that of the control are shown in Table 5.

TABLE 5

| Compound No. | 0.3 uM | 1 uM | 3 uM |
|---|---|---|---|
| 15 | 41 | 57 | 93 |
| 20 |  | 26 | 47 |
| 133 | 75 | 99 | 100 |
| 161 | 94 | 100 | 100 |
| 170 | 0 | 100 | 100 |
| 172 | 90 | 100 | 100 |
| 174 | 100 | 100 | 100 |
| 175 | 99 | 100 | 100 |
| 178 | 97 | 100 | 100 |
| 179 | 86 | 100 | 100 |
| 183 | 100 | 100 | 100 |
| 192 | 100 | 100 | 100 |
| 197 | 100 | 100 | 100 |
| 201 | 100 | 100 | 100 |
| 205 |  | 100 | 100 |
| 206 | 97 | 100 | 100 |
| 211 | 96 | 100 | 100 |
| 215 | 97 | 100 | 100 |
| 217 |  | 100 | 100 |
| 219 |  | 88 | 100 |
| 220 | 42 | 70 | 73 |
| 221 | 94 | 100 | 100 |
| 222 | 100.0 | 100 | 100 |
| 229 | 0.00 | 100 | 100 |
| 234 | 95 | 100 | 100 |
| 262 | 93 | 100 | 100 |
| 264 | 100 | 100 | 100 |
| 267 | 100 | 100 | 100 |
| 269 | 100 | 100 | 100 |
| 271 | 30 | 94 | 42 |
| 274 | 100 | 100 | 100 |
| 319 | 0 | 100 | 100 |

As can be seen from Table 5, the resorption pit area in the plate treated with one of the compounds of the Examples was remarkably reduced as compared to that of the control, and the resorption activity of osteoclast was almost completely inhibited when more than 0.1 μM of any of the compounds of the Examples was used. This result demonstrates that the α-arylmethoxyacrylate compounds of the present invention have an excellent inhibitory activity against osteoclast.

TEST EXAMPLE 2

Cytotoxicity Test (2-1) Cytotoxicity Against Osteoclast Pregenitor

In order examine the toxicities of the compounds of the Examples against osteoclast pregenitors, pregenitor cells were aliquotted onto a 96-well microplate at a density of $2\times10^5$ cells per well, treated with 2, 4 and 8 μM of the test compounds, respectively, and cultured for 48 hrs in α-MEM supplemented with 20 ng/ml of M-CSF (Peprotech, USA) using 37° C. incubator (5% $CO_2$). At 3 hrs before the culture was finished, 50 μl of MTT (3-(4,5-dimethylthiazol-2-yl)-2,5-diphenyltetrazolium bromide) solution (50 μg/ml) was added to each well. Upon completion of the cell culture, the supernatant was removed, and the precipitated dye was reacted with 100 μl of isopropanol/0.04 N HCl at room temperature for 30 min to dissolve it. The absorbances of the wells were measured at 550 nm, and the relative absorbance of each well relative to that of the control (set as 100) is shown in Table 6.

TABLE 6

| Compound No. | 2 uM | 4 uM | 8 uM |
|---|---|---|---|
| Control | 100 | 100 | 100 |
| 133 | 93 | 104 | 102 |
| 205 | 101 | 109 | 104 |
| 206 | 102 | 102 | 108 |
| 211 | 88 | 103 | 103 |
| 215 | 96 | 102 | 107 |
| 217 | 90 | 96 | 107 |
| 219 | 90 | 100 | 99 |
| 220 | 89 | 98 | 96 |
| 221 | 96 | 96 | 99 |
| 222 | 97 | 108 | 101 |

As can be seen form Table 6, the α-arylmethoxyacrylate compounds of the present invention have little cytotoxicity against undifferentiated bone marrow cells.

(2-2) Cytotoxicity Test Against Osteoblast

In order to examine the toxicity of the compounds of the Examples against osteoblasts, human osteosarcoma-derived cell line, MG-63 (ATCC No. CRL-1427) cells were treated with 0.1, 0.3, 1.0 and 3.0 μM of the compounds of the Examples, and cultured in DMEM supplemented with 10%

FBS (fetal bovine serum). Cytotoxicity was measured in accordance with the method of (2-1), and the results are shown in Tables 7a and 7b.

TABLE 7a

| Compound No. | 0.11 uM | 0.33 uM | 1 uM | 3 uM |
|---|---|---|---|---|
| Control | 100 | 100 | 100 | 100 |
| 15 | | 105 | 85 | 76 |
| 20 | | 106 | 106 | 105 |
| 133 | 103 | 108 | 107 | 103 |
| 179 | 117 | 111 | 108 | 106 |
| 197 | 112 | 101 | 111 | 103 |
| 211 | 103 | 101 | 105 | 106 |
| 234 | | 98 | 115 | 97 |
| 264 | 103 | 107 | 104 | 92 |
| 269 | | 81 | 94 | 88 |
| 271 | | 114 | 79 | 64 |
| 274 | 113 | 108 | 106 | 94 |

TABLE 7b

| Compound No. | 0.33 μM | 1 μM | 3 μM |
|---|---|---|---|
| Control | 100 | 100 | 100 |
| 386 | 101 | 69 | 68 |
| 388 | 105 | 84 | 81 |
| 391 | 104 | 99 | 111 |
| 394 | 113 | 105 | 110 |
| 399 | 96 | 76 | 65 |
| 404 | 83 | 92 | 94 |

As can be seen from Tables 7a and 7b, the compounds of the Examples have little cytotoxicity against osteoblasts.

TEST EXAMPLE 3

Clinical Test (3-1) Bone Mineral Density (BMD) Determination of Female Mice Undergone Ovariectomy (Control)

The effect of Compound Nos. 274 and 388 of the present invention on BMD of female mice with osteoporosis induced by ovariectomy was examined as follows.

Specifically, after anesthetizing female mice used as a control by abdominal administration with a mixture of 10 mg/kg body weight of Ketamin HCl (Ketara) and 0.15 ml/kg body weight of 2% Xylazine HCl (Roupun), the lumbar dorsum of each mouse was shaved bilaterally and the exposed skin was prepared for aseptic surgery by a 10% povidone-iodine scrub followed by a 70% alcohol wipe. A 1-cm incision was made in the central region of the abdomen, and the ovaries were identified with caution not to damage the main organs such as the liver and diaphragm. The ovaries were ligated with a suture thread, and then severed. Thereafter, each organ was relocated to its original position, and the incision was closed with a suture thread in an interrupted pattern. After ovariectomy, the mice were injected with 0.088 mg/kg body weight of gentamicin to prevent infection.

To investigate the change in BMD of the mice, bone mineral density was measured before the ovariectomy and every two weeks for 8 weeks after the ovariectomy using a bone mineral densitometer, XCT 540 Research SA (Stratec, Germany). Specifically, BMD measurement was made at a voxel size of 0.1 mm×0.1 mm, threshold values of 280 mg/cm$^2$ for cancellous bone and 500 mg/cm$^2$ for compact bone, and the analysis sites at the proximal tibias were determined by Scout scans (10 mm/sec). BMD was measured at three slices at the determined sites by CT scans (7 mm/sec), and the measurement was performed twice or more at the same site.

(3-2) Determination of BMD in Female Multiparous Mice after Ovariectomy

Multiparous mice each weighing 250 to 350 g were subjected to ovariectomy in accordance with the method of (3-1). From the 2$^{nd}$ day to 12$^{th}$ week after the ovariectomy, the mice were injected subcutaneously once a day with 0.5 and 1 mg/kg body weight/day of Compound Nos. 274 and 388, respectively. Alternatively, the mice were administered orally with 2.5 and 7.5 mg/kg body weight/day of Compound Nos. 274 and 388. BMD was measured before the ovariectomy, and during the period of the 2$^{nd}$ week to 11$^{th}$ week after the ovariectomy.

Figure 1B:
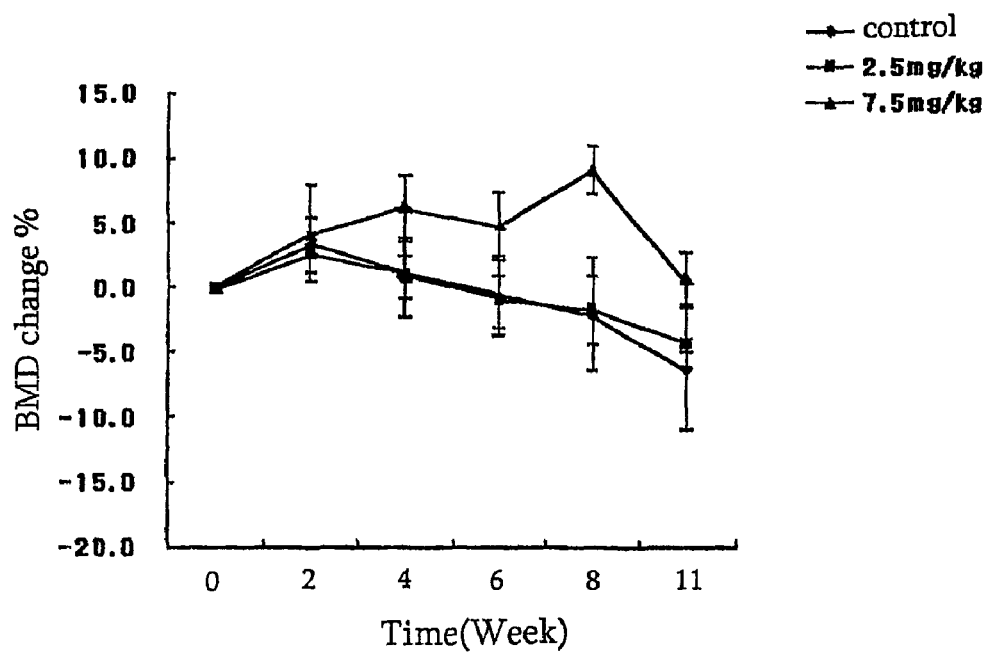

FIGS. 1a and 1b show the result obtained with the Compound No. 274, wherein the controls not treated with the Compound No. 274 showed a decrease of BMD (subcutaneous injection: 4.0%, oral administration: 6.3%), while the mice treated with the Compound No. 274 showed no decrease of BMD in the case of subcutaneous injection, and little increase of BMD (0.8%) in the case of oral administration.

Figure 2A:
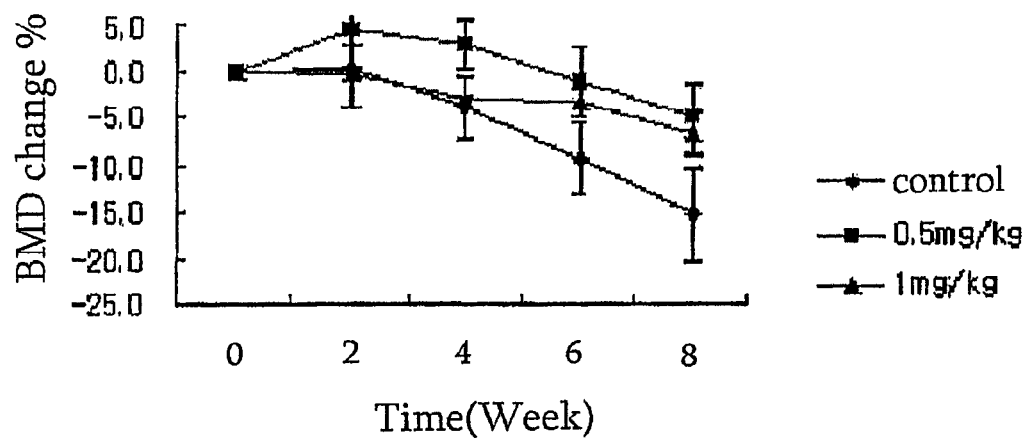
FIGS. 2a and 2b: the changes in BMD of multiparous mice ovariectomized to induce osteoporosis observed when the mice were orally administered with compounds according to the present invention.
Figure 2B:
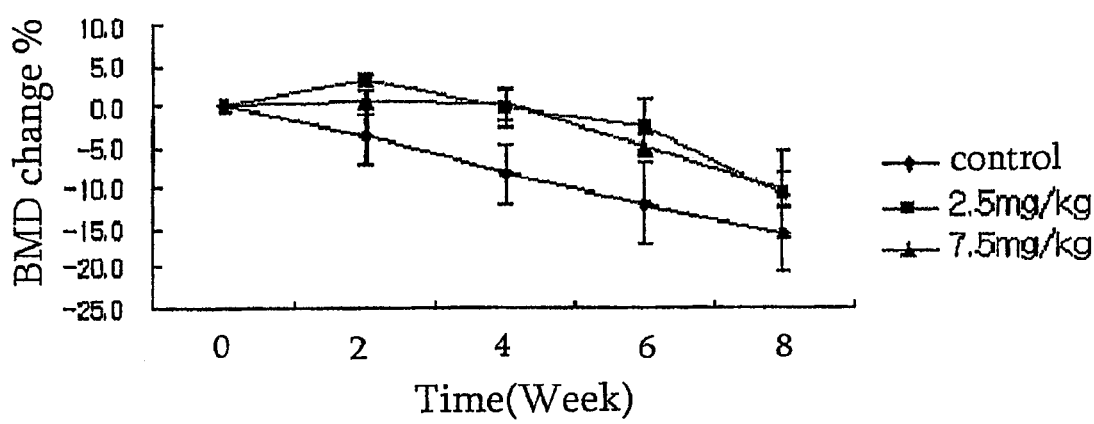

On the other hand, FIGS. 2a and 2b show the result obtained with the Compound No. 388, wherein the controls not treated with the Compound No. 388 showed sudden decreases of BMD (subcutaneous injection: 15.4%; oral administration: 15.60%) after 8 weeks, while the mice treated with the Compound No. 388 showed sudden decreases in the BMD level (subcutaneous injection: 5.0% at 0.5 mg/kg and 6.7% at 1 mg/kg; oral administration: 10.6% at 2.5 mg/kg and 10.2% at 7.5 mg/kg).

Therefore, it can be concluded that the α-arylmethoxyacrylate compounds of the present invention are effective for preventing and treating osteoporosis.

TEST EXAMPLE 4

Pharmacokinetics (4-1) In vitro Pharmacokinetics

Metabolic stabilities of the compounds of the Examples were examined by employing microsome samples prepared from the human liver.

Each 20 μM of the compounds were reacted with 1 mg/ml of liver microsome and the half-lives and one-hour stabilities of the compounds were determined. The results are shown in Table 8.

TABLE 8

| Comp. No. | Half-life (min) | One-hour stability (%) |
|---|---|---|
| 15 | 36.9 | 33 |
| 161 | 45.6 | 40 |
| 179 | >180 | 70 |
| 211 | 106 | 60 |
| 234 | >180 | 83 |
| 264 | >180 | 80 |
| 267 | >180 | 70 |
| 274 | >180 | 72 |
| 386 | 40.66 | |
| 388 | 30.71 | |
| 391 | 107.2 ± 18.6 | |
| 394 | 55.5 ± 12.0 | |
| 399 | 43.0 ± 1.8 | |
| 404 | 57.4 ± 2.3 | |
| 415 | 24.87 | |
| 416 | 43.86 | |
| 426 | 42.7 ± 2.1 | |

The above result demonstrates that the alpha-arylmethoxyacrylate derivatives of the present invention have a high metabolic stability.

(4-2) In vivo Pharmacokinetics Using Female Mice (4-2-1) Administration of Compounds and Serum Separation Female mice each weighing about 250 g were divided into groups of 5 mice each. The mice were anesthetized with ether, catheterized in their femoral artery and vein, respectively, and administered with 0.5 mg/kg body weight of compounds 234 and 274, and 5 mg/kg body weight of compounds 388, 404 and 415, respectively, via intravenous injection. Alternatively, 15 mg/kg body weight of compound 274 and 10 mg/kg body weight of compound 234 were orally administered to the mice.

At 0, 5, 10, 15 and 30 minutes and 1, 2, 4, 6, 9 and 12 hours after the intravenous injection, or at 0, 10, 20 and 40 minutes and 1, 2, 4, 6, 9 and 12 hours after the oral administration, 0.3 ml blood samples were taken from the mice through femoral artery. The blood samples were kept on an ice bath for 30 minutes and centrifuged at 3,000 rpm for 10 minutes to obtain a supernatant (serum). The supernatant samples were stored at −20° C.

(4-2-2) Determination of the Concentration of the Compounds in the Serum

In the following experiment, HPLC-grade methanol and acetonitrile (Merck) and a HPLC system (Shimadzu LC-10AD) were used.

Standard solution: Compounds 234, 274, 388, 404 and 415 were respectively dissolved in methanol to a concentration of 1 mg/ml to obtain stock solutions. The stock solutions were diluted with methanol to obtain standard solutions having concentrations of 40, 20, 10, 2, 1, 0.5, 0.2, 0.05 and 0.02 μg/ml, respectively.

Standard calibration curve: A stand calibration curve was prepared by employing calibration concentrations of 0.002, 0.005, 0.02, 0.05, 0.1, 0.2, 1, 2 and 4 μg/ml.

10 μl each of the standard solutions prepared above was added to 100 μl of normal serum sample and diluted 10 times. 250 μl of acetonitrile was added to the resulting dilution and the mixture was centrifuged for 10 minutes to obtain a supernatant. 300 μl of the supernatant was dried by evaporation under a nitrogen atmosphere and reconstituted by adding 50 μl of methanol. 20 μl of the resulting solution was analyzed by HPLC to prepare a standard calibration curve. HPLC was performed with Shimadzu ODS2 column (4.6×250 mm, 5 μm by employing a mixture of methanol/water (90/10 (v/v)) as the mobile phase at a flow rate of 1.2 ml/min, and measuring the absorbance at 240 nm.

The resulting stand calibration curves exhibited good linearity.

Extraction: 100 μl of the serum sample obtained in (4-2-1) was put into a 1 ml microtube and 10 μl of methanol was added thereto. 250 μl of acetonitrile was added to the microtube and the mixture was centrifuged for 10 minutes to obtain a supernatant. 300 μl of the supernatant was dried by evaporation under a nitrogen atmosphere and reconstituted by adding 50 μl of methanol. 20 μl of the resulting solution was analyzed by the HPLC method as above.

(4-2-3) Determination of Pharmacokinetic Parameters

Average concentrations of the compounds in the serum samples were plotted in a semi-log scale against the time lapsed after the administration, and the pharmacokinetic parameters were determined as a non-compartment open model by employing WinNonlin® program (Pharsight Corporation). Average values for the pharmacokinetic parameters are shown in Table 9.

TABLE 9

| Comp. No. | Admin. route | AUC[1] (μg × hr/ml) | CL[2] (ml/hr) | Half-life (hr) | Vd[3] (ml/kg) | Bioavailability (%) |
|---|---|---|---|---|---|---|
| 234 | I.V. | 477.6 ± 96.4 | 1.1 ± 0.2 | 10.6 ± 4.8 | 15.2 ± 5.2 | 35.4 |
|  | Oral | 680.4 ± 426.2 | 19.5 ± 10.6 | 12.8 ± 7.7 | 354.4 ± 245.6 |  |
| 274 | I.V. | 47.2 ± 25.8 | 14.3 ± 9.7 | 3.5 ± 2.3 | 50.3 ± 9.8 | 8.5 |
|  | Oral | 80.6 ± 45.4 | 7.5 ± 3.4 | 4.2 ± 3.7 | 43.4 ± 46.8 |  |
| 388 | I.V. | 112.6 ± 13.0 | 2.9 ± 0.5 | 7.3 ± 1.2 | 27.4 ± 2.0 | — |
| 404 | I.V. | 97.2 ± 14.8 | 3.4 ± 0.5 | 10.2 ± 1.9 | 46.2 ± 6.4 | — |
| 415 | I.V. | 176.4 ± 32.9 | 1.9 ± 0.4 | 10.79 ± 1.61 | 27.0 ± 1.2 | — |

[1]AUC: Area under the curve of blood concentration versus time
[2]CL: Clearance
[3]Vd: Volume of distribution As shown in Table 9, half-lives of the inventive compounds upon I.V. administration ranged from 3.5 to 11 hours. This result shows that the inventive compounds have suitable in vivo stabilities for use as drugs.

TEST EXAMPLE 5

In Vivo Toxicity Test

In order to determine the acute toxicities of the compounds prepared in Examples, 6-week old specific pathogen-free (SPF) rats each weighing about 20 g were divided into groups of 10 rat each.

In case of subcutaneous administration, each of the compounds was dissolved in 5% PEG400 solution to a concentration of 20 mg/ml, the resulting solution was serially diluted with 5% PEG400 solution to concentrations of 5, 2.5, 1.25 and 0.625 mg/ml, and the dilutions were subcutaneously injected once to the rats at a dose of 10 ml/kg body weight.

In case of oral administration, each of the compounds was dissolved in soybean oil to a concentration of 180 mg/ml, the resulting solution was serially diluted with soybean oil to concentrations of 80, 20 and 5 mg/ml, and the dilutions were orally administered once to the rats at a dose of 20 ml/kg body weight.

Citrate-phosphate buffer (pH 4.0) was used as a solvent for the preparation of the injection and oral formulations.

During 2 weeks after the administration of the compounds, the death rate, clinical symptoms and weight changes of the rats were observed, and hematological and biochemical tests on blood samples were performed. Then, the rats were sacrificed and the internal organs were visually examined to check any abnormal signs in the organs of chest and abdomen.

LD$_{50}$ values of the compounds depending on the administration route are shown in Table 10.

TABLE 10

| Comp. No. | LD$_{50}$ (mg/kg body weight) | |
|---|---|---|
| | SC | PO |
| 15 | >50 | >2000 |
| 169 | 10 | >1000 |
| 179 | 42 | 500 |
| 211 | 51 | 500 |
| 234 | 7 | 100-300 |
| 264 | 25 | 269 |
| 267 | 5 | 100-300 |
| 274 | 11 | 460 |
| 388 | — | 110-130 |

As shown in Table 10, most of the compounds exhibited only low levels of toxicity.

While some of the preferred embodiments of the subject invention have been described and illustrated, various changes and modifications can be made therein without departing from the spirit of the present invention defined in the appended claims.

What is claimed is:

1. A method of treating osteoporosis, comprising administering a compound of formula (1) or its pharmacologically acceptable salt to a subject in need of such treatment:

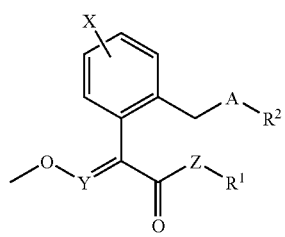

(1)

wherein, A is O, S, CH$_2$, O—N=CH, or O—N=C(CH$_3$);
X is H or halogen;
Y is N or CH;
Z is O or NH;
R$^1$ is H or C$_{1-4}$ alkyl;
R$^2$ is unsubstituted or substituted aryl or unsubstituted or substituted heteroaryl,
wherein,
when the aryl is substituted, the substituent is at least one substituent selected from the group consisting of halogen, cyano, nitro, C$_{1-4}$ haloalkyl, C$_{2-4}$ haloalkenyl, hydroxy, C$_{1-8}$ alkyl, C$_{1-8}$ alkoxy, C$_{1-4}$ alkoxy C$_{1-4}$ alkoxy, C$_{1-4}$ dialkoxy C$_{1-4}$ alkyl, 1,3-dioxolan-2-yl, 1,3-dioxan-2-yl, C$_{2-8}$ alkenyloxy, C$_{2-4}$ alkynyloxy, C$_{3-6}$ cycloalkyl C$_{1-4}$ alkoxy, hydroxy C$_{1-4}$ alkyl, C$_{1-4}$ acyloxy, C$_{1-4}$ alkylcarbonyl, C$_{3-6}$ cycloalkylcarbonyloxy, C$_{1-4}$ alkoxycarbonyl, C$_{1-4}$ dialkylamino C$_{1-4}$ alkoxy, at least one N- or O-containing C$_{2-5}$ heterocyclo C$_{1-4}$ alkoxy, 2-morpholinoethoxy, dicyano C$_{2-4}$ alkenyl, cyano C$_{1-4}$ alkyloxy, acyl C$_{2-4}$ alkenyl, C$_{3-6}$ cycloalkyloxy, phenylcarbonyloxy, trifluoroacetyl, formyl, tetrahydropyranyloxy, C$_{1-4}$ alkoxycarbonyl C$_{1-4}$ alkoxy, C$_{1-4}$ alkylcarbonyl C$_{1-4}$ alkyl, C$_{1-4}$ alkoxycarbonyl C$_{1-4}$ alkyl, C$_{1-4}$ alkylcarbonyl C$_{2-4}$ alkenyl, C$_{1-4}$ alkylcarbonylhydroxy C$_{1-4}$ alkyl, C$_{1-4}$ alkylcarbonylhalo C$_{1-4}$ alkyl, hydroxyhalo C$_{1-4}$ alkyl, pyrazolyl, pyrrolidonyl, benzopyrazolyl, imidazolidonyl, benzoxazolyl, tetrazolyl, substituted amino C$_{1-2}$ alkyl, substituted amino, in which the substituted amino or substituted amino C$_{1-2}$ alkyl is represented by-(CH$_2$)$_n$-NR$^3$ R$^4$, in which n is 0, 1 or 2, R$^3$ and R$^4$ are each independently H, C$_{1-8}$ alkyl, C$_{1-8}$ haloalkyl, C$_{2-8}$ alkenyl, C$_{3-8}$ cycloalkyl, C$_{3-8}$ cycloalkyl C$_{1-4}$ alkyl, C$_{1-4}$ alkoxy C$_{1-4}$ alkyl, C$_{3-8}$ cycloalkoxy C$_{1-4}$ alkyl, at least one N, O or S-containing C$_{2-7}$ heterocyclic C$_{1-4}$ alkyl, or an aryl, or R$^3$ and R$^4$ are fused together with the nitrogen atom to which they are attached to form a heterocyclic ring; and
wherein the heteroaryl is an N-containing heteroaryl or chromone,
wherein the substituted N-containing heteroaryl has at least one substituent selected from the group consisting of amino, halogen, C$_{1-6}$ haloalkyl, C$_{1-8}$ alkyl, C$_{1-8}$ alkoxy, phenyl, piperidinyl, morpholinyl, pyrrolidinyl, N-C$_{1-4}$ alkylanilinyl, N-methylpiperazinyl, C$_{1-4}$ alkylcarbonyl C$_{1-4}$ alkylthio, and C$_{1-4}$ dialkylaminocarbonylthio; and
wherein the substituted chromone has a phenyl substituent which is unsubstituted or substituted with halogen or C$_{1-4}$ alkoxy.

2. The method of claim 1, wherein the aryl group for R$^2$ is phenyl or naphthyl.

3. The method of claim 1, wherein the heteroaryl group is selected from the group consisting of pyridinyl, pyrimidinyl, pyrazolyl, 1,3,4-thiadiazolyl, cromon-2-yl, cromon-4-yl, and indolyl.

4. The method of claim 1, wherein the N-containing heteroaryl is selected from the group consisting of pyridyl, pyrimidyl, pyrrolyl, imidazolyl, oxazolyl, thiazolyl, triazolyl, pyrazolyl, tetrazolyl, indazolyl, benzoxazolyl, benzothiazolyl, benzoimidazolyl, benzotriazolyl, isoquinolyl, and quinazolyl.

5. The method of claim 1, wherein the compound is represented by formula (1a):

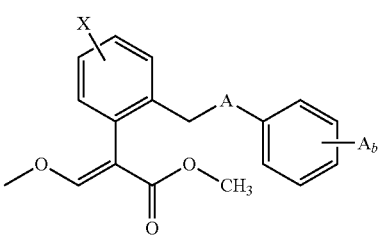

(1a)

wherein, A is O or O—N=C(CH$_3$);
X is H, F or Cl;
A$_b$ is at least one group selected from the group consisting of halogens, C$_{1-4}$ haloalkyl, C$_{2-4}$ haloalkenyl, C$_{1-8}$ alkyl, C$_{1-8}$ alkoxy, C$_{1-4}$ alkoxy C$_{1-4}$ alkoxy, C$_{1-4}$ dialkoxy C$_{1-4}$ alkyl, 1,3-dioxolan -2yl, 1,3-dioxan-2-yl, C$_{2-8}$ alkenyloxy, C$_{2-4}$ alkynyloxy, C$_{3-6}$ cycloalkyl C$_{1-4}$ alkoxy, hydroxy C$_{1-4}$ alkyl, C$_{1-4}$ dialkylamino C$_{1-4}$ alkoxy, at least one N or O-containing C$_{2-5}$ heterocyclo C$_{1-4}$ alkoxy, 2-morpholinoethoxy, substituted amino, and substituted amino C$_{1-2}$ alkyl; and
wherein the substituted amino or substituted amino C$_{1-2}$ alkyl is represented by-(CH$_2$)$_n$-NR$^3$ R$^4$, in which n is 0, 1 or 2, R$^3$ and R$^4$ are each independently H, C$_{1-8}$ alkyl, C$_{1-8}$ haloalkyl, C$_{2-8}$ alkenyl, C$_{3-8}$ cycloalkyl, C$_{3-8}$ cycloalkyl $C_{1-4}$ alkyl, $C_{1-4}$ alkoxy $C_{1-4}$ alkyl, $C_{3-8}$ cycloalkoxy $C_{1-4}$ alkyl, at least one N, O or S-containing $C_{2-7}$ heterocyclic $C_{1-4}$ alkyl, or an aryl, or $R^3$ and $R^4$ are fused together with the nitrogen atom to which they are attached to form a heterocyclic ring.

6. The method of claim 1, wherein the compound is selected from the group consisting of:

(E)-methyl 2-(2-((4-octylphenoxy)methyl)-3-methoxyacrylate;

(E)-methyl 2-(2-((4-(cyclopropylmethoxy)phenoxy)methyl)-4-chlorophenyl)-3-methoxyacrylate;

(E)-methyl 2-(2-((4-(2-methoxyethoxy)phenoxy)methyl)-4-chlorophenyl)-3-methoxyacrylate;

(E) -methyl 2-(2-((4-(allyloxy)phenoxy)methyl)-4-chlorophenyl)-3-methoxyacrylate;

(E)-methyl 2-(2-((4-(2-methoxyethoxy)phenoxy)methyl)-4-fluorophenyl)-3-methoxyacrylate;

(E)-methyl 2-(2-((4-(allyloxy)phenoxy)methyl)-4-fluorophenyl)-3- methoxyacrylate;

(E)-methyl 2-(2-((4-(1-methylpropaneoxy)phenoxy)methyl)-4-fluorophenyl)-3-methoxyacrylate;

(E-methyl 2-(2-((3-(2-morpholinoethoxy)phenoxy)methyl)phenyl)-3-methoxyacrylate;

(E)-methyl 2-(2-((3-(1,3-dioxan-2-yl)phenoxy)methyl)phenyl)-3-methoxyacrylate;

(E)-methyl 2-(2-((4-(allyloxy)phenethyl)phenyl)-3-methoxyacrylate;

(E)-methyl 2-(((({1E} -1-(3-(n-hexyloxy)phenyl)ethylidene)amino)oxy)methyl)phenyl-3- methoxyacrylate;

(E)-methyl 2-(((({1E}-1-(3 -(n-cyanomethyloxy)phenyl)ethylidene)amino)oxy)methyl)phenyl-3-methoxyacrylate;

(E)-methyl 2-(2-((3-morpholinophenoxy)methyl)phenyl)-3-methoxyacrylate;

(E)-methyl 2-(2-((3-morpholinophenoxy)methyl)-4-chlorophenyl)-3-methoxyacrylate;

(E)-methyl 2-(2-((3-(piperidin-1-yl)phenoxy)methyl)phenyl)-3-methoxyacrylate;

(E)-methyl 2-(2-((4-(piperidin-1-yl)phenoxy)methyl)phenyl)-3-methoxyacrylate;

(E)-methyl 2-(2-((3-(4-methylpiperizan-1-yl)phenoxy)methyl)phenyl)-3-methoxyacrylate;

(E)-methyl 2-(2-((4-(N-isobutylamino)-2-fluorophenoxy)methyl)phenyl)-3-methoxyacrylate;

(E)-methyl 2-(2-((4-(N-isobutyl-N-methylamino)-2-fluorophenoxy)methyl)phenyl)-3-methoxyacrylate;

(E)-methyl 2-(2-4-(N-cyclopropylmethylamino)-2-fluorophenoxy)methyl)phenyl)-3-methoxyacrylate;

(E)-methyl 2-(2-((4-(N-cyclopropylmethyl-N-methylamino)-2-fluorophenoxy)methyl)phenyl)-3-methoxyacrylate;

(E)-methyl 2-(2-((3-fluoro-4-(piperidin-1-yl)phenoxy)methyl)phenyl)-3-methoxyacrylate;

(E)-methyl 2-(2-((2-fluoro-4-morpholinophenoxy)methyl)phenyl)-3-methoxyacrylate;

(E)-methyl 2-(2-((3-(morpholinomethyl)phenoxy)methyl)phenyl)-3-methoxyacrylate;

(E)-methyl 2-(2-((3-(N-methyl-N-phenylamino)phenoxy)methyl)-4-chlorophenyl)-3-methoxyacrylate;

(E)-methyl 2-(2-((3-((4-methylpiperizan-1-yl)methyl)phenoxy)methyl)phenyl)-3-methoxyacrylate;

(E)-methyl 2-(2-((6-(pyrrolidin-1-yl)pyridin-2-yloxy)methyl)phenyl)-3-methoxyacrylate;

(E)-methyl 2-(2-((6-(piperidin-1-yl)pyridin-2-yloxy)methyl)phenyl)-3-methoxyacrylate;

(E)-methyl 2-(2-((5-(morpholino)pyridin-2-yloxy)methyl)phenyl)-3-methoxyacrylate;

and (E)-methyl 2-(2-((6-(morpholino)pyridin-2-yloxy)methyl)phenyl)-3-methoxyacrylate.

7. The method of claim 1, wherein the compound inhibits osteoclast formation or resorption activity.

\* \* \* \* \*